(12) United States Patent
Leksic et al.

(10) Patent No.: US 9,505,744 B2
(45) Date of Patent: Nov. 29, 2016

(54) SOLID STATE FORMS OF VILAZODONE AND VILAZODONE HYDROCHLORIDE

(71) Applicant: Assia Chemical Industries Ltd., Petach Tikva (IL)

(72) Inventors: Edislav Leksic, Zagreb (HR); Dubravka Pavlicic, Zagreb (HR); Dijana Skalec Samec, Jastrebarsko (HR); Jasna Dogan, Zagreb (HR)

(73) Assignee: Assia Chemical Industries LTD., Petach Tikva (IL)

( * ) Notice: Subject to any disclaimer, the term of this patent is extended or adjusted under 35 U.S.C. 154(b) by 0 days.

(21) Appl. No.: 14/359,683

(22) PCT Filed: Nov. 21, 2012

(86) PCT No.: PCT/US2012/066324
§ 371 (c)(1),
(2) Date: May 21, 2014

(87) PCT Pub. No.: WO2013/078361
PCT Pub. Date: May 30, 2013

(65) Prior Publication Data
US 2014/0323498 A1   Oct. 30, 2014

Related U.S. Application Data

(60) Provisional application No. 61/563,150, filed on Nov. 23, 2011, provisional application No. 61/583,368, filed on Jan. 5, 2012, provisional application No. 61/584,499, filed on Jan. 9, 2012, provisional application No. 61/590,412, filed on Jan. 25, 2012, provisional application No. 61/367,416, filed on Apr. 24, 2012, provisional application No. 61/651,221, filed on May 24, 2012, provisional application No. 61/653,778, filed on May 31, 2012, provisional application No. 61/670,895, filed on Jul. 12, 2012, provisional application No. 61/717,351, filed on Oct. 23, 2012.

(51) Int. Cl.
*C07D 401/14* (2006.01)
*A61K 31/496* (2006.01)
*C07D 405/12* (2006.01)

(52) U.S. Cl.
CPC .................................. *C07D 405/12* (2013.01)

(58) Field of Classification Search
None
See application file for complete search history.

(56) References Cited

U.S. PATENT DOCUMENTS

2004/0147528 A1* 7/2004 Bathe et al. ............. 514/254.09

FOREIGN PATENT DOCUMENTS

WO    WO 02/102794    12/2002

OTHER PUBLICATIONS

Caira "Crystalline Polymorphism of Organic Compounds", Department of Chemistry, University of Cape Town, vol. 198, Jan. 1, 1998, pp. 163-208.
Bernstein "Polymorphism in Molecular Crystals", IUCr Monographs on Crystallography, Oxford Sciences Publications, 2002, p. 9.

* cited by examiner

*Primary Examiner* — Marcos Sznaidman
*Assistant Examiner* — Rayna B Rodriguez
(74) *Attorney, Agent, or Firm* — Baker & Hostetler LLP

(57) ABSTRACT

The present invention provides solid state forms of Vilazodone and Vilazodone hydrochloride, processes for preparing these solid state forms, and pharmaceutical compositions comprising one or more of these solid state forms.

14 Claims, 40 Drawing Sheets

XRPD of Form A

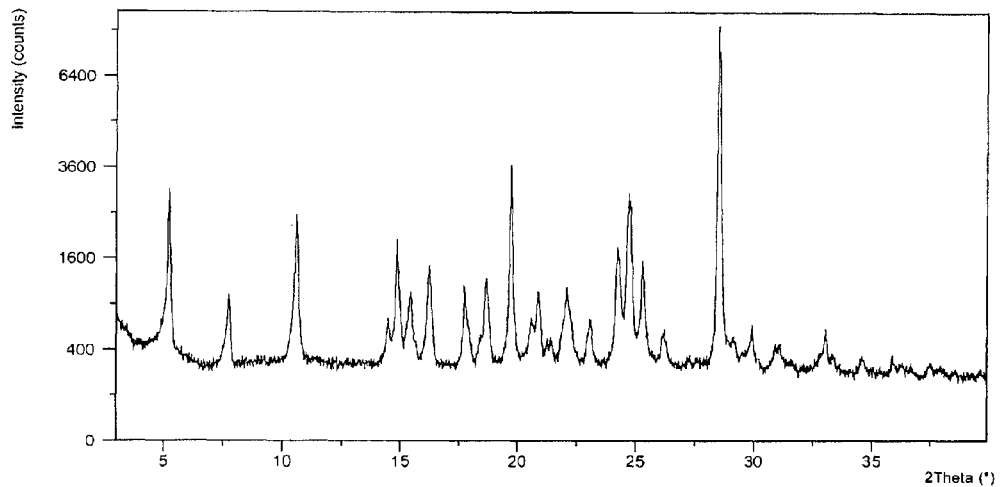
Figure 1. XRPD of Form A
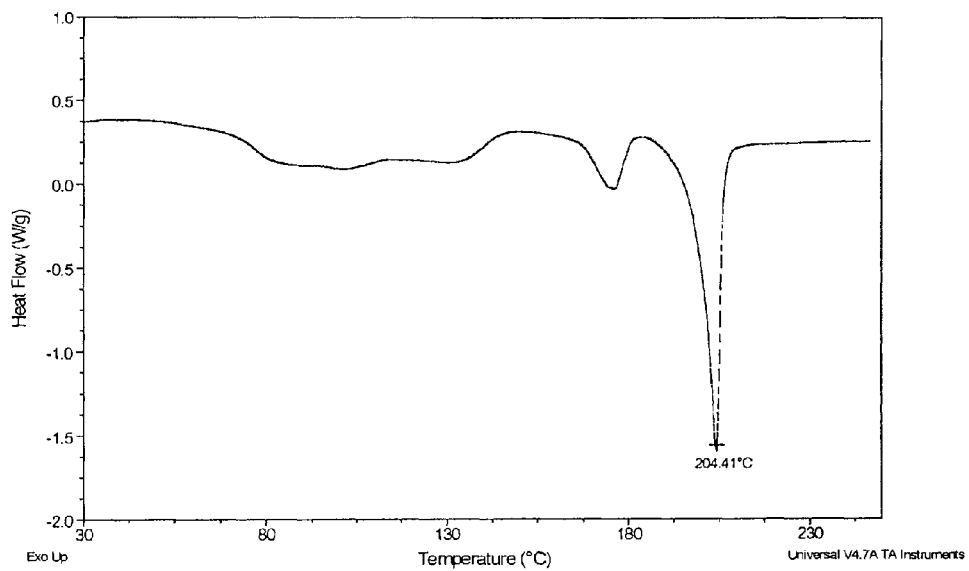
Figure 2. DSC of Form A (DSS-1473-8-w2)

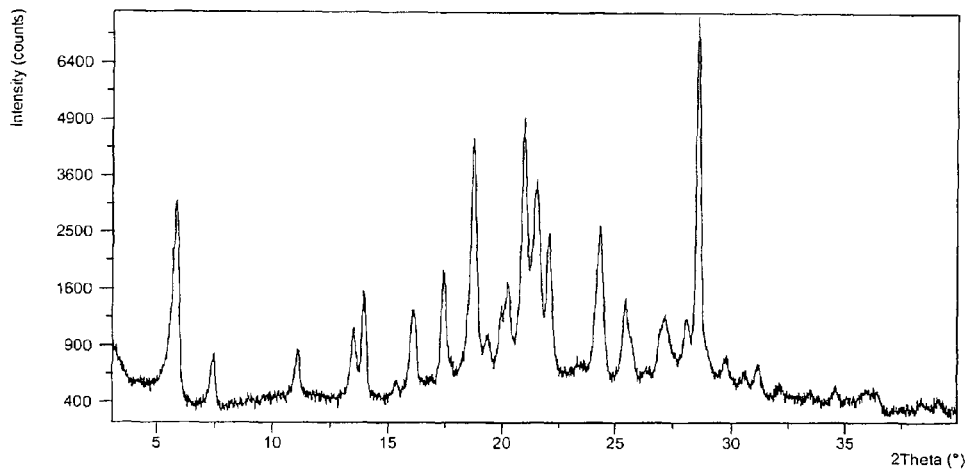
Figure 3. XRPD of Form B
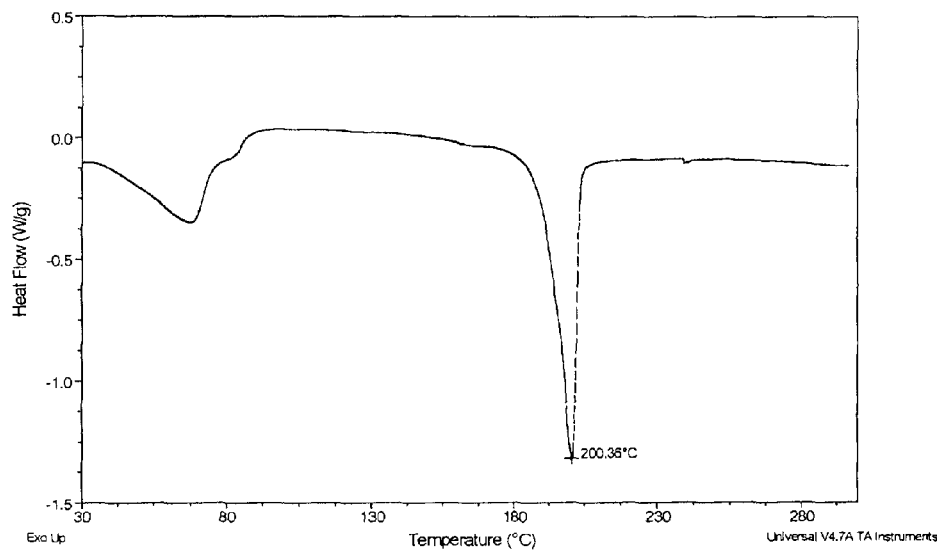
Figure 4. DSC of Form B

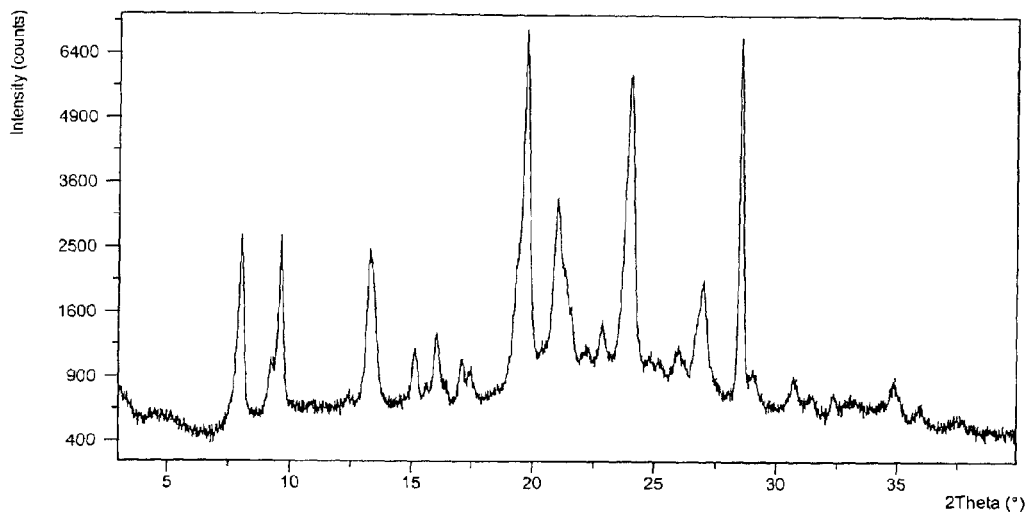
Figure 5. XRPD of Form C
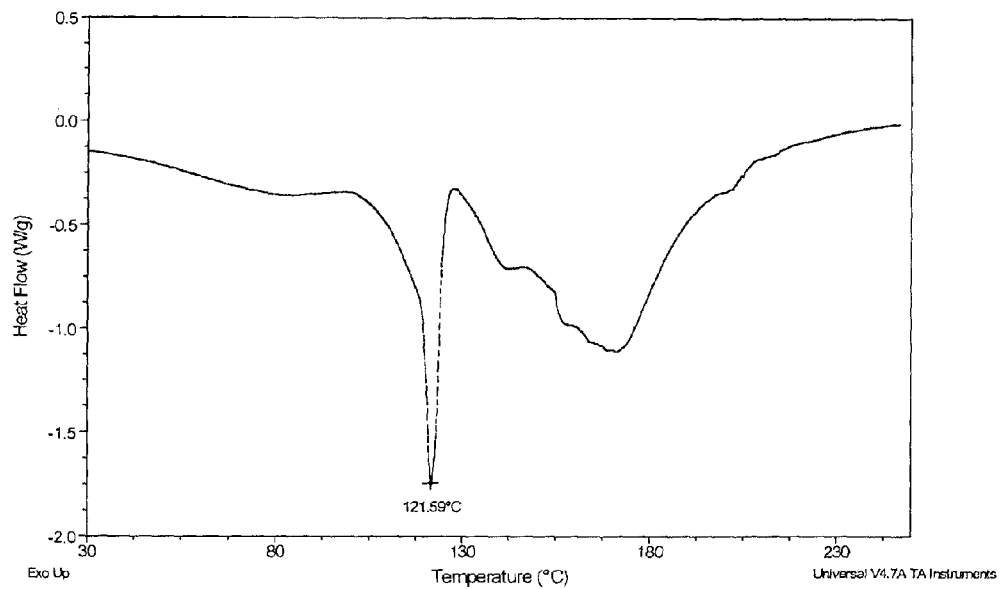
Figure 6. DSC of Form C

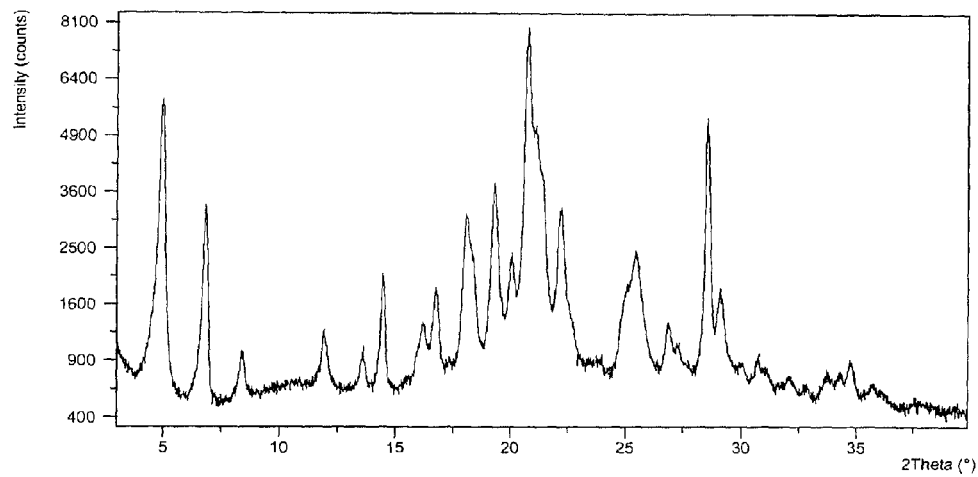
Figure 7. XRPD of Form D
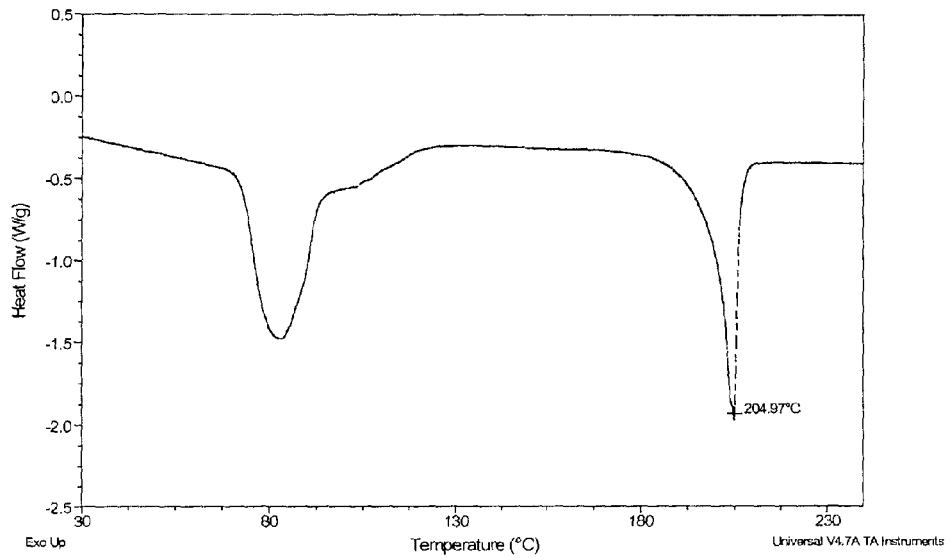
Figure 8. DSC of Form D

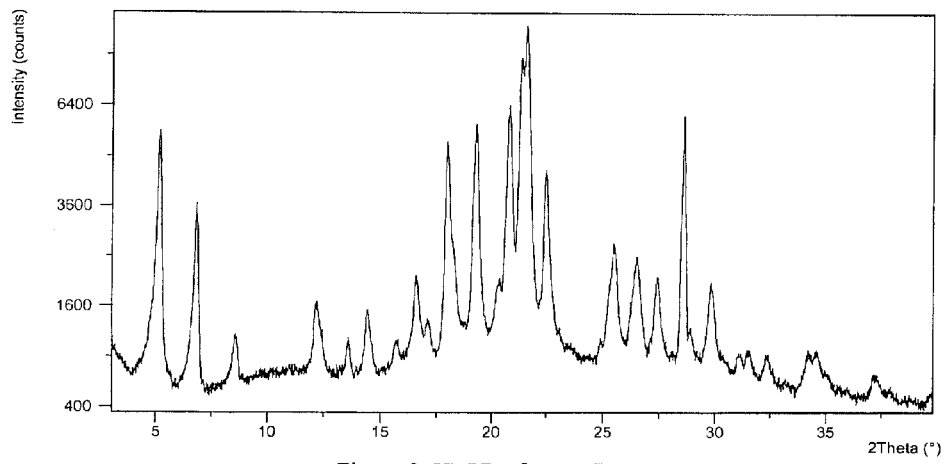
Figure 9. XRPD of Form E
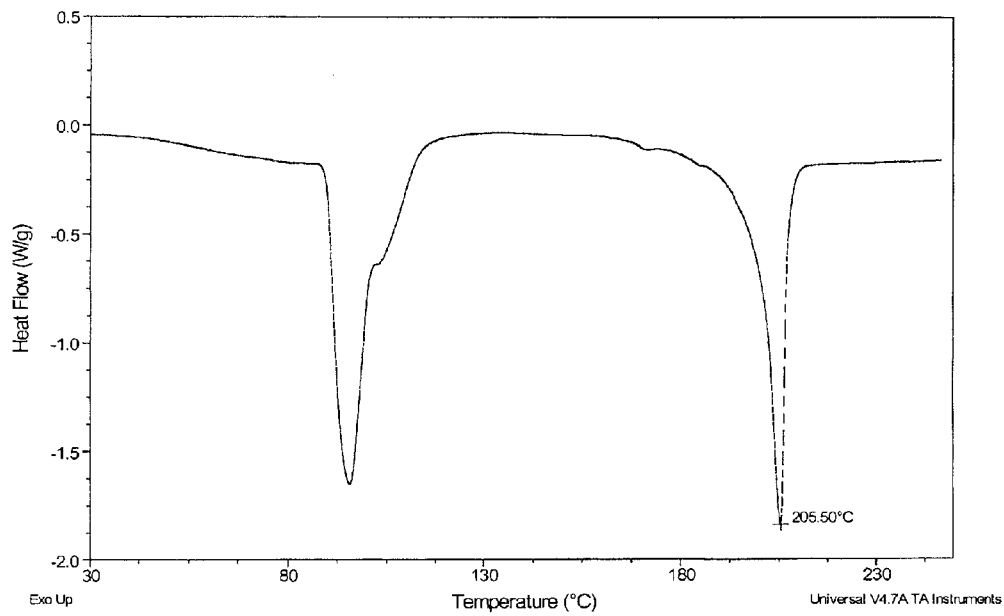
Figure 10. DSC of Form E

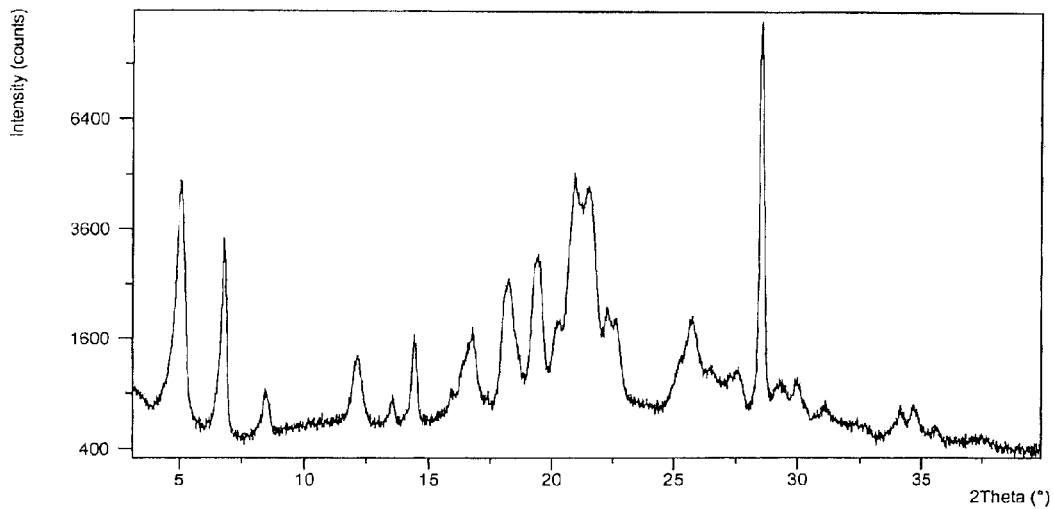
Figure 11. XRPD of Form F
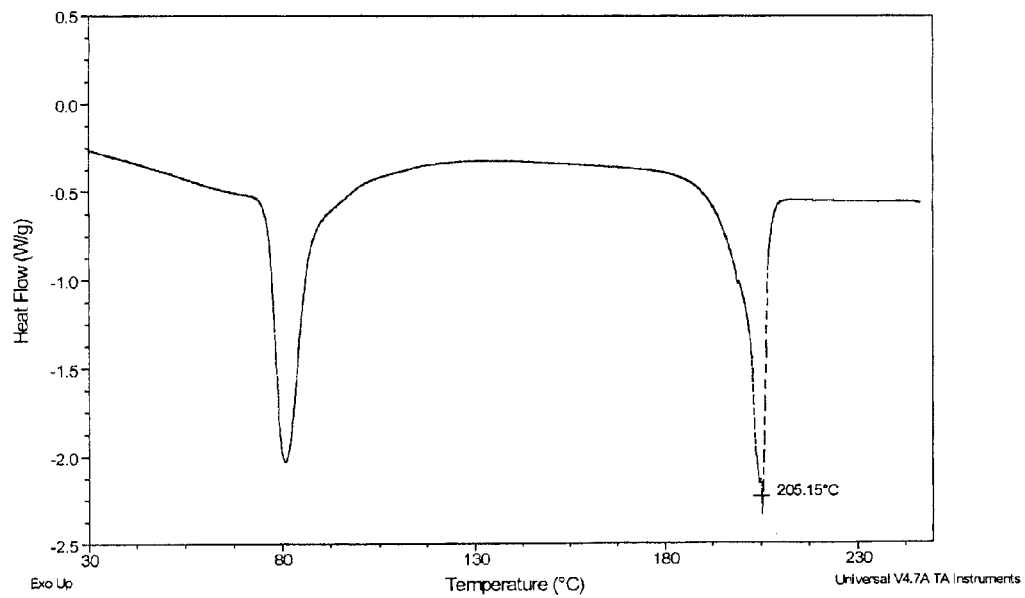
Figure 12. DSC of Form F

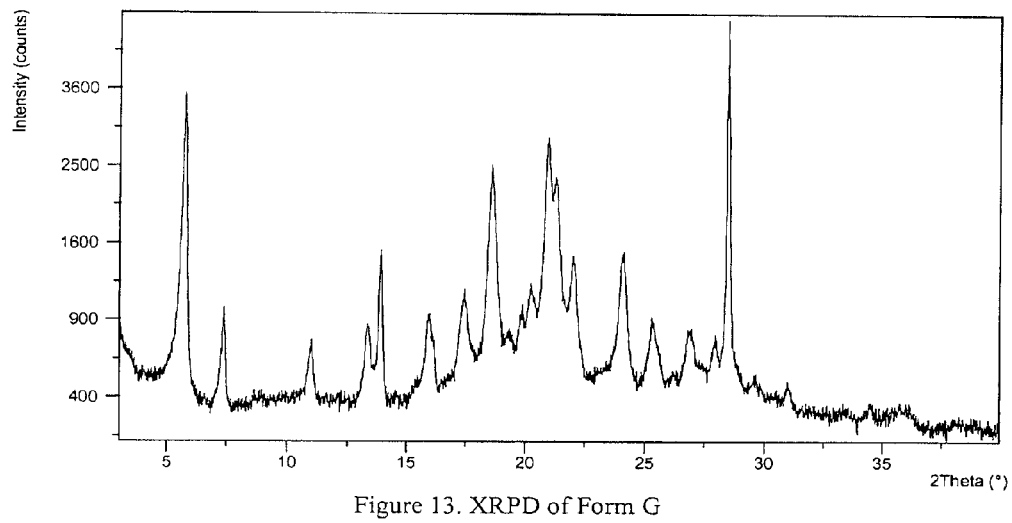
Figure 13. XRPD of Form G
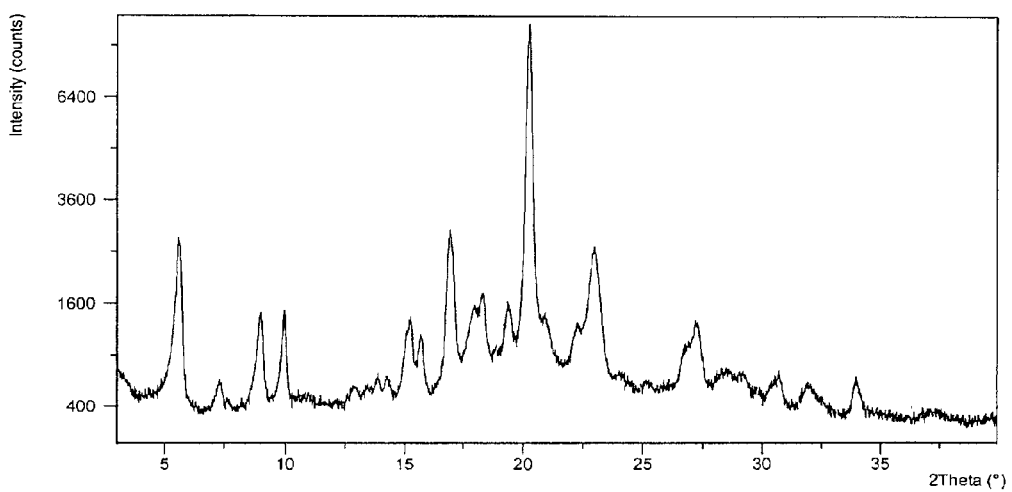
Figure 14. XRPD of Form H

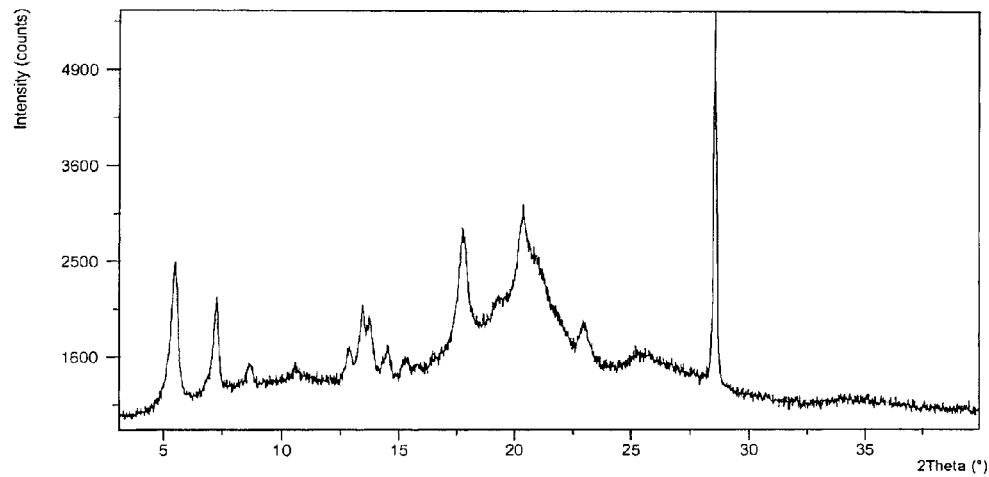
Figure 15. XRPD of Form I
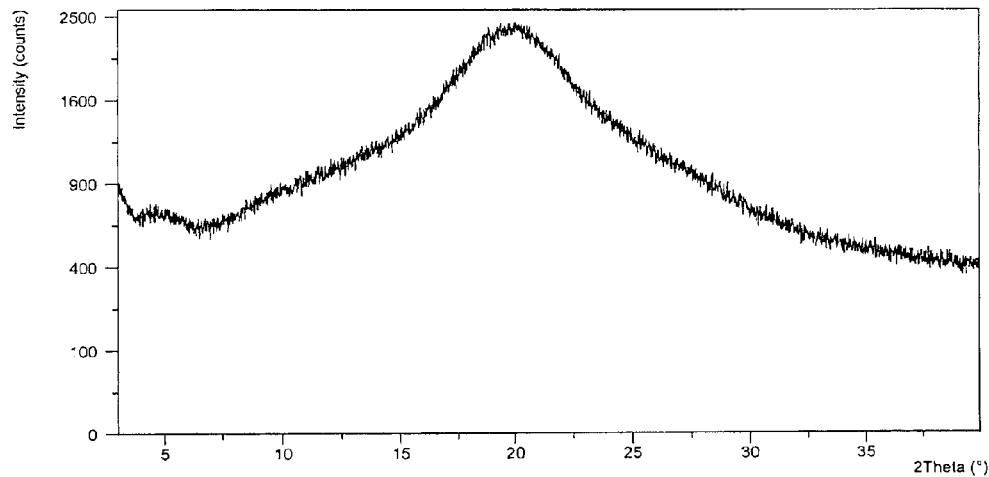
Figure 16. XRPD of amorphous vilazodone

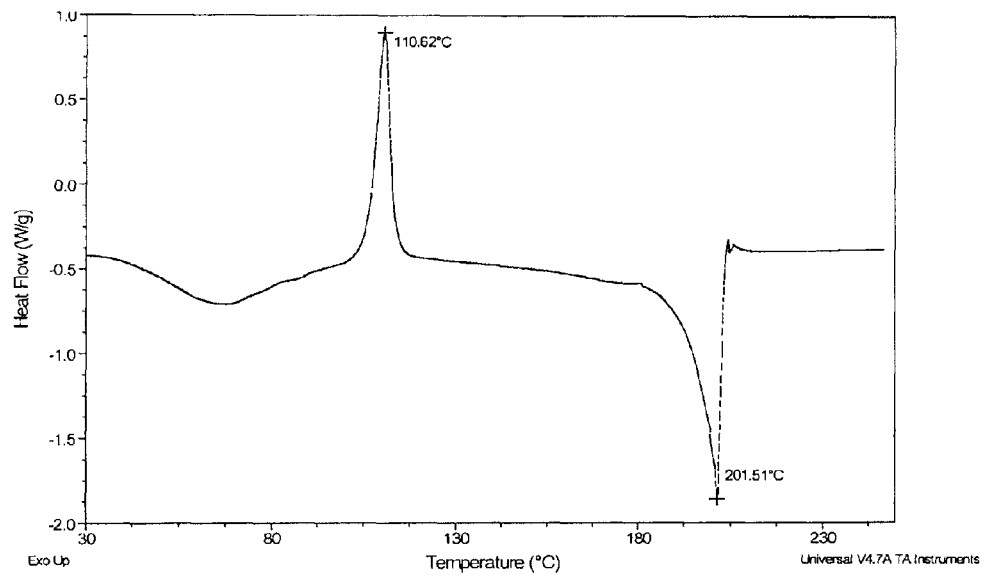
Figure 17. DSC of amorphous vilazodone
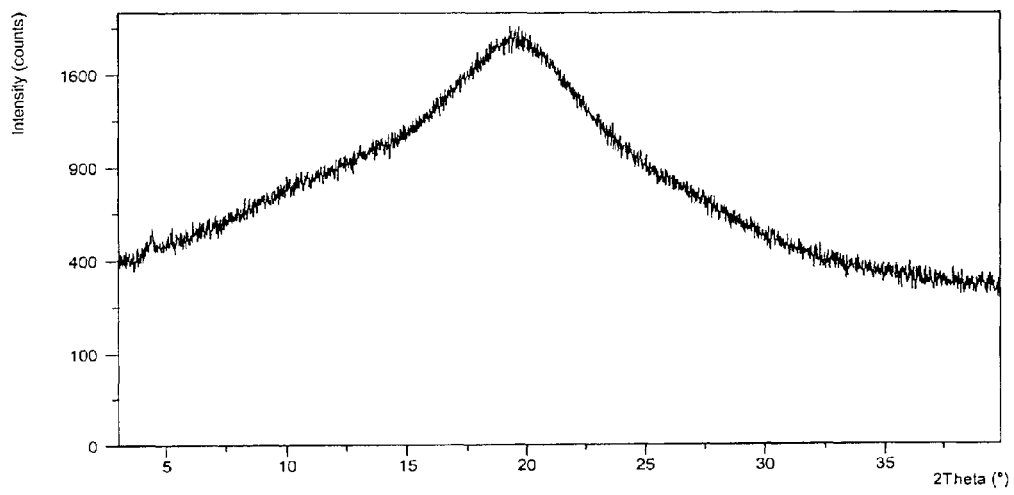
Figure 18. XRPD of Vilazodone (obtained by spray drying)

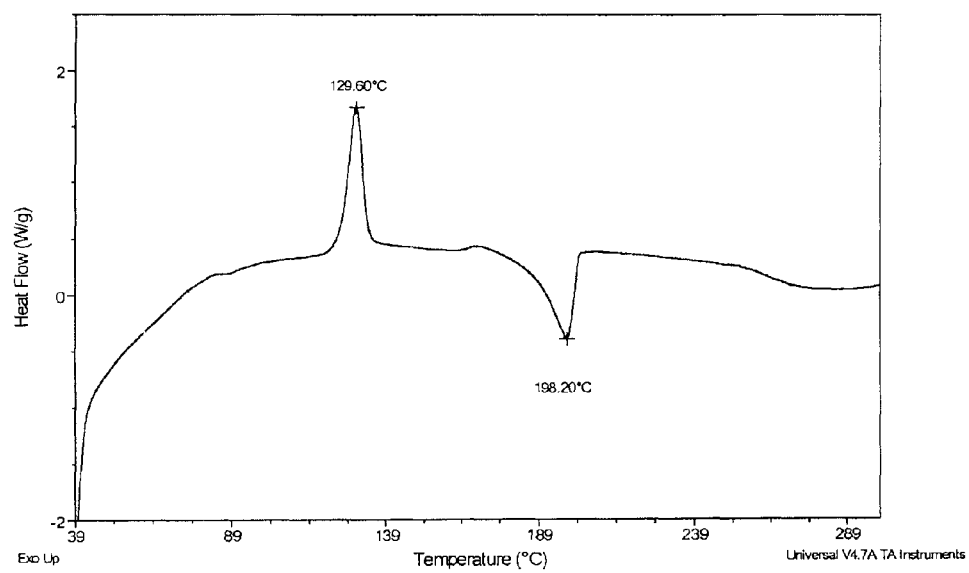
Figure 19. DSC of Vilazodone (obtained by spray drying)
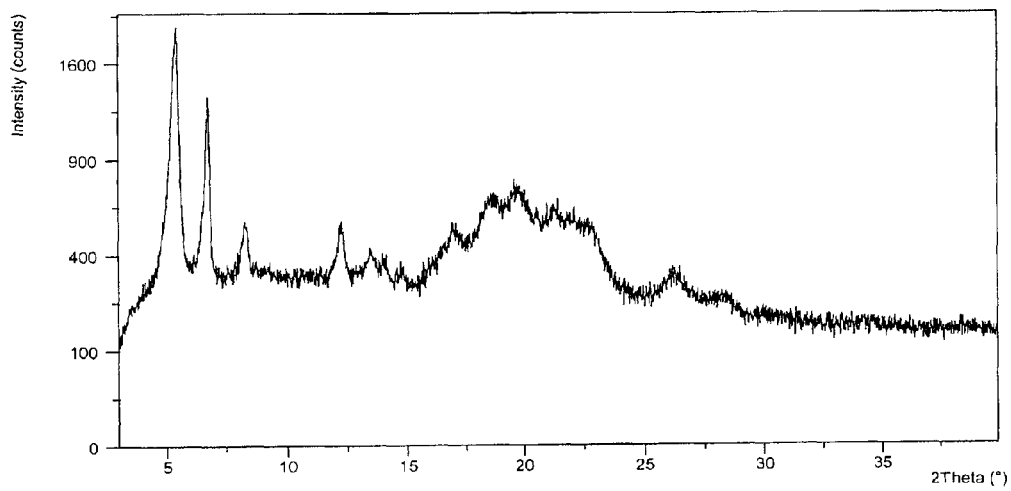
Figure 20. XRPD of Vilazodone Form E1

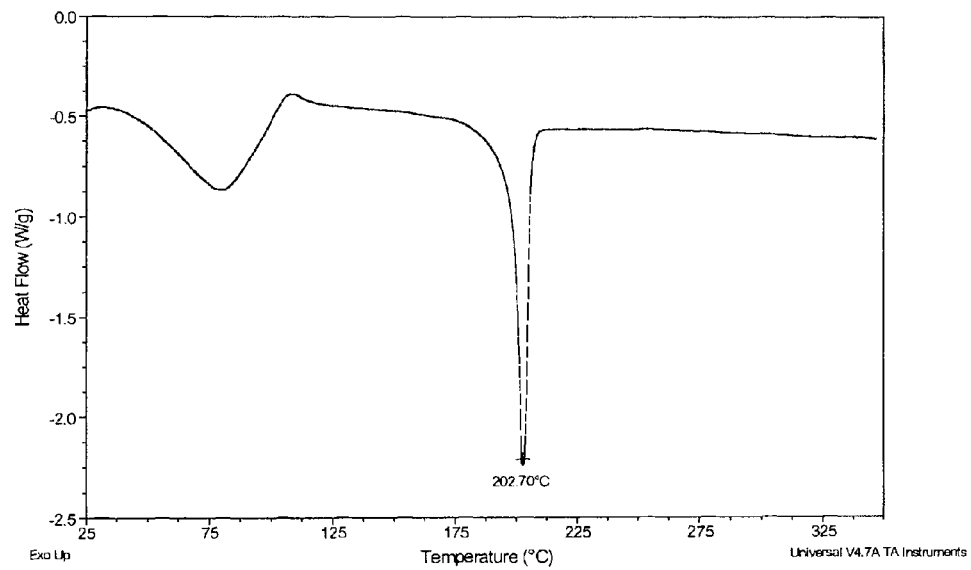
Figure 21. DSC of Vilazodone base Form E1
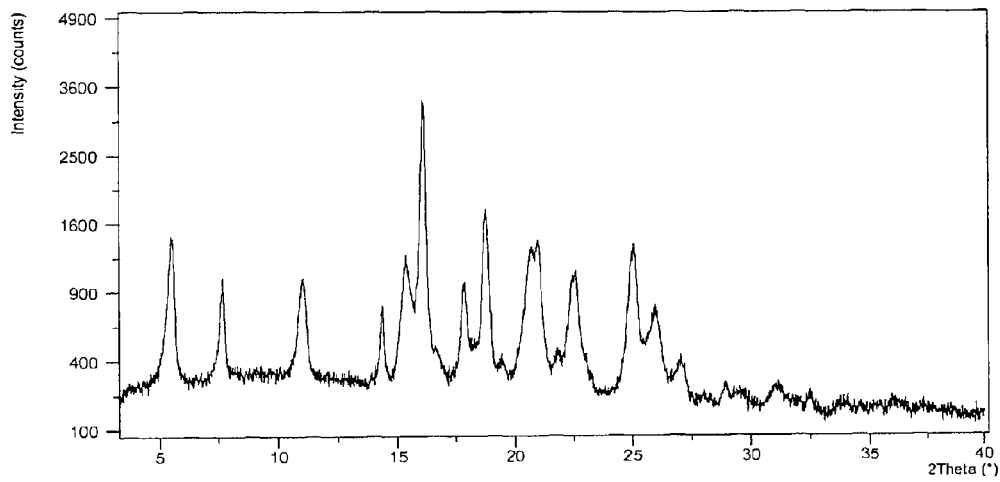
Figure 22. XRPD of Vilazodone Form A1

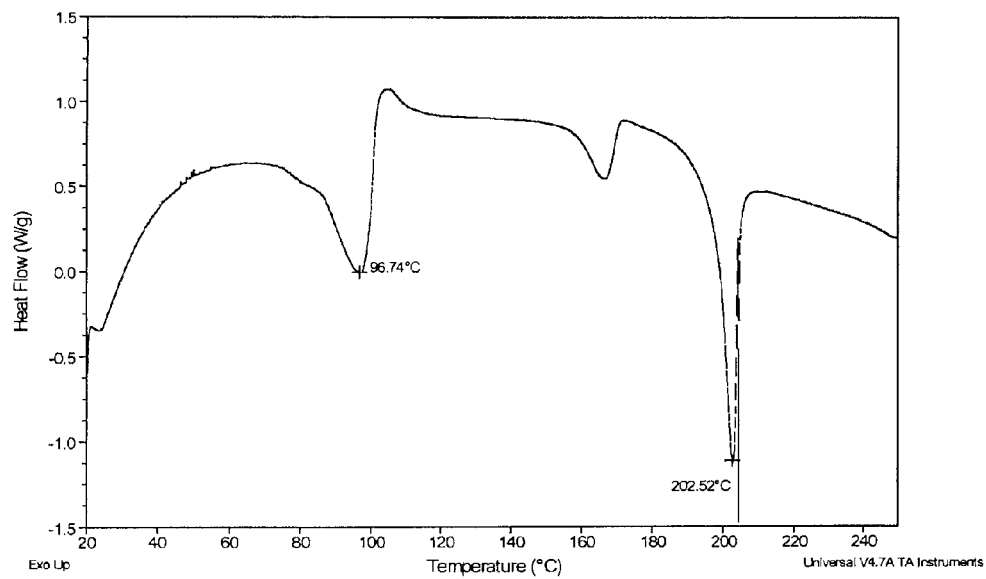
Figure 23. DSC of Vilazodone base Form A1
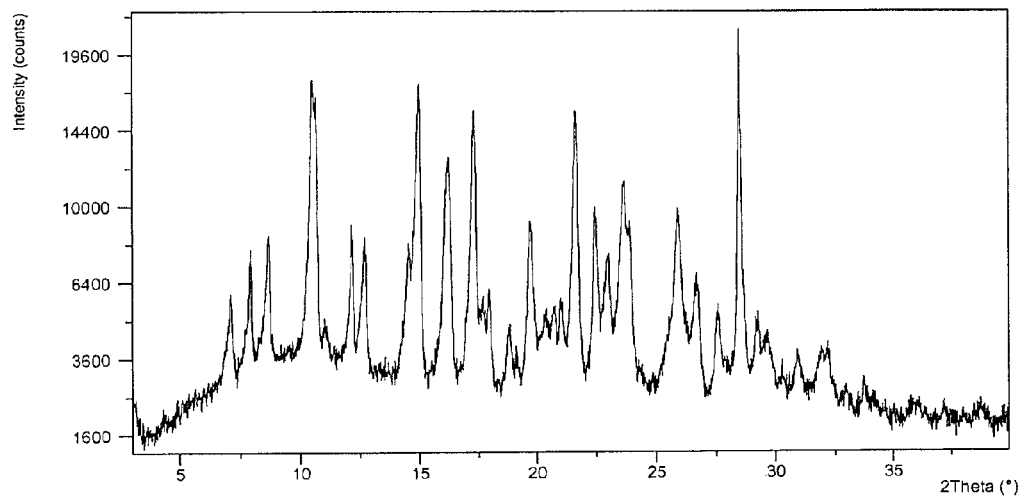
Figure 24. XRPD of Vilazodone HCl Form Alpha

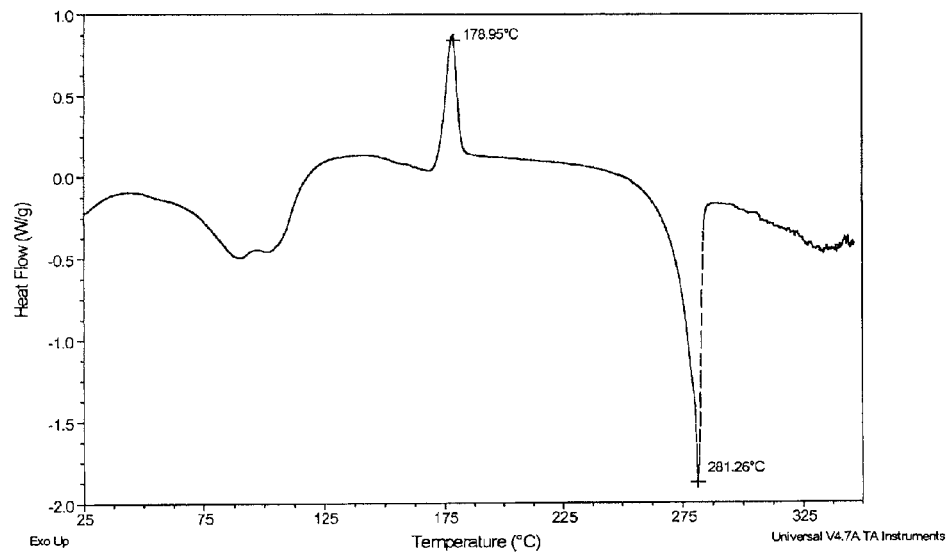
Figure 25. DSC of Vilazodone HCl Form Alpha
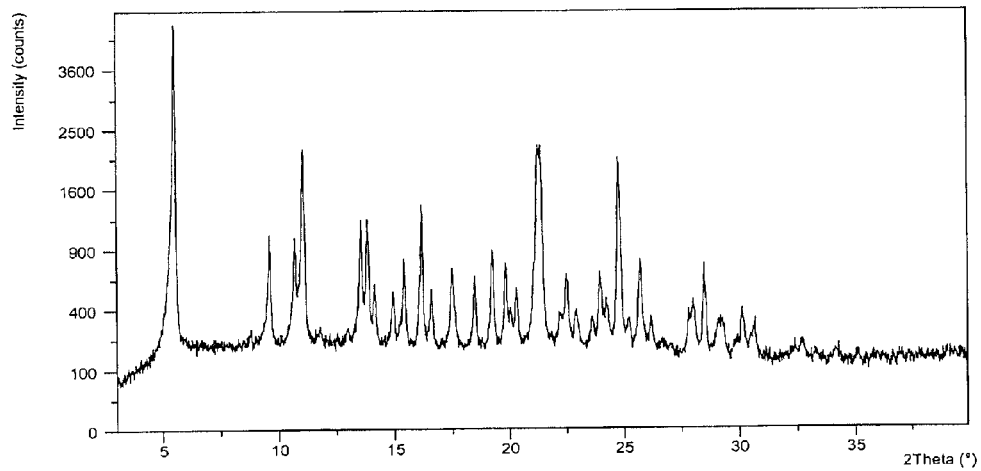
Figure 26. XRPD of Vilazodone HCl Form Beta

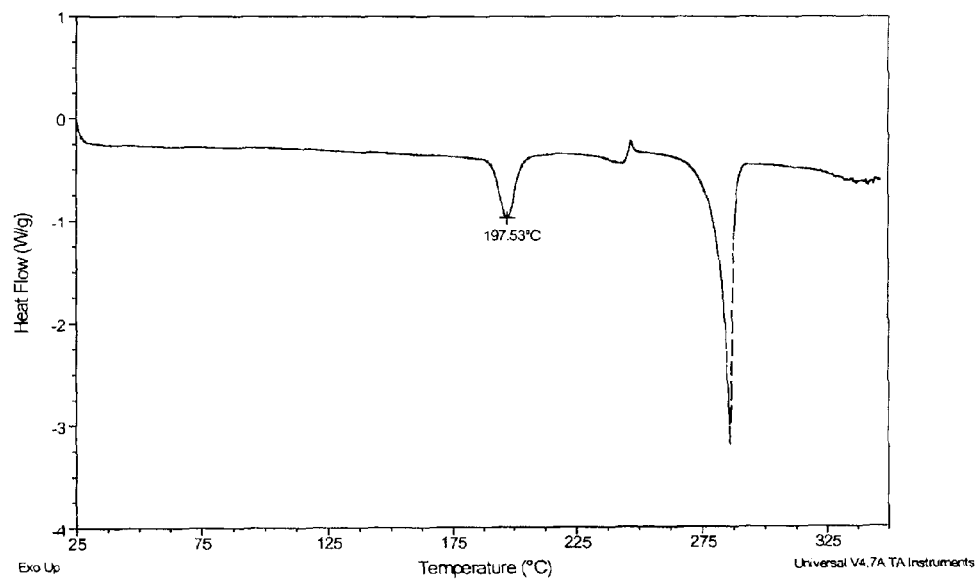
Figure 27. DSC of Vilazodone HCl Form Beta
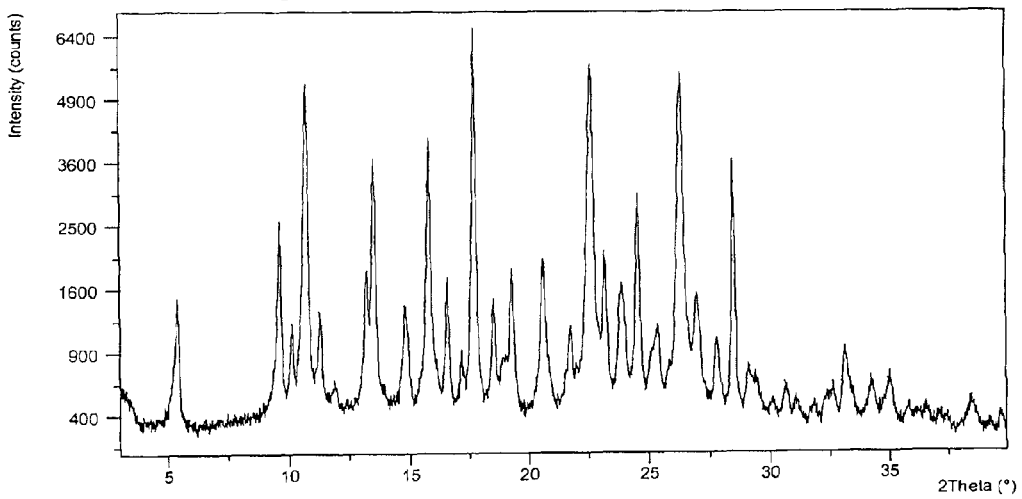
Figure 28. XRPD of Vilazodone HCl Form Gamma

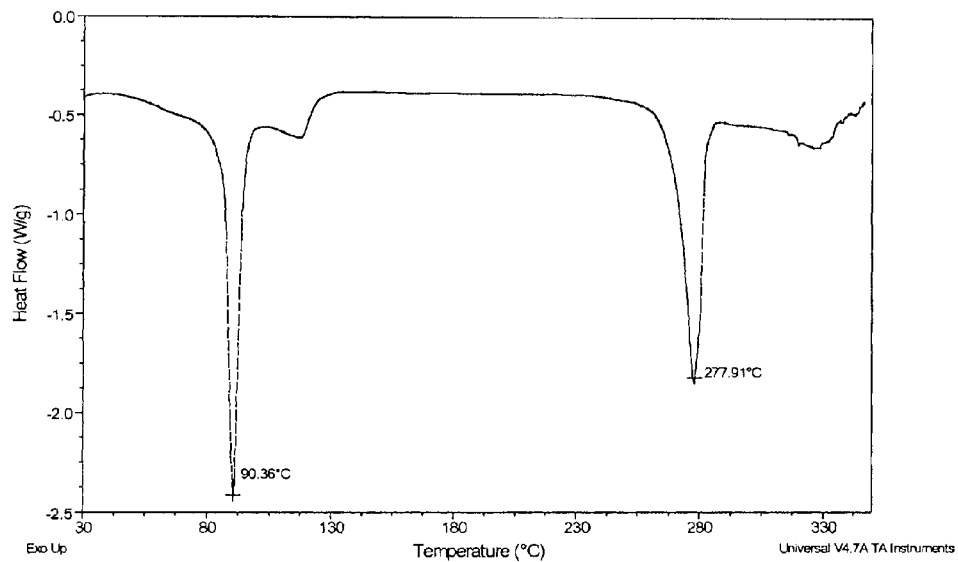
Figure 29. DSC of Vilazodone HCl Form Gamma
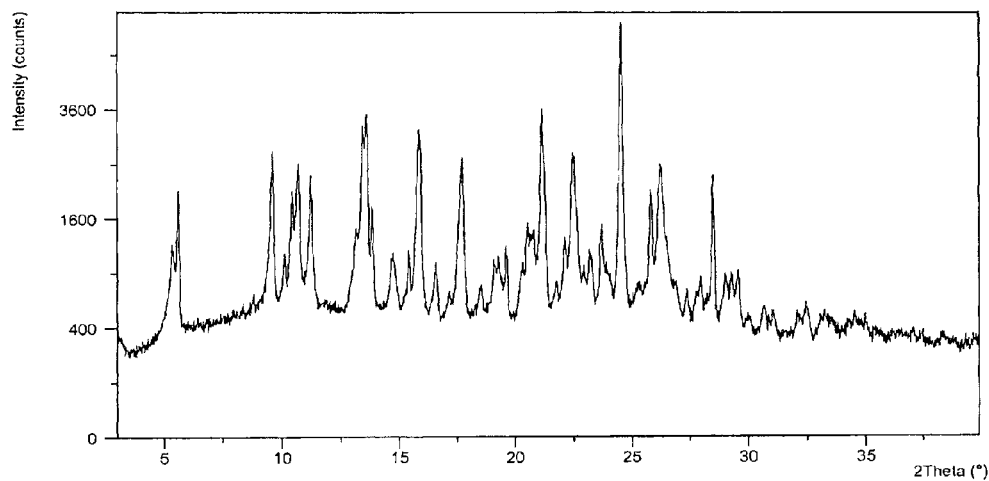
Figure 30. XRPD of Vilazodone HCl Form Delta

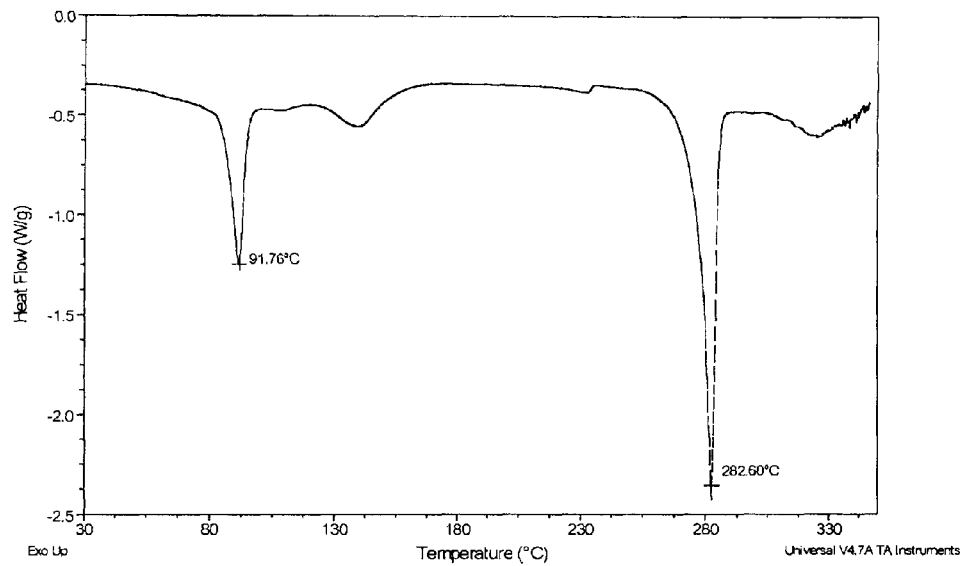
Figure 31. DSC of Vilazodone HCl Form Delta
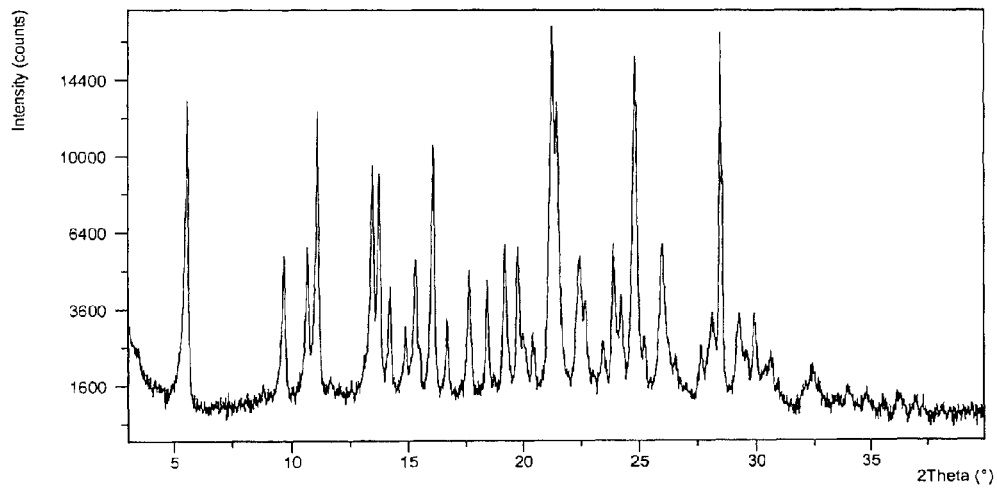
Figure 32. XRPD of Vilazodone HCl Form Epsilon

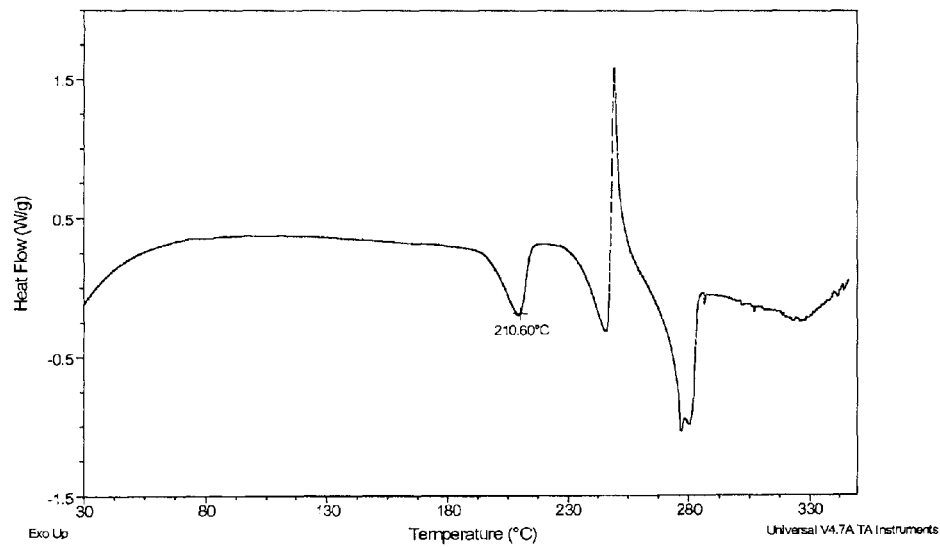
Figure 33. DSC of Vilazodone HCl Form Epsilon
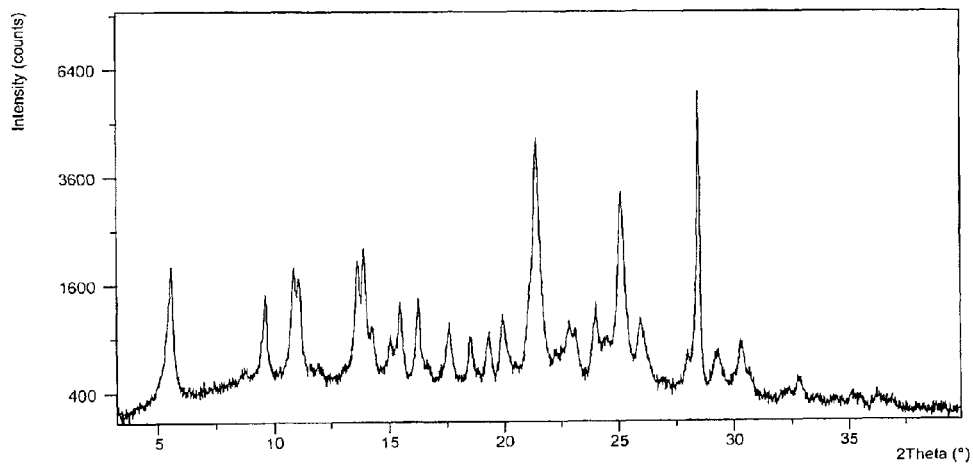
Figure 34. XRPD of Vilazodone HCl Form Eta

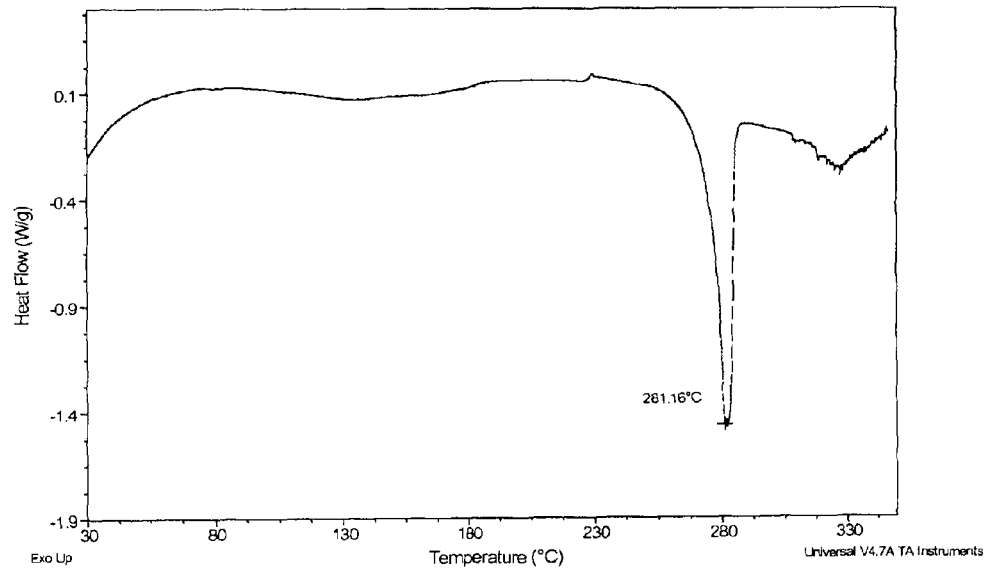
Figure 35. XRPD of Vilazodone HCl Form Eta
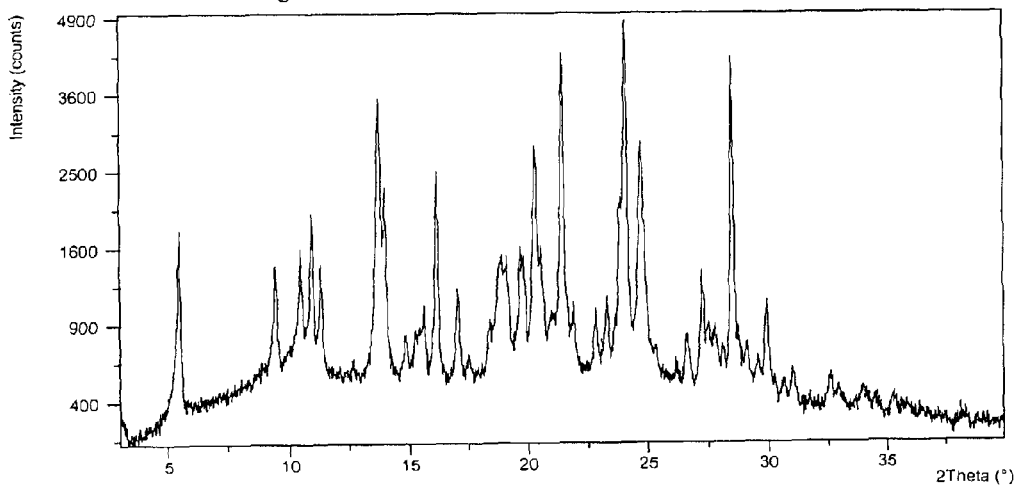
Figure 36. XRPD of Vilazodone HCl Form Theta

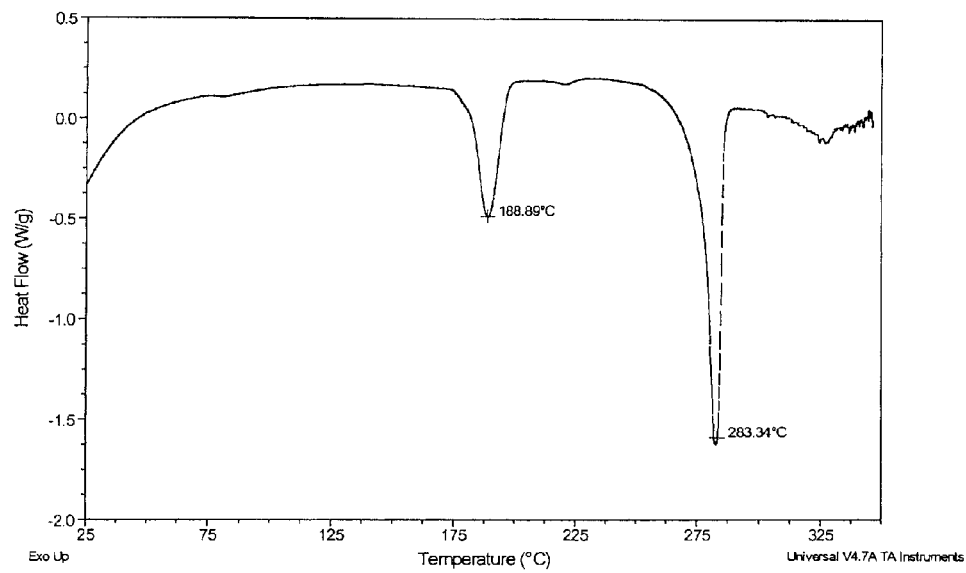
Figure 37. DSC of Vilazodone HCl Form Theta
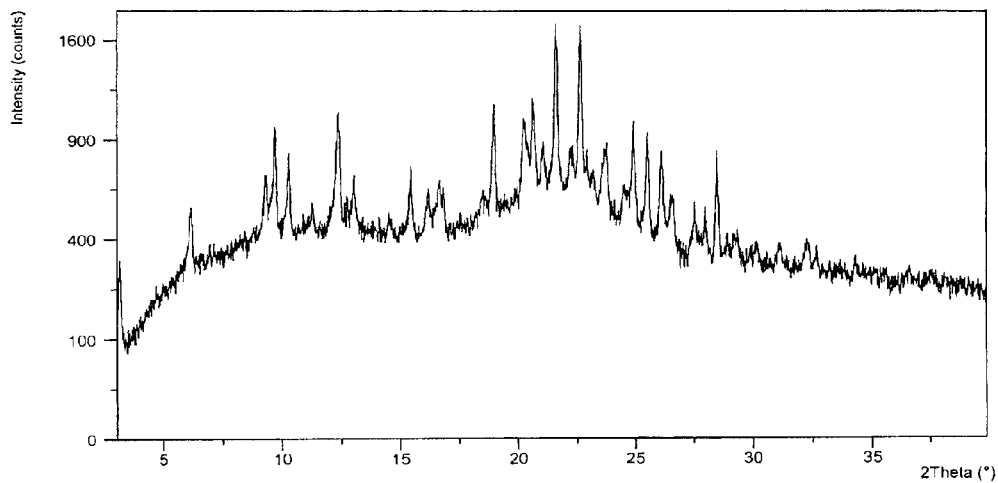
Figure 38. XRPD of Vilazodone HCl Form Iota

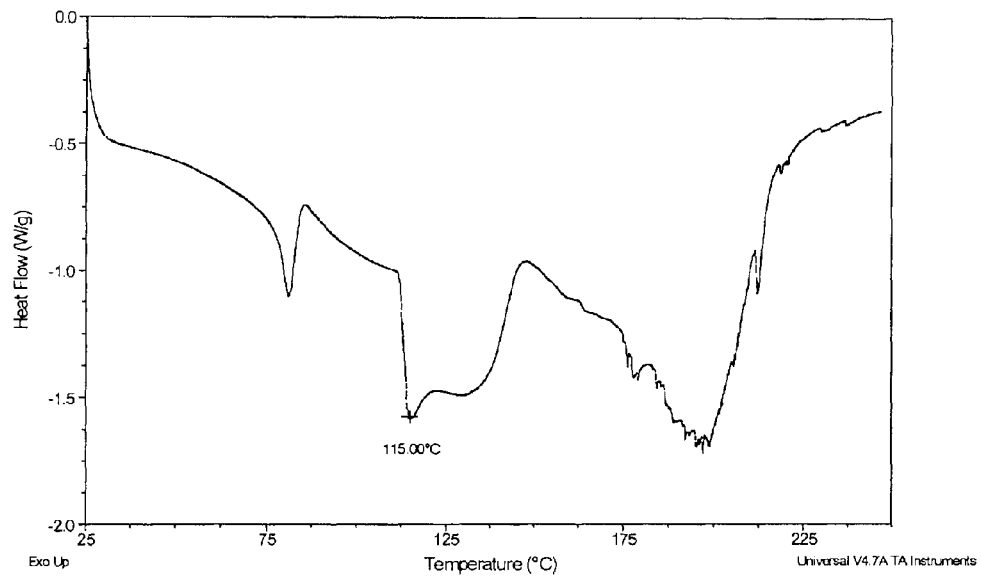
Figure 39. XRPD of Vilazodone HCl Form Iota
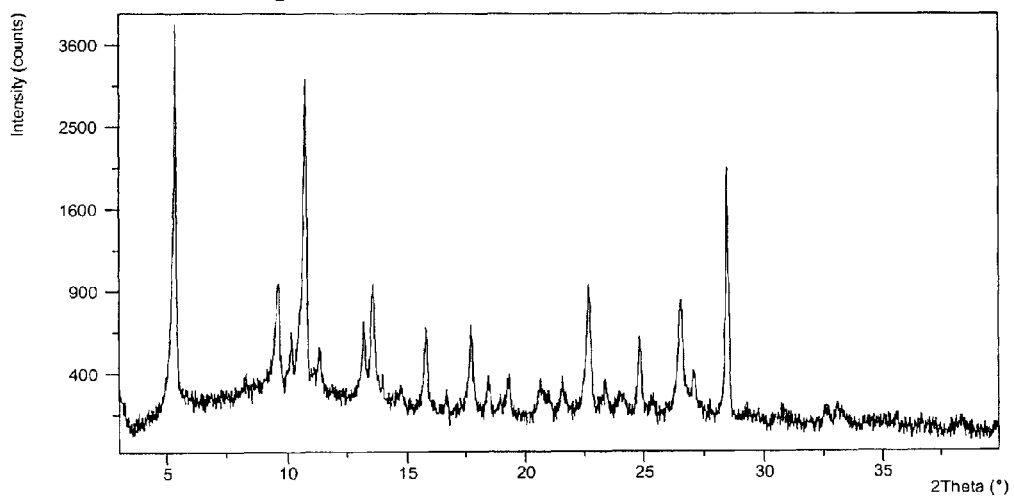
Figure 40. XRPD of Vilazodone HCl Form Kappa

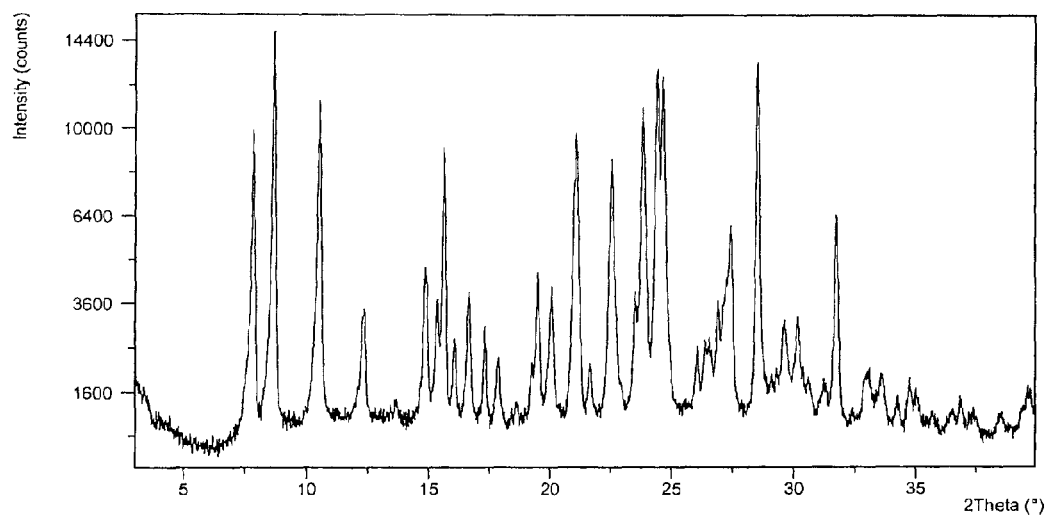
Figure 41. XRPD of Vilazodone HCl Form Lambda
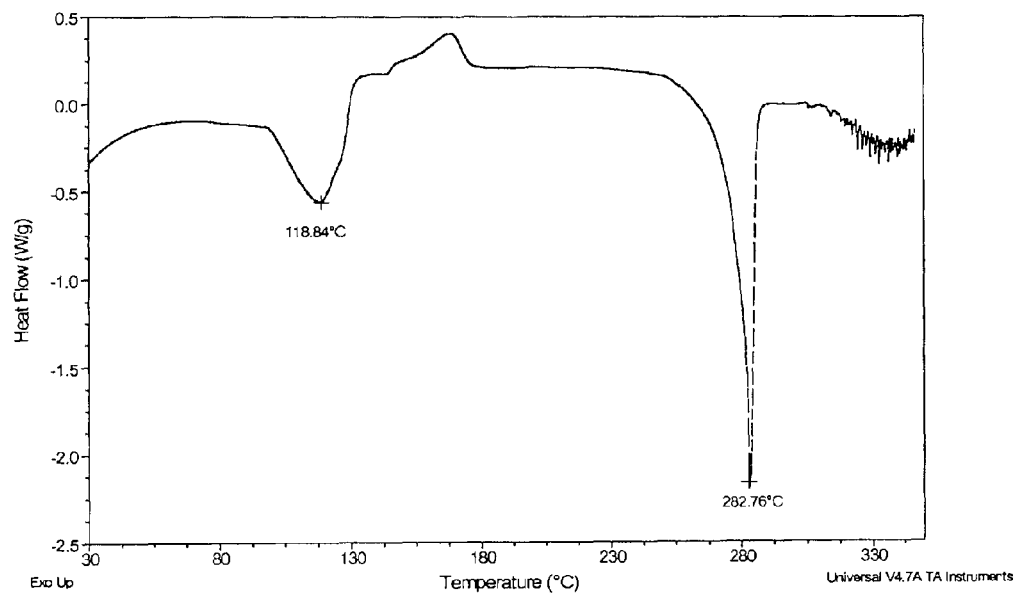
Figure 42. DSC of Vilazodone HCl Form Lambda

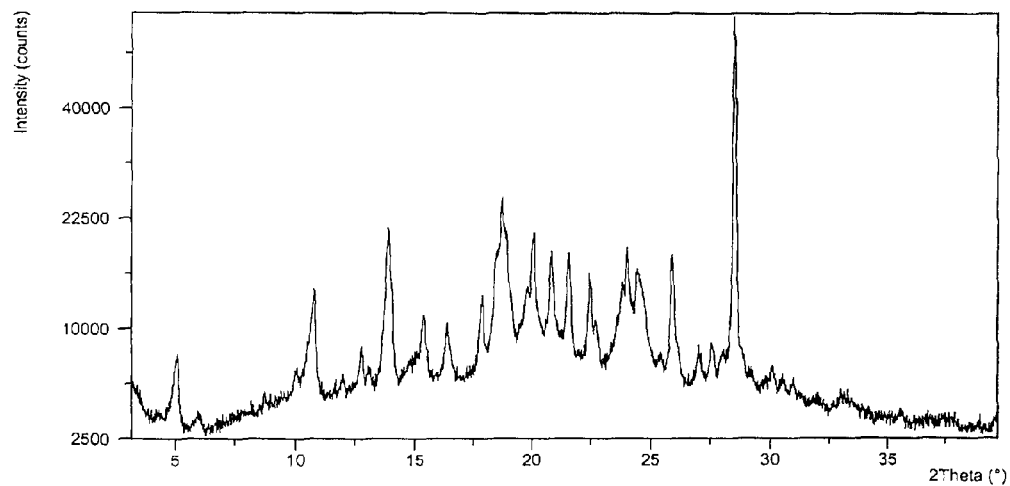
Figure 43. XRPD of Vilazodone HCl Form Mu
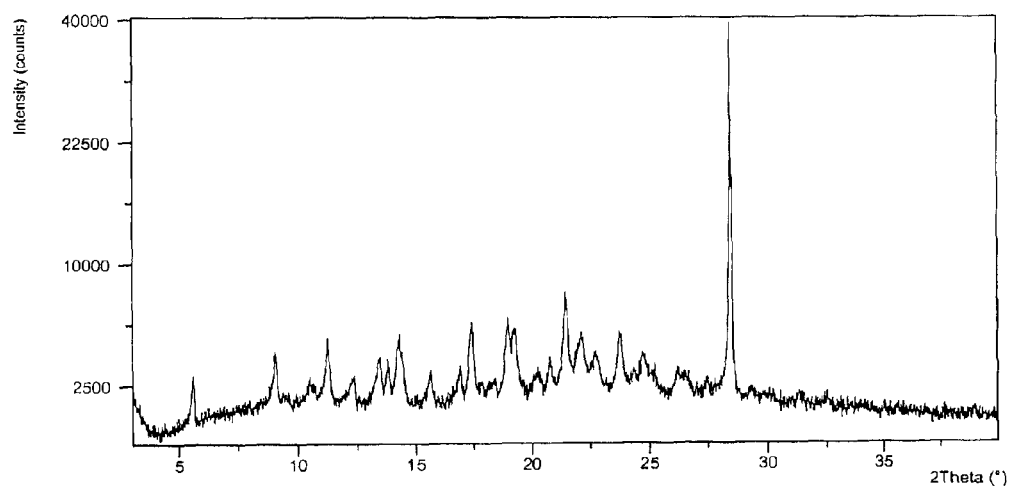
Figure 44. XRPD of Vilazodone HCl Form Nu

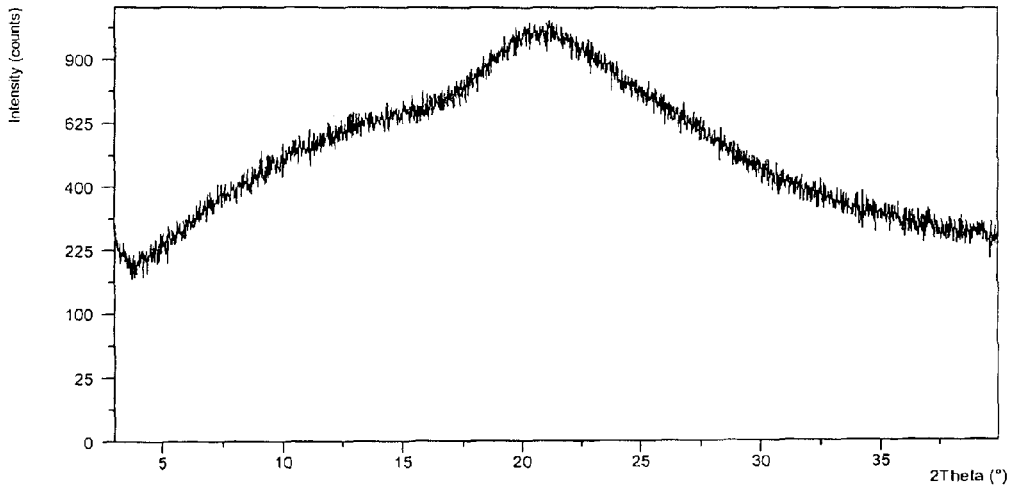
Figure 45. XRPD of Vilazodone HCl (obtained by spray drying)
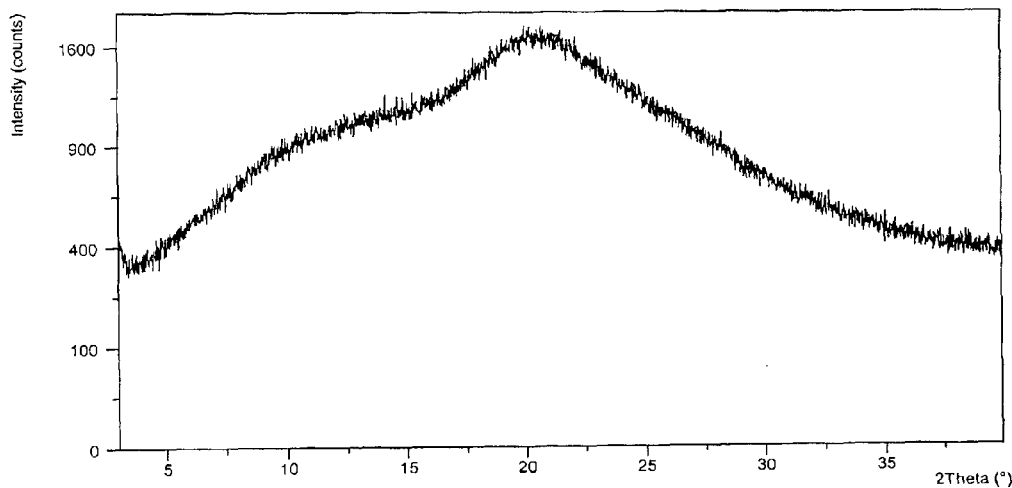
Figure 46. XRPD of Vilazodone HCl (obtained by solid state grinding)

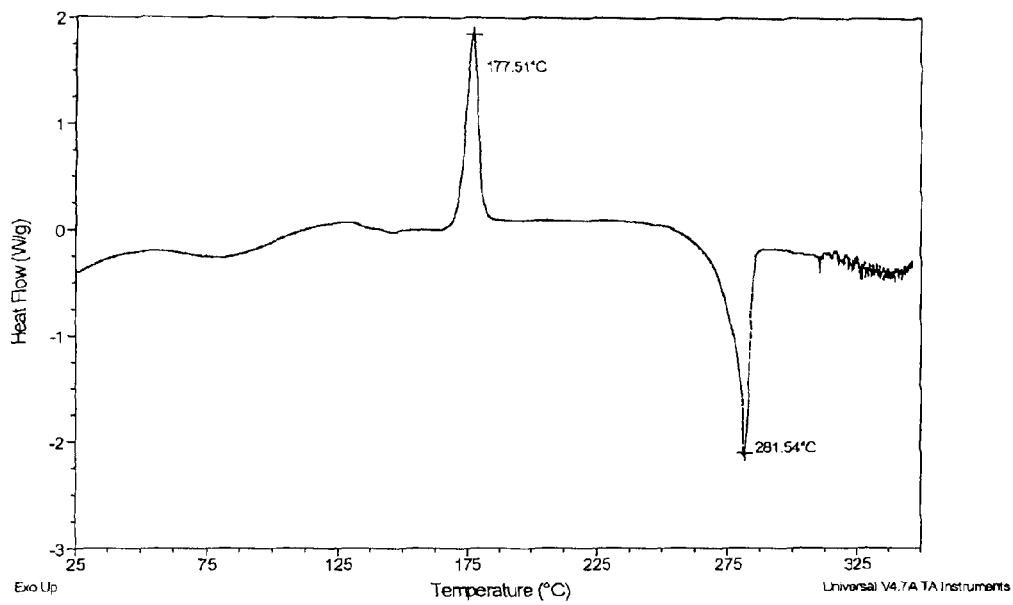
Figure 47. DSC of Vilazodone HCl (obtained by spray drying)
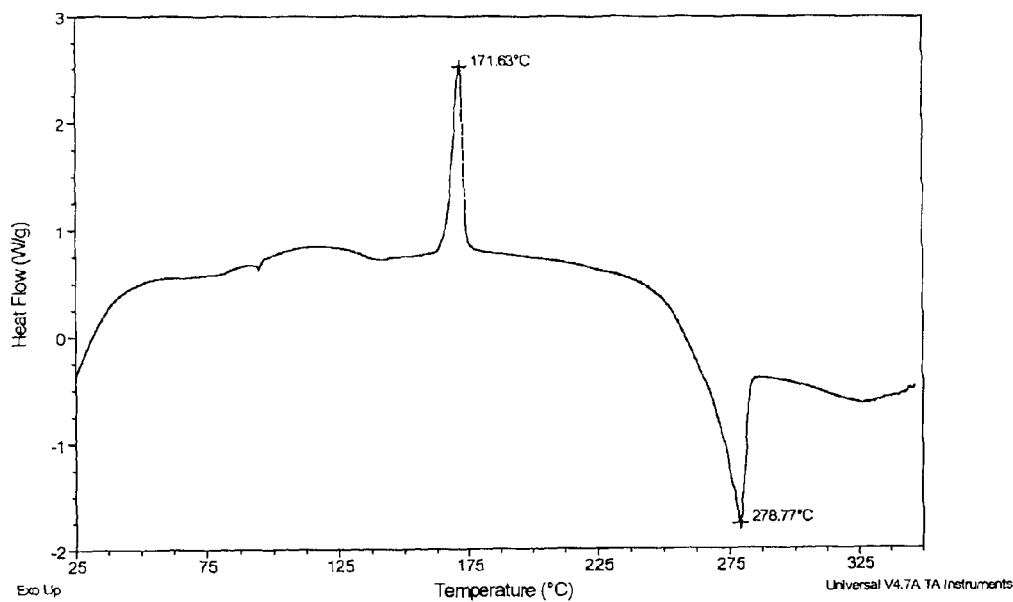
Figure 48. DSC of Vilazodone HCl (obtained by solid state grinding)

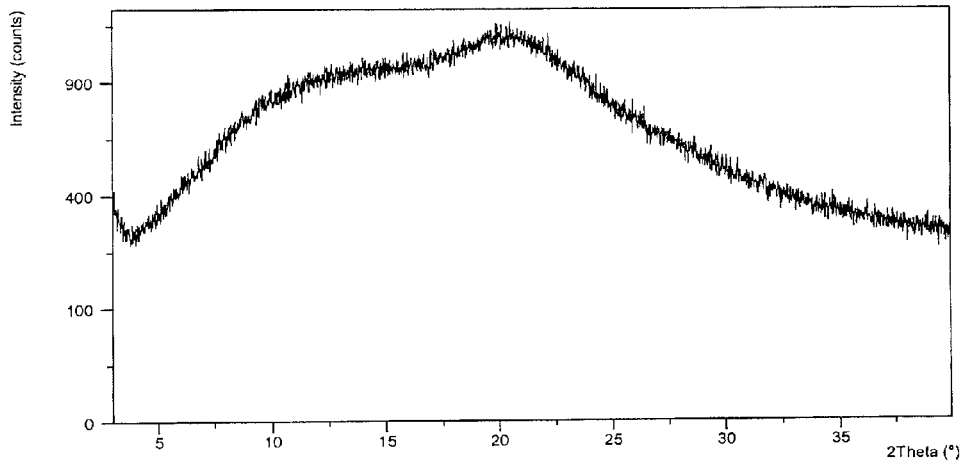
Figure 49. XRPD Vilazodone HCl solid dispersion with PVP (obtained by spray drying)
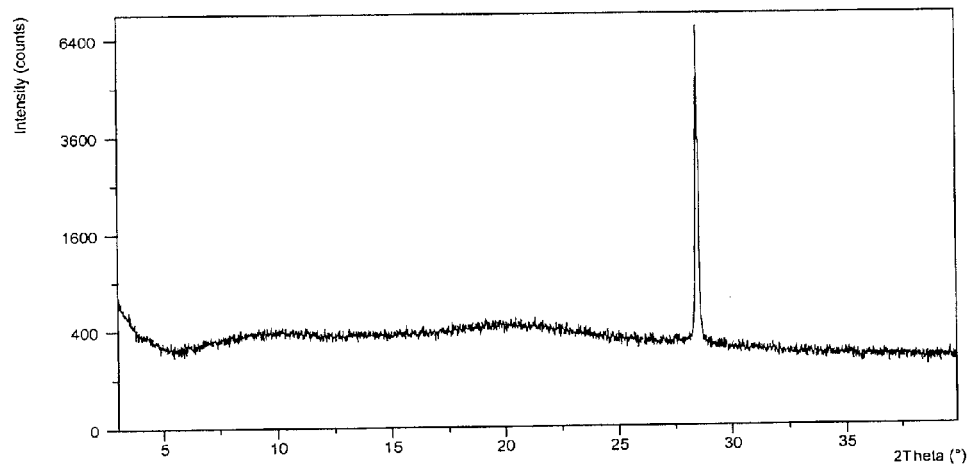
Figure 50. XRPD Vilazodone HCl solid dispersion with HPMC (obtained by spray drying) (Peak at 28.45 °2Θ corresponds to the silicon internal standard)

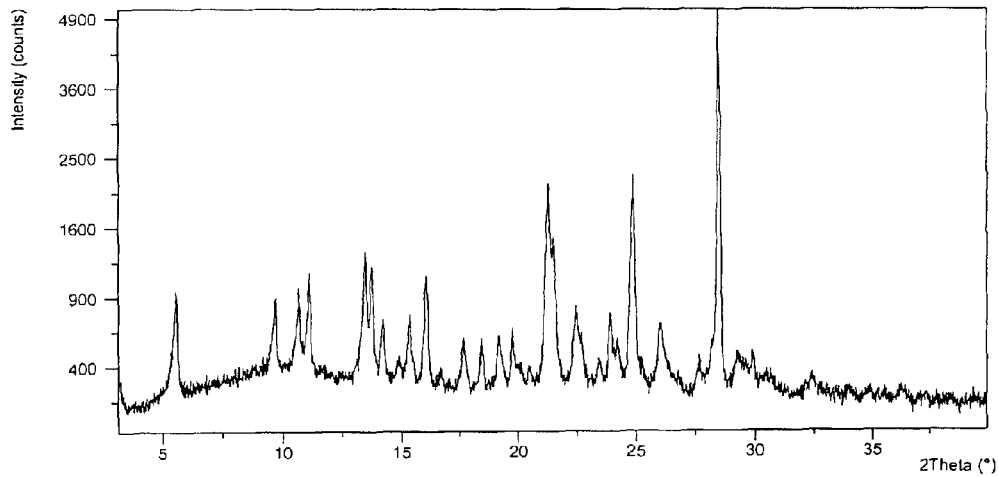
Fig 51. XRPD of Form Zeta (silicon added, no corrections performed)
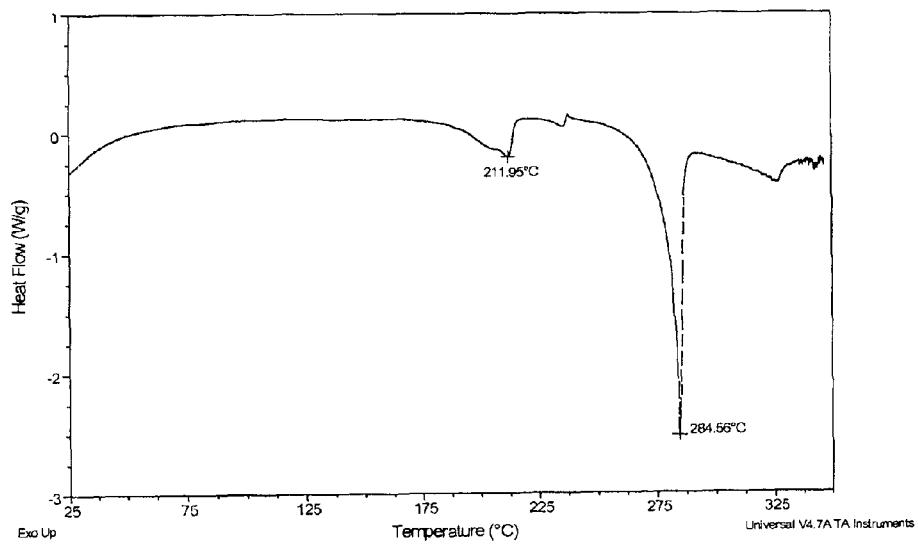
Fig 52. DSC of Form Zeta

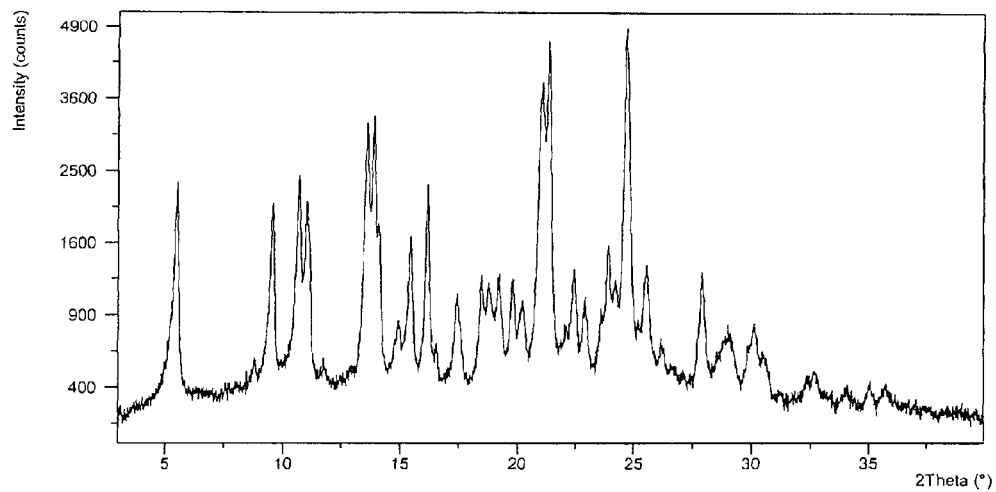
Figure 53. XRPD of Form Xi (silicon added, no corrections performed)
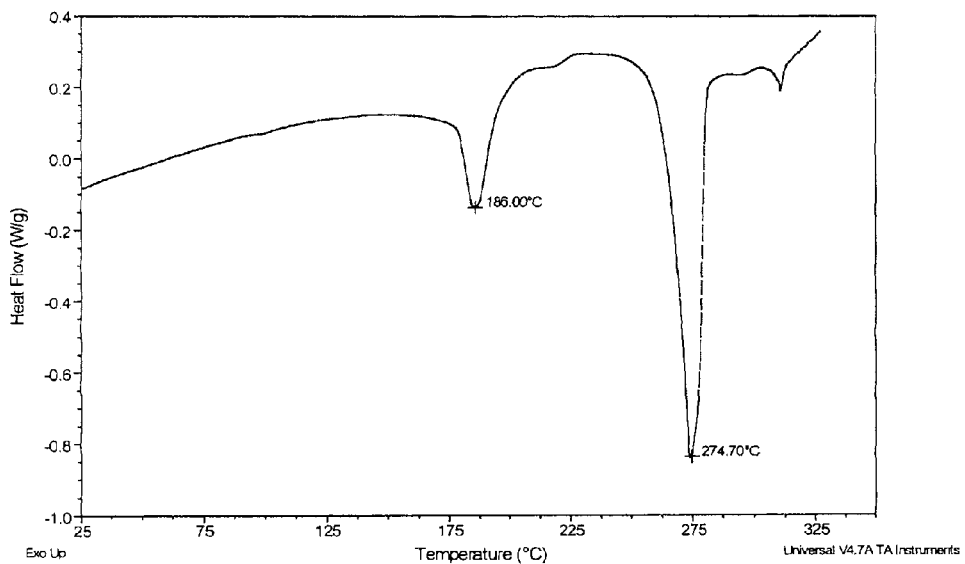
Figure 54. DSC of Form Xi

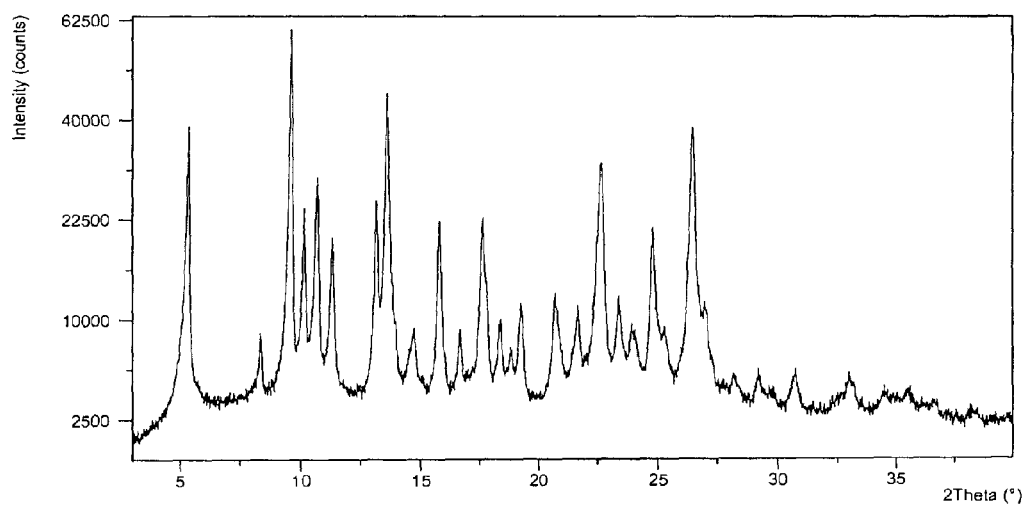
Fig 55. XRPD of Form Omicron (silicon added, no corrections performed)
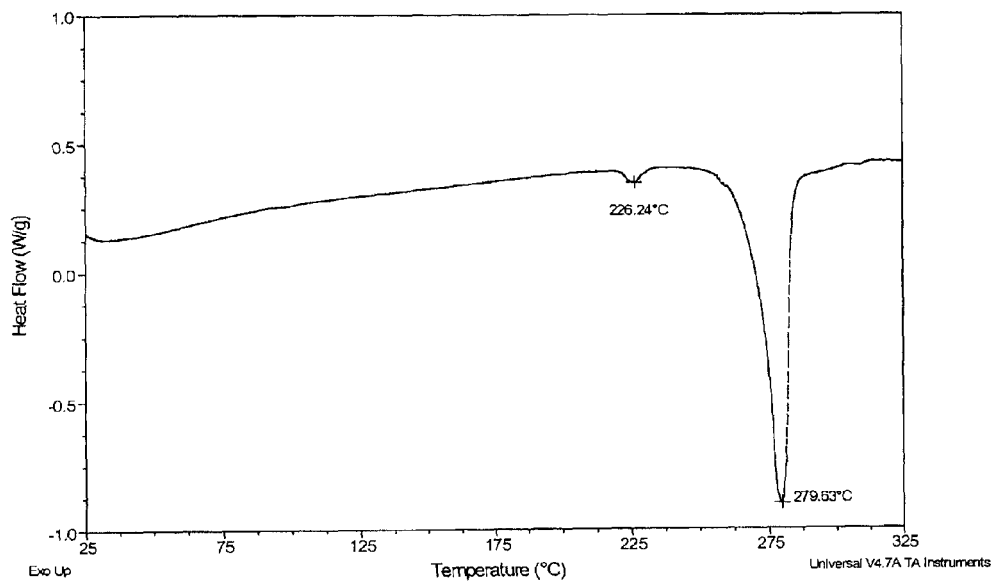
Fig 56. DSC of Form Omicron

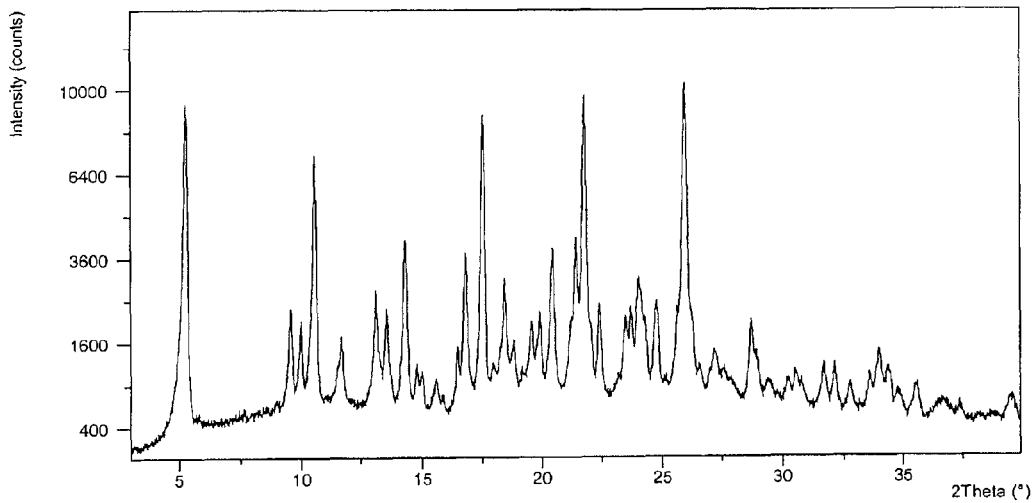
Fig 57. XRPD of Form Pi (silicon added, no corrections performed)
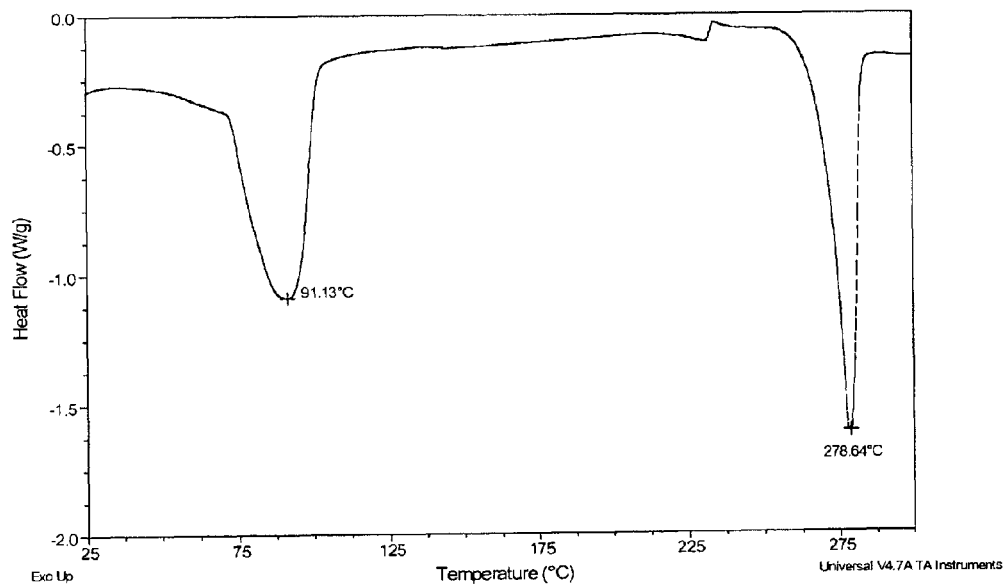
Fig 58. DSC of Form Pi

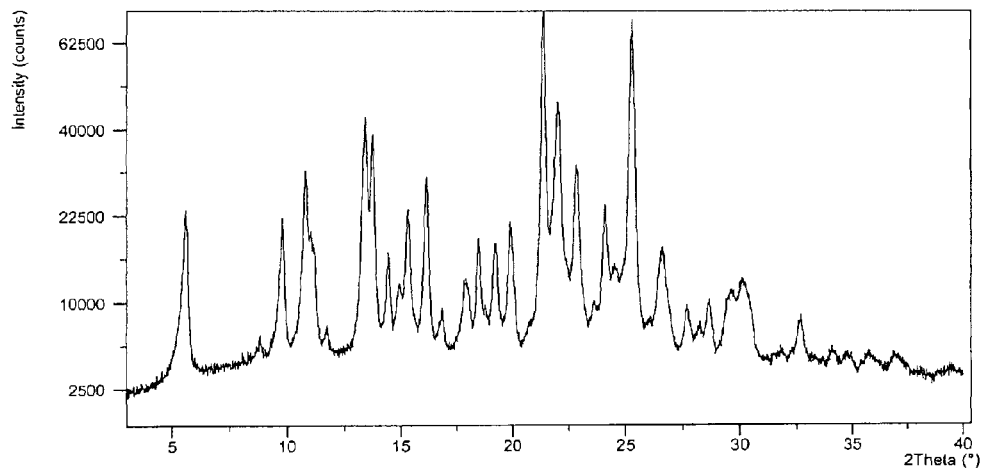
Fig. 59: XRPD of Form Rho (silicon added, no corrections performed)
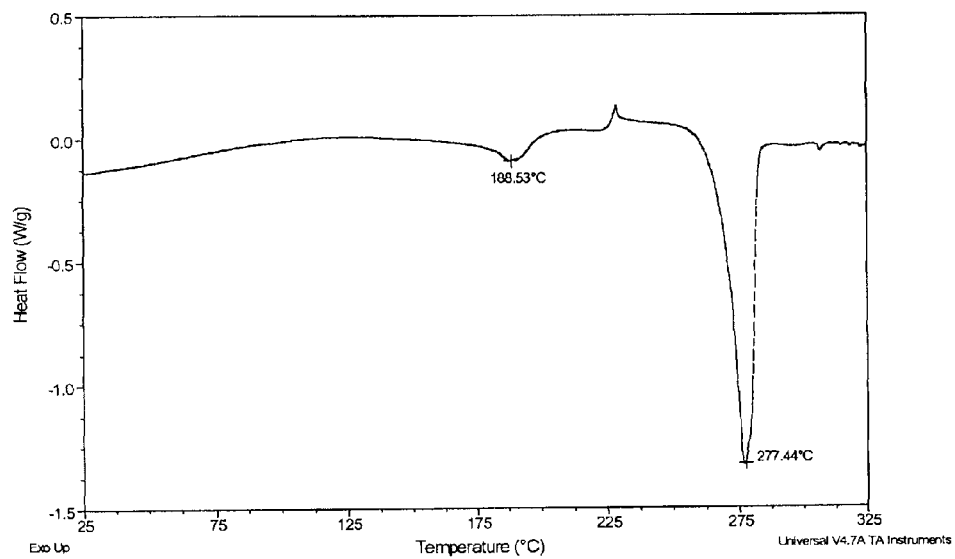
Fig 60. DSC of Form Rho

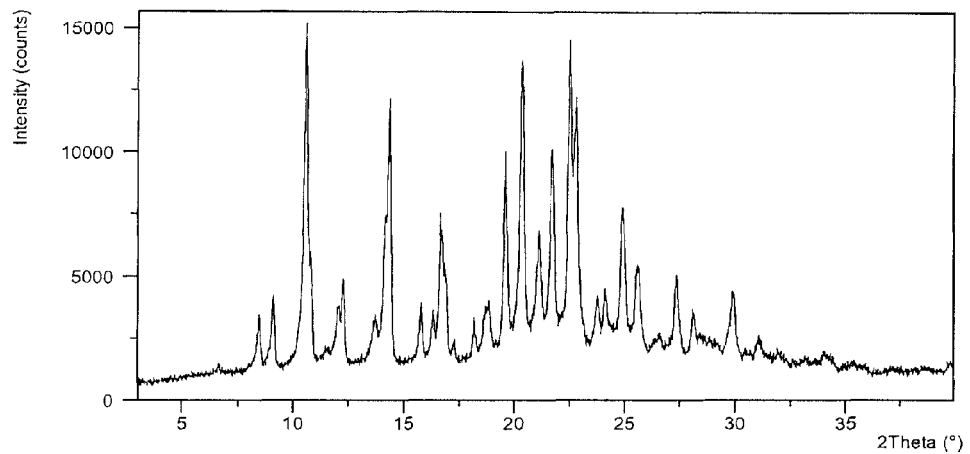
Fig 61. XRPD of Form Sigma
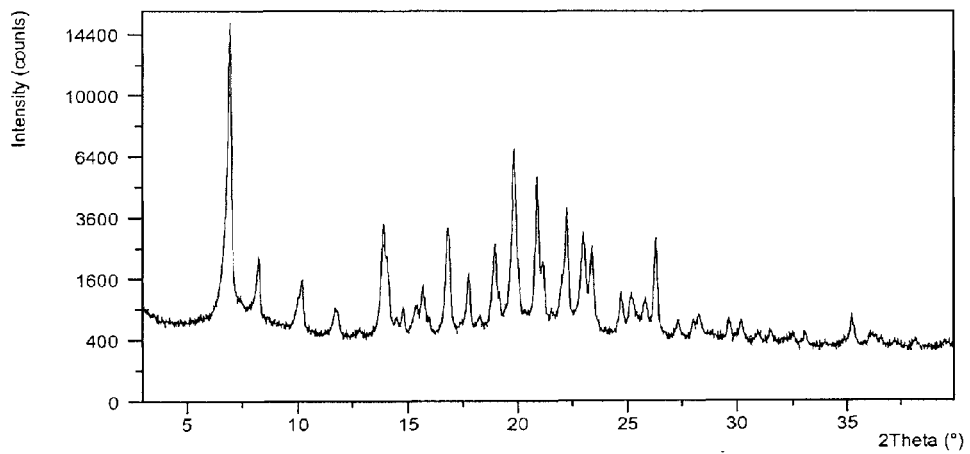
Figure 62. XRPD of Form K

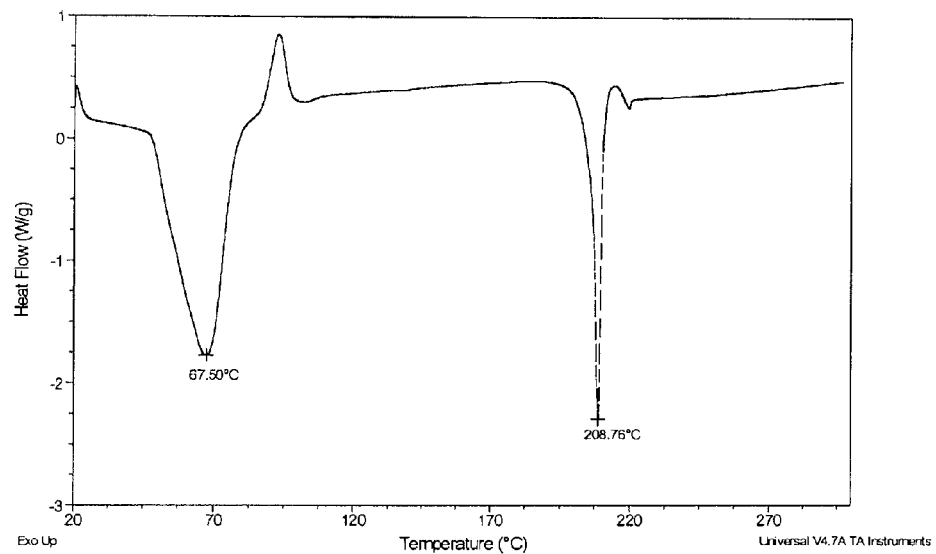
Fig 63. DSC of Form K
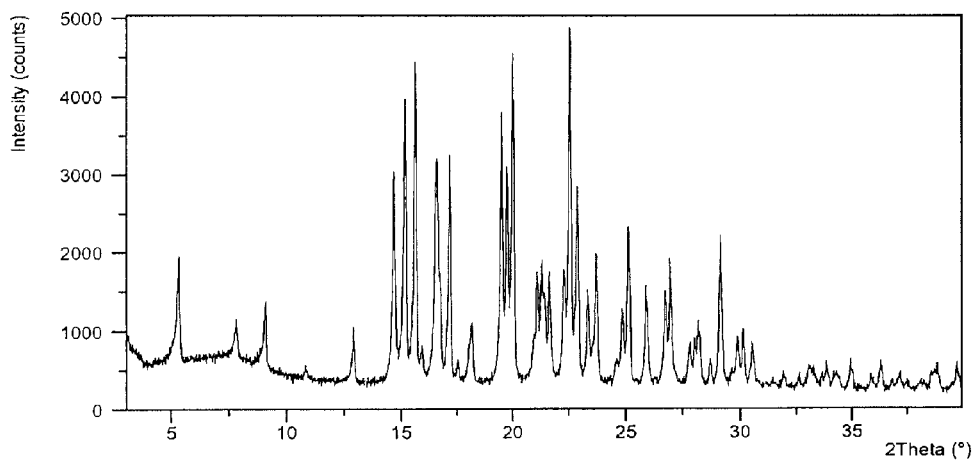
Figure 64. XRPD of Form L

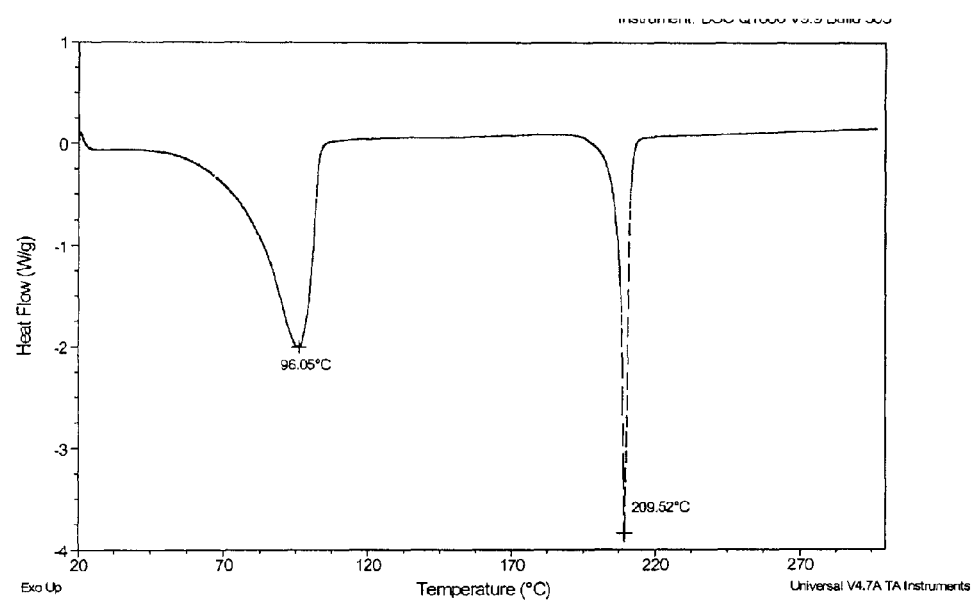
Fig 65. DSC of Form L

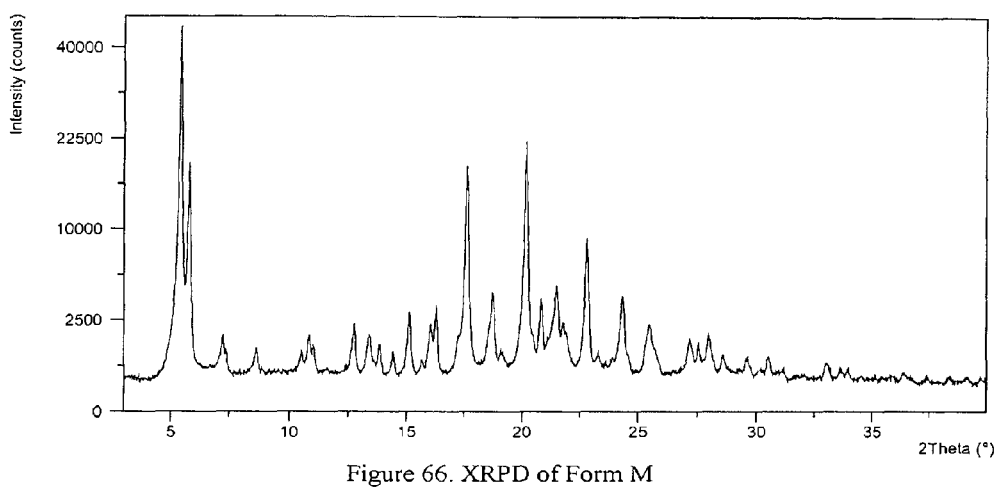
Figure 66. XRPD of Form M

SOLID STATE FORMS OF VILAZODONE AND VILAZODONE HYDROCHLORIDE

CROSS-REFERENCE TO RELATED APPLICATIONS

This application is the National Stage of International Application No. PCT/US2012/066324, filed Nov. 21, 2012, which claims the benefit of U.S. application No. 61/563,150, filed Nov. 23, 2011, U.S. application No. 61/583,368, filed Jan. 5, 2012, U.S. application No. 61/584,499, filed Jan. 9, 2012, U.S. application No. 61/590,412, filed Jan. 25, 2012, U.S. application No. 61/637,416, filed Apr. 24, 2012, U.S. application No. 61/651,221, filed May 24, 2012, U.S. application No. 61/653,778, filed May 31, 2012, U.S. application No. 61/670,895, filed Jul. 12, 2012 and U.S. application No. 61/717,351, filed Oct. 23, 2012, the disclosures of which are incorporated herein by reference in their entirety.

FIELD OF THE INVENTION

The invention relates to solid state forms of Vilazodone and Vilazodone hydrochloride, processes for preparing these solid state forms, and pharmaceutical compositions comprising one or more of these solid state forms.

BACKGROUND OF THE INVENTION

Vilazodone, 5-(4-[4-(5-cyano-1H-indol-3-yl)butyl]piperazin-1-yl)benzofuran-2-carboxamide, has the following chemical structure:

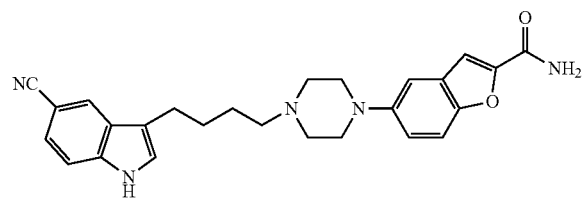 [SMILES: N#Cc1ccc2[nH]cc(CCCCN3CCN(c4ccc5oc(C(N)=O)cc5c4)CC3)c2c1]

Vilazodone (HCl salt marketed as VIIBRYD) is an SSRI antidepressant (selective serotonin reuptake inhibitor and a 5 $HT_{1A}$ receptor partial antagonist) developed for the treatment of major depressive disorder. The compound was originally developed by Merck KGaA, Germany, and is now owned by Forest Laboratories Inc, USA.

A synthesis of Vilazodone is described in U.S. Pat. No. 5,532,241.

Certain crystalline forms of Vilazodone hydrochloride, and of Vilazodone dihydrochloride are described in the PCT Publication No. WO2002102794.

Polymorphism, the occurrence of different crystal forms, is a property of some molecules and molecular complexes. A single compound may give rise to a variety of polymorphs having distinct crystal structures and physical properties like melting point, thermal behaviors (e.g., measured by thermogravimetric analysis—"TGA", or differential scanning calorimetry—"DSC"), powder X-ray diffraction (XRD) pattern, infrared absorption fingerprint, and solid state NMR spectrum. One or more of these techniques may be used to characterize a particular polymorph and to distinguish different polymorphic forms of a compound.

Discovering new polymorphic forms (including new solvates) of a pharmaceutical product can provide materials having, inter alia, desirable processing properties, such as ease of handling, ease of processing, chemical and polymorphic stability upon storage and processing, and ease of purification, or are useful as intermediate crystal forms that facilitate conversion to other polymorphic forms or salts of a pharmaceutical compound. New polymorphic forms and solvates of a pharmaceutically useful compound or salts thereof can also provide opportunities to improve the performance characteristics of a pharmaceutical product. They can also enlarge the repertoire of materials available to a formulation scientist for formulation optimization, for example by providing a product with different properties, e.g., better processing or handling characteristics, improved dissolution profile, or improved shelf-life. Lastly, new polymorphic forms may be prepared with improved reliability and reproducibility compared to other forms, for example in terms of crystallinity or polymorphic purity. For at least these reasons, there is a need for additional polymorphs of Vilazodone and its hydrochloride salt.

SUMMARY OF THE INVENTION

The present invention provides new solid state forms of Vilazodone. These solid state forms can inter alia be used to prepare salts, particularly Vilazodone hydrochloride, solid state forms of those salts and pharmaceutical compositions and formulations thereof.

The present invention also provides new solid state forms of Vilazodone hydrochloride. These solid state forms can be used to prepare pharmaceutical compositions and formulations thereof, or they can be used to prepare Vilazodone free base and/or other salts of Vilazodone and/or formulations thereof.

The invention further provides the solid state forms of Vilazodone and of Vilazodone hydrochloride as described herein for use in the manufacture of a medicament, preferably for the treatment of major depressive disorders; and provides a method of treating major depressive disorders, said method comprising administering a therapeutically effective dose of one or more of the solid state forms described herein.

BRIEF DESCRIPTION OF THE FIGURES

FIG. 1 provides a powder XRD pattern of crystalline Form A of Vilazodone.

FIG. 2 provides a DSC thermogram of crystalline Form A of Vilazodone.

FIG. 3 provides a powder XRD pattern of crystalline Form B of Vilazodone.

FIG. 4 provides a DSC thermogram of crystalline Form B of Vilazodone.

FIG. 5 provides a powder XRD pattern of crystalline Form C of Vilazodone.

FIG. 6 provides a DSC thermogram of crystalline Form C of Vilazodone.

FIG. 7 provides a powder XRD pattern of crystalline Form D of Vilazodone.

FIG. 8 provides a DSC thermogram of crystalline Form D of Vilazodone.

FIG. 9 provides a powder XRD pattern of crystalline Form E of Vilazodone.

FIG. 10 provides a DSC thermogram of crystalline Form E of Vilazodone.

FIG. 11 provides a powder XRD pattern of crystalline Form F of Vilazodone.

FIG. 12 provides a DSC thermogram of crystalline Form F of Vilazodone.

FIG. 13 provides a powder XRD pattern of crystalline Form G of Vilazodone.

FIG. 14 provides a powder XRD pattern of crystalline Form H of Vilazodone.

FIG. 15 provides a powder XRD pattern of crystalline Form I of Vilazodone.

FIG. 16 provides a powder XRD pattern of amorphous Vilazodone.

FIG. 17 provides a DSC thermogram of amorphous Vilazodone.

FIG. 18 provides a powder XRD pattern of amorphous Vilazodone.

FIG. 19 provides a DSC thermogram of amorphous Vilazodone.

FIG. 20 provides a powder XRD pattern of crystalline Form E1 of Vilazodone.

FIG. 21 provides a DSC thermogram of crystalline Form E1 of Vilazodone.

FIG. 22 provides a powder XRD pattern of crystalline Form A1 of Vilazodone.

FIG. 23 provides a DSC thermogram of crystalline Form A1 of Vilazodone.

FIG. 24 provides a powder XRD pattern of crystalline Form Alpha of Vilazodone hydrochloride.

FIG. 25 provides a DSC thermogram of crystalline Form Alpha of Vilazodone hydrochloride.

FIG. 26 provides a powder XRD pattern of crystalline Form Beta of Vilazodone hydrochloride.

FIG. 27 provides a DSC thermogram of crystalline Form Beta of Vilazodone hydrochloride.

FIG. 28 provides a powder XRD pattern of crystalline Form Gamma of Vilazodone hydrochloride.

FIG. 29 provides a DSC thermogram of crystalline Form Gamma of Vilazodone Hydrochloride.

FIG. 30 provides a powder XRD pattern of crystalline Form Delta of Vilazodone hydrochloride.

FIG. 31 provides a DSC thermogram of crystalline Form Delta of Vilazodone hydrochloride.

FIG. 32 provides a powder XRD pattern of crystalline Form Epsilon of Vilazodone hydrochloride.

FIG. 33 provides a DSC thermogram of crystalline Form Epsilon of Vilazodone hydrochloride.

FIG. 34 provides a powder XRD pattern of crystalline Form Eta of Vilazodone hydrochloride.

FIG. 35 provides a DSC thermogram of crystalline Form Eta of Vilazodone hydrochloride.

FIG. 36 provides a powder XRD pattern of crystalline Form Theta of Vilazodone hydrochloride.

FIG. 37 provides a DSC thermogram of crystalline Form Theta of Vilazodone hydrochloride.

FIG. 38 provides a powder XRD pattern of crystalline Form Iota of Vilazodone hydrochloride.

FIG. 39 provides a DSC thermogram of crystalline Form Iota of Vilazodone hydrochloride.

FIG. 40 provides a powder XRD pattern of crystalline Form Kappa of Vilazodone hydrochloride.

FIG. 41 provides a powder XRD pattern of crystalline Form Lambda of Vilazodone hydrochloride.

FIG. 42 provides a DSC thermogram of crystalline Form Lambda of Vilazodone hydrochloride.

FIG. 43 provides a powder XRD pattern of crystalline Form Mu of Vilazodone hydrochloride.

FIG. 44 provides a powder XRD pattern of crystalline Form Nu of Vilazodone hydrochloride.

FIG. 45 provides a powder XRD pattern of amorphous Vilazodone hydrochloride.

FIG. 46 provides a powder XRD pattern of amorphous Vilazodone hydrochloride.

FIG. 47 provides a DSC thermogram of amorphous Vilazodone hydrochloride.

FIG. 48 provides a DSC thermogram of amorphous Vilazodone hydrochloride.

FIG. 49 provides a powder XRD pattern of a solid dispersion of Vilazodone hydrochloride and polyvinylpyrrolidone (PVP).

FIG. 50 provides a powder XRD pattern of a solid dispersion of Vilazodone hydrochloride and hydroxypropyl methylcellulose (HPMC).

FIG. 51 provides a powder XRD pattern of Form Zeta of Vilazodone hydrochloride.

FIG. 52 provides a DSC thermogram of Form Zeta of Vilazodone hydrochloride.

FIG. 53 provides a DSC thermogram of Form Xi of Vilazodone hydrochloride.

FIG. 54 provides a DSC thermogram of Form XI of Vilazodone hydrochloride.

FIG. 55 provides a powder XRD pattern of Form Omicron of Vilazodone hydrochloride.

FIG. 56 provides a DSC thermogram of Form Omicron of Vilazodone hydrochloride.

FIG. 57 provides a powder XRD pattern of Form Pi of Vilazodone hydrochloride.

FIG. 58 provides a DSC thermogram of Form Pi of Vilazodone hydrochloride.

FIG. 59 provides a powder XRD pattern of Form Rho of Vilazodone hydrochloride.

FIG. 60 provides a DSC thermogram of Form Rho of Vilazodone hydrochloride.

FIG. 61 provides a powder XRD pattern of Form Sigma of Vilazodone hydrochloride

FIG. 62 provides a powder of Form K of Vilazodone.

FIG. 63 provides a DSC thermogram of Form K of Vilazodone.

FIG. 64 provides a powder XRD pattern of Form L of Vilazodone.

FIG. 65 provides a DSC of Form L of Vilazodone.

FIG. 66 provides a powder XRD pattern of Form M of Vilazodone.

DETAILED DESCRIPTION OF THE INVENTION

Figure 67:
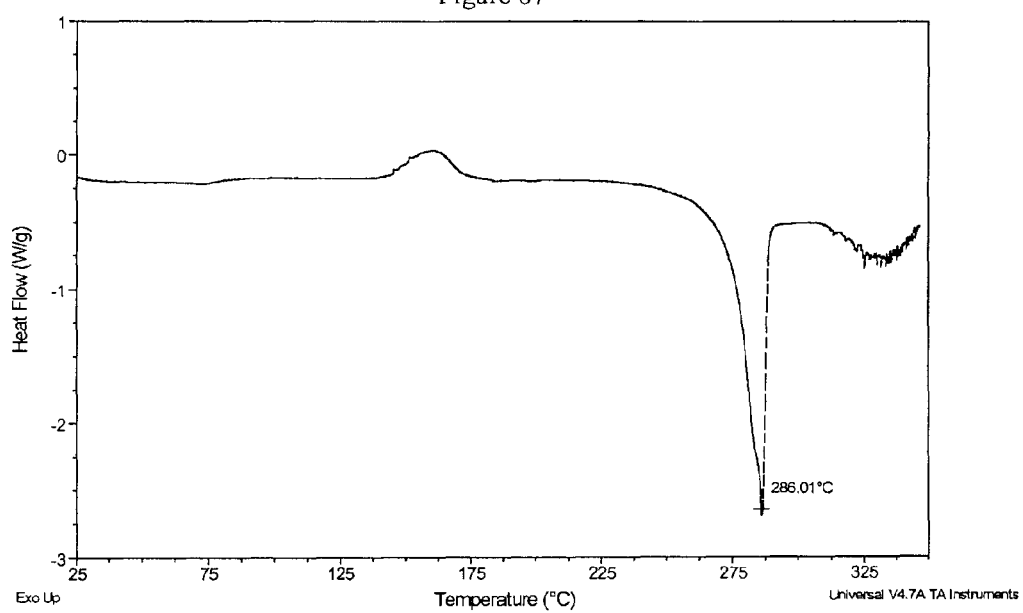
FIG. 67 provides a DSC thermogram of Form Mu of Vilazodone HCl.

The present invention provides new solid state forms of Vilazodone and of Vilazodone hydrochloride. These solid state forms can, for example, be used to prepare salts and/or formulations thereof.

As used herein, the term "Vilazodone" refers to Vilazodone free base.

A polymorph may be referred to herein as substantially free of any other solid forms. As used herein in this context, the expression "substantially free" will be understood to mean that the solid state form contains 20% or less, 10% or less, 5% or less, 2% or less, or 1% or less of any other solid form of the subject compound as measured, for example, by powder X-ray diffraction (PXRD). Thus, polymorphs of Vilazodone described herein as substantially free of any other solid forms would be understood to contain greater than 80% (w/w), greater than 90% (w/w), greater than 95% (w/w), greater than 98% (w/w), or greater than 99% (w/w) of the subject form of Vilazodone. Accordingly, in some embodiments of the invention, the described polymorphs of Vilazodone may contain from 1% to 20% (w/w), from 5% to 20% (w/w), or from 5% to 10% (w/w) of one or more other solid forms of Vilazodone.

A solid state form may be referred to herein as being characterized by graphical data "as shown in" a Figure. Such data include, for example, powder X-ray diffractograms and solid state NMR spectra. The graphical data potentially provides additional technical information to further define the respective solid state form which can not necessarily be described by reference to numerical values or peak positions. In any event, the skilled person will understand that such graphical representations of data may be subject to small variations, e.g., in peak relative intensities and peak positions due to factors such as variations in instrument response and variations in sample concentration and purity, which factors are well known to the skilled person. Nonetheless, the skilled person would readily be capable of comparing the graphical data in the Figures herein with graphical data generated for an unknown crystal form and confirming whether the two sets of graphical data characterize the same solid state form or two different solid state forms. The skilled person would understand that a solid state form referred to herein as being characterized by graphical data "as shown in" a Figure would include any solid state form of the same chemical characterized by graphical data substantially similar to the Figure except for such small variations, the potential occurrence of which is well known to the skilled person.

A solid state form may be referred to herein as being characterized by data selected from two or more different data groupings, for example, by a powder XRD pattern having a group of specific peaks; or by a powder XRD pattern as shown in a figure depicting a diffractogram, or by "a combination thereof" (or "combinations thereof," or "any combination thereof"), These expressions, e.g., "any combination thereof" contemplate that the skilled person may characterize a crystal form using any combination of the recited characteristic analytical data. For example, the skilled person may characterize a crystal form using a group of four or five characteristic powder XRD peaks, and supplement that characterization with one or more additional features observed in the powder X-ray diffractogram, e.g., an additional peak, a characteristic peak shape, a peak intensity, or even the absence of a peak at some position in the powder XRD pattern. Alternatively, the skilled person may in some instances characterize a crystal form using a group of four or five characteristic powder XRD peaks and supplement that characterization with one or more additional features observed using another analytical method, for example, using one or more characteristic peaks in a solid state NMR spectrum, or in a Raman spectrum, or characteristics of the DSC thermogram of the crystal form that is being characterized.

As used herein, unless stated otherwise, powder XRD peaks reported herein are measured using $CuK_\alpha$, radiation, $\lambda=1.54184$ Å.

As used herein, unless indicated otherwise, the term "room temperature" or "RT" or "ambient temperature" refers to a temperature between about 20° C. and about 30° C. Usually, room temperature ranges from about 20° C. to about 25° C.

As used herein, unless indicated otherwise, the term "overnight" refers to a period of between about 15 and about 20 hours, typically between about 16 to about 20 hours.

As used herein, and unless stated otherwise, the term "anhydrous" in relation to crystalline Vilazodone or Vilazodone hydrochloride relates to a crystalline Vilazodone or Vilazodone hydrochloride which contains no more than 1% (w/w), more preferably no more than 0.5% (w/w) of either water or organic solvents as measured by TGA, or by KF.

As used herein, and unless stated otherwise the term "solvate" refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, Form IV relates to a crystalline form of Vilazodone HCL, as described in the PCT Publication No. WO2002102794.

The present invention provides solid state forms of Vilazodone base.

In one embodiment, the present invention provides a Vilazodone methanol solvate.

The present invention also provides a crystalline Vilazodone, designated Form A. Form A can be characterized by data selected from: a powder XRD pattern with peaks at 5.2, 7.7, 10.5, 14.8, and 24.7±0.2 degrees 2θ; a powder XRD pattern as shown in FIG. 1; and any combinations thereof.

Alternatively, Form A can be characterized by a powder XRD pattern having peaks at 5.2, 7.7, 10.5, 14.8, and 24.7±0.2 degrees 2θ, and also having any one, two, three, four or five peaks selected from 16.1, 17.7, 18.6, 19.6, and 24.1±0.2 degrees 2θ.

Form A can be further characterized by a DSC thermogram as shown in FIG. 2.

Form A can be a methanol solvate. Form A can be a solvate containing methanol and water. According to some embodiments, Form A may contain from about 2.0% to about 4.0% w/w water, for example about 2.4% w/w of water, as measured by KF; and from about 4.0% to about 6.0% w/w of methanol, for example about 4.8% w/w of methanol, as measured by GC.

The present invention also provides Vilazodone methyl isobutyl ketone solvate.

The present invention also provides a crystalline Vilazodone, designated Form B. Form B can be characterized by data selected from: a powder XRD pattern having peaks at 5.8, 7.3, 10.9, 18.6, and 20.9±0.2 degrees 2θ; a powder XRD pattern as shown in FIG. 3; and any combinations thereof.

Alternatively, Form B can be characterized by a powder XRD pattern having peaks at 5.8, 7.3, 10.9, 18.6, and 20.9±0.2 degrees 2θ, and also having any one, two, three, four or five peaks selected from 13.8, 16.0, 17.3, 21.4, and 21.9±0.2 degrees 2θ.

Form B can be further characterized by a DSC thermogram as shown in FIG. 4.

Form B can be a methyl isobutyl ketone solvate. Form B can be a solvate containing methyl isobutyl ketone and from about 3.0% to about 4.0% w/w of water, for example, about 3.8% w/w of water, as measured by KF.

The present invention further provides Vilazodone ethylene glycol solvate.

The present invention also provides a form of Vilazodone, designated Form C. Form C can be characterized by data selected from: a powder XRD pattern having peaks at 3.9, 9.6, 13.2, 19.7, and 24.0±0.2 degrees 2θ; a powder XRD pattern as shown in FIG. 5; and any combinations thereof.

Alternatively, Form C can be characterized by a powder XRD pattern having peaks at 3.9, 9.6, 13.2, 19.7, and 24.0±0.2 degrees 2θ, and also having any one, two, three, four or five peaks selected from 15.1, 16.0, 20.9, 22.8 and 27.0±0.2 degrees 2θ.

Form C can be further characterized by a DSC thermogram as shown in FIG. 6.

Form C can be an ethylene glycol solvate. Form C can be a solvate containing ethylene glycol and from about 5.0% to about 7.0% w/w of water, for example, about 5.9% w/w of water, as measured by KF.

The invention further provides a Vilazodone 1-propanol solvate.

The present invention also provides a crystalline Vilazodone, designated Form D. Form D can be characterized by data selected from: a powder XRD pattern having peaks at 5.0, 6.8, 8.4, 20.0, and 29.1±0.2 degrees 2θ; a powder XRD pattern as shown in FIG. 7; and any combinations thereof.

Alternatively, Form D can be characterized by a powder XRD pattern having peaks at 5.0, 6.8, 8.4, 20.0, and 29.1±0.2 degrees 2θ, and also having any one, two, three, four, or five peaks selected from 11.9, 14.4, 16.7, 18.0, and 20.7±0.2 degrees 2θ.

Form D can be a 1-propanol solvate. Form D can be a solvate containing 1-propanol and water. For example, Form D may contain from about 15.0% to about 16.0% w/w of 1-propanol, for example about 15.4% w/w, as measured by GC.

Form D can be further characterized by a DSC thermogram as shown in FIG. 8.

The present invention also provides Vilazodone ethanol solvate.

The present invention also provides a crystalline Vilazodone, designated Form E. Form E can be characterized by data selected from: a powder XRD pattern having peaks at 5.2, 20.3, 21.3, 22.5, 26.6, and 27.4±0.2 degrees 2θ; a powder XRD pattern as shown in FIG. 9; and any combinations thereof.

Alternatively, Form E can be characterized by a powder XRD pattern having peaks at 5.2, 20.3, 21.3, 22.5, 26.6, and 27.4±0.2 degrees 2θ, and also having any one, two, three, or four peaks selected from 6.8, 8.5, 16.6, and 29.8±0.2 degrees 2θ.

Form E can be further characterized by a DSC thermogram as shown in FIG. 10.

Form E can be an ethanol solvate. Form E can be a solvate containing from about 3.0% to about 5.0% w/w of ethanol, for example about 3.6% w/w of ethanol, as measured by GC, and from about 4.0% to about 6.0% w/w of water, for example about 4.3% w/w of water, as measured by KF.

The present invention further provides Vilazodone 1-butanol solvate.

The present invention also provides a crystalline Vilazodone, designated Form F. Form F can be characterized by data selected from: a powder XRD pattern having peaks at 5.0, 6.8, 14.4, 22.2, and 22.6±0.2 degrees 2θ; a powder XRD pattern as shown in FIG. 11; and any combinations thereof.

Alternatively, Form F can be characterized by a powder XRD pattern having peaks at 5.0, 6.8, 14.4, 22.2, and 22.6±0.2 degrees 2θ, and also having any one, two, three, four, or five peaks selected from 8.4, 12.1, 18.2, 19.5 and 20.9±0.2 degrees 2θ.

Form F can be further characterized by a DSC thermogram as shown in FIG. 12.

Form F can be a 1-butanol solvate. Form F can be a solvate containing from about 17.0% to about 19.0% w/w of 1-butanol, for example, about 17.3% w/w of 1-butanol, as measured by GC, and from about 3.0% to about 5.0% w/w of water, for example, about 3.7% w/w of water, as measured by KF.

The present invention also provides a crystalline Vilazodone, designated Form G. Form G can be characterized by data selected from: a powder XRD pattern having peaks at 5.7, 7.3, 10.9, 13.8, and 24.0±0.2 degrees 2θ; a powder XRD pattern as shown in FIG. 13; and any combinations thereof.

Form G can be an anhydrous.

Alternatively, Form G can be characterized by a powder XRD pattern having peaks at 5.7, 7.3, 10.9, 13.8, and 24.0±0.2 degrees 2θ, and also having any one, two, three, four, or five peaks selected from 13.3, 17.4, 18.5, 20.9 and 21.3±0.2 degrees 2θ.

The present invention also provides a crystalline Vilazodone, designated Form H. Form H can be characterized by data selected from: a powder XRD pattern having peaks at 5.7, 9.0, 10.0, 17.0, and 23.1±0.2 degrees 2θ; a powder XRD pattern as shown in FIG. 14; and any combinations thereof.

Form H can be an anhydrous.

Alternatively, Form H can be characterized by a powder XRD pattern having peaks at 5.7, 9.0, 10.0, 17.0, and 23.1±0.2 degrees 2θ, and also having any one, two, three, four, or five peaks selected from 7.3, 15.3, 15.7, 18.4, and 20.3±0.2 degrees 2θ.

The present invention also provides a crystalline Vilazodone, designated Form I. Form I can be characterized by data selected from: a powder XRD pattern having peaks at 5.5, 8.6, 17.7, 20.3, and 22.9±0.2 degrees 2θ; a powder XRD pattern as shown in FIG. 15; and any combinations thereof.

Alternatively, Form I can be characterized by a powder XRD pattern having peaks at 5.5, 8.6, 17.7, 20.3, and 22.9±0.2 degrees 2θ, and also having any one, two, three, four, or five peaks selected from 7.2, 10.5, 12.7, 13.4, and 14.5±0.2 degrees 2θ.

Form I can be an anhydrous.

The present invention also provides a crystalline Vilazodone, designated Form E1. Form E1 can be characterized by data selected from: a powder XRD pattern having peaks at 5.5, 6.8 and 8.3 degrees 2θ±0.2 degrees 2θ; a powder XRD pattern as shown in FIG. 20; and any combinations thereof.

Form E1 may be a hydrate, or a methanol solvate—hydrate. For example, Form E1 may contain from about 2.0% to about 4.0% w/w of water, for example about 2.6% w/w of water, as measured by KF, and from about 5.0% to about 7.0% w/w of ethanol, for example about 6.0% w/w of ethanol, as measured by GC.

Alternatively, Form E1 can be characterized by a powder XRD pattern having peaks at 5.5, 6.8 and 8.3 degrees 2θ±0.2 degrees 2θ, and also having any one, two or three peaks selected from 12.2, 13.5 and 17.0 degrees 2θ±0.2 degrees 2θ.

Form E1 can be further characterized by a DSC thermogram as shown in FIG. 21.

Form E1 can be characterized by any combination of the above analytical data.

The present invention also provides a crystalline Vilazodone, designated Form A1. Form A1 can be characterized by data selected from: a powder XRD pattern having peaks at 5.6, 11.1, 22.6 and 25.1 degrees 2θ±0.2 degrees 2θ; a powder XRD pattern as shown in FIG. 22; and any combinations thereof.

Form A1 may be a hydrate, or a methanol solvate—hydrate. For example, Form A1 may contain from about 3% to about 5% w/w of water, for example about 3.3% w/w of water, as measured by KF, and from about 1% to about 3% w/w of methanol, for example about 1.9% w/w of methanol, as measured by GC.

Alternatively, Form A1 can be characterized by a powder XRD pattern having peaks at 5.6, 11.1, 22.6 and 25.1 degrees 2θ±0.2 degrees 2θ, and also having any one, two, three, four, five or six peaks selected from 7.7, 14.4, 16.1, 18.8, 20.6 and 27.0 degrees 2θ±0.2 degrees 2θ.

Form A1 can be further characterized by a DSC thermogram as shown in FIG. 23.

Form A1 can be characterized by any combination of the above data.

The present invention also provides a crystalline Vilazodone, designated Form K. Form K can be characterized by data selected from: a powder XRD pattern having peaks at 7.0, 13.9, 16.9, 19.9, and 20.9 degrees 2θ±0.2 degrees 2θ; a powder XRD pattern as shown in FIG. 62; and any combinations thereof.

Alternatively, Form K can be characterized by a powder XRD pattern having peaks at 7.0, 13.9, 16.9, 19.9, and 20.9 degrees 2θ±0.2 degrees 2θ, and also having any one or more peaks selected from 10.2, 15.7, 19.0, 22.3, and 26.3 degrees 2θ±0.2 degrees 2θ.

Form K can be further characterized by a DSC thermogram as shown in FIG. 63.

Form K can be characterized by any combination of the above analytical data.

The present invention also provides a crystalline Vilazodone, designated Form L. Form L can be characterized by data selected from: a powder XRD pattern having peaks at 9.1, 12.9, 14.7, 15.2, and 22.9 degrees 2θ±0.2 degrees 2θ; a powder XRD pattern as shown in FIG. 64; and any combinations thereof.

Alternatively, Form L can be characterized by a powder XRD pattern having peaks at 9.1, 12.9, 14.7, 15.2, and 22.9 degrees 2θ±0.2 degrees 2θ, and also having any one or more peaks selected from 5.3, 16.6, 17.2, 19.5, and 20.1 degrees 2θ±0.2 degrees 2θ.

Form L can be further characterized by a DSC thermogram as shown in FIG. 65.

Form L can be characterized by any combination of the above analytical data.

The present invention also provides a crystalline Vilazodone, designated Form M. Form M can be characterized by data selected from: a powder XRD pattern having peaks at 5.4, 7.2, 8.6, 17.6 and 22.8 degrees 2θ±0.2 degrees 2θ; a powder XRD pattern as shown in FIG. 66; and any combinations thereof.

Alternatively, Form M can be characterized by a powder XRD pattern having peaks at 5.4, 7.2, 8.6, 17.6 and 22.8 degrees 2θ±0.2 degrees 2θ, and also having any one or more peaks selected from 10.5, 10.8, 12.8, 14.4, and 15.1 degrees 2θ±0.2 degrees 2θ.

The present invention also provides amorphous Vilazodone.

The amorphous Vilazodone can be characterized by a powder XRD pattern as shown in any one of FIG. 16 or 18; or by a DSC thermogram as shown in any one of FIG. 17 or 19.

The above described solid state forms of Vilazodone can be used to prepare Vilazodone salts, for example Vilazodone HCl, their solid state forms and formulations thereof.

For example, the present invention encompasses a process for preparing Vilazodone salts and solid state forms thereof comprising preparing any one or any mixture of Vilazodone solid state forms of the present invention and converting them to a Vilazodone salt. The conversion can be done, for example, by a process comprising reacting any one or any mixture of the above described Vilazodone solid state forms and an appropriate acid, to obtain the corresponding salt.

The present invention also provides solid state forms of Vilazodone Hydrochloride.

In one embodiment, the present invention provides a crystalline Vilazodone hydrochloride, designated Form Alpha. Form Alpha can be characterized by data selected from: a powder XRD pattern having peaks at 7.1, 7.9, 12.7, 17.4, 21.7 and 25.9 degrees 2θ±0.2 degrees 2θ; a powder XRD pattern as shown in FIG. 24; a Raman spectrum having peaks at 3112.1, 2968.6, 2915.2, 2850.1, 2220.1, 1613.8, 1579.4, 1547.1, 1437.9, 1269.3, 1124.4, 824.3, 500.3, 408.4±4 cm$^{-1}$; a Raman spectrum as shown in FIG. 68; and any combinations thereof.

Figure 68:
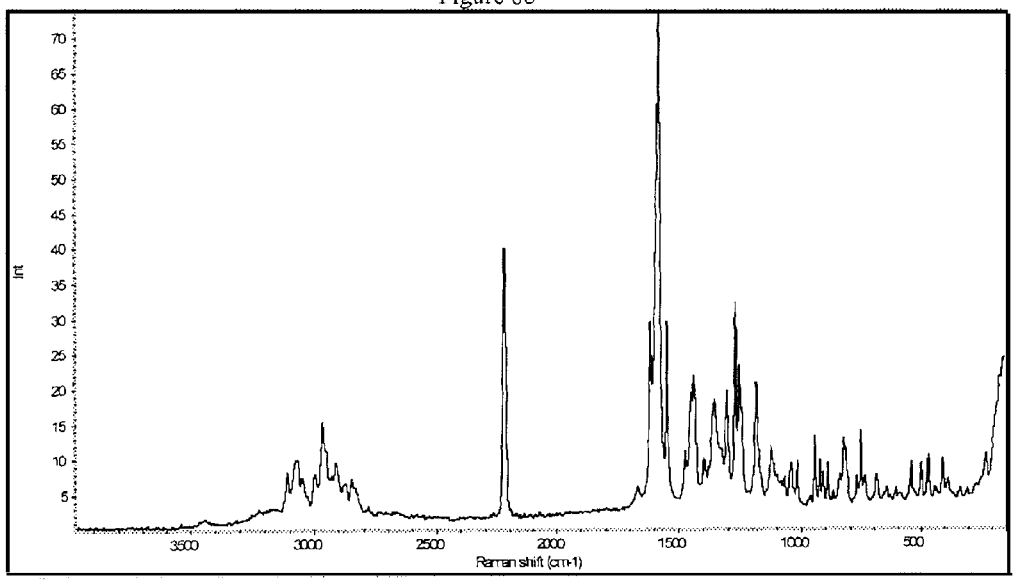
FIG. 68 provides a Raman spectrum of Form Alpha of Vilazodone HCl.

Alternatively, Form Alpha can be characterized by a powder XRD pattern having peaks at 7.1, 7.9, 12.7, 17.4, 21.7 and 25.9 degrees 2θ±0.2 degrees 2θ; or a powder XRD pattern as shown in FIG. 24; or a Raman spectrum having peaks at 3112.1, 2968.6, 2915.2, 2850.1, 2220.1, 1613.8, 1579.4, 1547.1, 1437.9, 1269.3, 1124.4, 824.3, 500.3, 408.4±4 cm$^{-1}$.; or a Raman spectrum as shown in FIG. 68; or any combinations thereof.

Alternatively, Form Alpha can be characterized by a powder XRD pattern having peaks at 7.1, 7.9, 12.7, 17.4, 21.7 and 25.9 degrees 2θ±0.2 degrees 2θ, and also having any one, two, three, four, five, six or seven peaks selected from 8.7, 10.5, 12.1, 15.0, 16.3, 19.7 and 22.5 degrees 2θ±0.2 degrees 2θ.

Form Alpha can further be characterized by an DSC endothermic peak at about 281.3° C.±1° C., and a DSC exothermic peak at about 179.0° C.±1° C. Alternatively, Form Alpha can be characterized by a DSC thermogram as shown in FIG. 25

Form Alpha may be a hydrate. For example, it may contain about 3.0 to about 10.0% w/w of water, or about 5.0 to about 7.0% w/w of water as measured by KF.

Form Alpha can be characterized by any combination of the above data.

Form Alpha can be prepared, for example by a process comprising suspending Vilazodone Form B in methanol, and adding HCl.

It was found that Form Alpha has overall excellent physico-chemical properties. Form Alpha exhibits advantageous properties selected from at least one of the following: chemical purity, flowability, solubility, morphology or crystal habit, specific surface and pycnometric density, bulk/tap density, stability—such as storage stability, stability to dehydration, stability to polymorphic conversion, low hygroscopicity, and low content of residual solvents. These powder characteristics can greatly affect the efficiency, productivity and quality of formulation processes.

In particular, Form Alpha is chemically and polymorphically stable, for example when exposed to heating and to mechanical pressure. Moreover, it exhibits excellent compressibility, which is an important technical property, e.g. when the API is pressed into a palette. For example, when pressing the samples of Vilazodone HCl Form Alpha with 1 ton for 60 minutes, the resulting palettes showed high structural order and shape without visible lamination on the surface or breaking of the palettes.

In addition to the above mentioned advantages, it was found that Form Alpha in particular shows an enhanced degree of wettability. Enhanced wettability is a desirable property of the API as it ensures proper solubilization of the compound in a formulation.

The present invention also provides a crystalline Vilazodone hydrochloride, designated Form Beta. Form Beta can be characterized by data selected from: a powder XRD pattern having peaks at 5.5, 9.6, 11.1, 13.9, 20.3 and 25.7 degrees 2θ±0.2 degrees 2θ; a powder XRD pattern as shown in FIG. 26; and any combinatioνσ thereof.

Alteρvatively, Form Beta can be characterized by a powder XRD pattern having peaks at 5.5, 9.6, 11.1, 13.9, 20.3 and 25.7 degrees 2θ±0.2 degrees 2θ, and also having any one, two, three, four, five or six peaks selected from 10.7, 15.4, 17.5, 18.5, 19.3 and 24.8 degrees 2θ±0.2 degrees 2θ.

Form B may contain diethyl ether and DMF. For example, it may contain from about 5.5% to about 7.0% w/w of diethyl ether, for example about 5.5% w/w of diethyl ether, as measured by GC, and from about 17.0% to about 19.0% w/w of DMF, for example about 17.9% w/w of DMF, as measured by GC.

Form Beta can be further characterized by a DSC thermogram as shown in FIG. 27.

Form Beta can be characterized by any combination of the above data.

The present invention also provides a crystalline Vilazodone hydrochloride, designated Form Gamma. Form Gamma can be characterized by data selected from: a powder XRD pattern having peaks at 15.8, 19.3, 20.6, 23.1, 24.5 and 26.3 degrees 2θ±0.2 degrees 2θ; a powder XRD pattern as shown in FIG. 28; and any combinations thereof.

Alternatively, Form Gamma can be characterized by a powder XRD pattern having peaks at 15.8, 19.3, 20.6, 23.1, 24.5 and 26.3 degrees 2θ±0.2 degrees 2θ, and also having any one, two, three, four, five, six or seven peaks selected from 5.4, 10.7, 13.5, 17.7, 22.6, 26.9 and 33.1 degrees 2θ±0.2 degrees 2θ.

Form Gamma can be further characterized by a DSC thermogram as shown in FIG. 29.

Form Gamma may contain N-methyl pyrrolidinone (NMP) and ethylacetate. According to some embodiments, it may contain about 8.0% to about 10.0%, for example, about 8.1% w/w of NMP, as measured by GC, and about 1.0% to about 3.0%, for example about 1.2% w/w of ethylacetate, as measured by GC.

Form Gamma can be characterized by any combination of the above data.

The present invention also provides a crystalline Vilazodone hydrochloride, designated Form Delta. Form Delta can be characterized by data selected from: a powder XRD pattern having peaks at 15.9, 19.6, 21.1, 22.1 and 25.8 degrees 2θ±0.2 degrees 2θ; a powder XRD pattern as shown in FIG. 30; and any combinations thereof.

Alternatively, Form Delta can be characterized by a powder XRD pattern having peaks at 15.9, 19.6, 21.1, 22.1 and 25.8 degrees 2θ±0.2 degrees 2θ, and also having any one, two, three, four or five peaks selected from 5.4, 9.6, 13.2, 16.6 and 29.6 degrees 2θ±0.2 degrees 2θ.

Form Delta can be further characterized by a DSC thermogram as shown in FIG. 31.

Form Delta may contain NMP and acetone. According to some embodiments, Form Delta may contain from about 5.0% to about 7.0% w/w of NMP, for example about 6.5% w/w of NMP, as measured by GC, and from about 2.0% to about 4.0% w/w of acetone, for example, about 3.1% w/w of acetone, as measured by GC.

Form Delta can be characterized by any combination of the above data.

The present invention also provides a crystalline Vilazodone hydrochloride, designated Form Epsilon. Form Epsilon can be characterized by data selected from: a powder XRD pattern having peaks at 5.6, 11.1, 13.4, 16.0 and 21.3 degrees 2θ±0.2 degrees 2θ; a powder XRD pattern as shown in FIG. 32; and any combinations thereof.

Alternatively, Form Epsilon can be characterized by a powder XRD pattern having peaks at 5.6, 11.1, 13.4, 16.0 and 21.3 degrees 2θ±0.2 degrees 2θ, and also having any one, two, three, four or five peaks selected from 9.7, 17.7, 19.2, 23.9 and 24.8 degrees 2θ±0.2 degrees 2θ.

Form Epsilon can be further characterized by a DSC thermogram as shown in FIG. 33.

Form Epsilon may contain ethyl acetate. According to some embodiments, Form Epsilon may contain from about 9.0% to about 11.0% w/w of ethyl acetate, for example about 10.3% w/w of ethyl acetate, as measured by GC.

Form Epsilon can be characterized by any combination of the above data.

The present invention also provides a crystalline Vilazodone hydrochloride, designated Form Eta. Form Eta can be characterized by data selected from: a powder XRD pattern having peaks at 10.8, 13.6, 13.9, 15.1, 19.4 and 25.1 degrees 2θ±0.2 degrees 2θ; a powder XRD pattern as shown in FIG. 34; and any combinations thereof.

Alternatively, Form Eta can be characterized by a powder XRD pattern having peaks at 10.8, 13.6, 13.9, 15.1, 19.4 and 25.1 degrees 2θ±0.2 degrees 2θ, and also having any one, two, three, four or five peaks selected from 5.6, 9.6, 17.6, 20.0 and 23.1 degrees 2θ±0.2 degrees 2θ.

Form Eta can be further characterized by a DSC thermogram as shown in FIG. 35.

Form Eta may contain methyl ethyl ketone. According to some embodiments, Form Eta may contain from about 18.0% to about 22.0% w/w of methyl ethyl ketone, for example about 20.0% w/w of methyl ethyl ketone, as measured by GC.

Form Eta can be characterized by any combination of the above data.

The present invention also provides a crystalline Vilazodone hydrochloride, designated Form Theta. Form Theta can be characterized by data selected from: a powder XRD pattern having peaks at 9.4, 10.9, 14.0, 17.0, 24.1 and 27.2 degrees 2θ±0.2 degrees 2θ; a powder XRD pattern as shown in FIG. 36; and any combinations thereof.

Alternatively, Form Theta can be characterized by a powder XRD pattern having peaks at 9.4, 10.9, 14.0, 17.0, 24.1 and 27.2 degrees 2θ±0.2 degrees 2θ, and also having any one, two, three or four peaks selected from 5.5, 18.9, 19.7 and 20.3 degrees 2θ±0.2 degrees 2θ.

Form Theta can be further characterized by a DSC thermogram as shown in FIG. 37.

Form Theta may contain n-butyl acetate. According to some embodiments, Form Theta may contain from about 8.0% to about 12.0% w/w of n-butyl acetate, for example, about 10.0% w/w of n-butyl acetate, as measured by GC.

Form Theta can be characterized by any combination of the above data.

The present invention also provides a crystalline Vilazodone hydrochloride, designated Form Iota. Form Iota can be characterized by data selected from: a powder XRD pattern having peaks at 6.2, 9.3, 12.4, 20.7 and 25.5 degrees 2θ±0.2 degrees 2θ; a powder XRD pattern as shown in FIG. 38; and any combinations thereof.

Alternatively, Form Iota can be characterized by a powder XRD pattern having peaks at 6.2, 9.3, 12.4, 20.7 and 25.5 degrees 2θ±0.2 degrees 2θ, and also having any one, two, three, four or five peaks selected from 10.3, 15.5, 16.2, 19.0 and 21.6 degrees 2θ±0.2 degrees 2θ.

Form Iota can be further characterized by a DSC thermogram as shown in FIG. 39.

Form Iota can be characterized by any combination of the above data.

The present invention also provides a crystalline Vilazodone hydrochloride, designated Form Kappa. Form Kappa can be characterized by data selected from: a powder XRD pattern having peaks at 5.4, 10.2, 11.4, 15.8 and 26.5 degrees 2θ±0.2 degrees 2θ; a powder XRD pattern as shown in FIG. 40; and any combinations thereof.

Alternatively, Form Kappa can be characterized by a powder XRD pattern having peaks at 5.4, 10.2, 11.4, 15.8 and 26.5 degrees 2θ±0.2 degrees 2θ, and also having any one, two, three, four or five peaks selected from 10.8, 13.6, 17.7, 22.7 and 24.8 degrees 2θ±0.2 degrees 2θ.

Form Kappa can be characterized by any combination of the above data.

The present invention also provides a crystalline Vilazodone hydrochloride, designated Form Lambda. Form Lambda can be characterized by data selected from: a powder XRD pattern having peaks at 12.3, 14.8, 15.6, 16.6 and 24.6 degrees 2θ±0.2 degrees 2θ; a content of less than 50% w/w of amorphous Vilazodone HCl; a powder XRD pattern as shown in FIG. 41; a Raman spectrum having peaks at 3124.1, 3078.3, 2995.9, 2878.0, 2851.0, 2217.6, 1676.4, 1615.7, 1593.1, 1578.4, 1549.6, 1439.4, 1364.0, 1243.4, 1136.9, 938.9, 822.0, 771.5, 752.9, 408.1±4 cm$^{-1}$; a Raman spectrum as shown in FIG. 70; and any combinations thereof.

Figure 70:
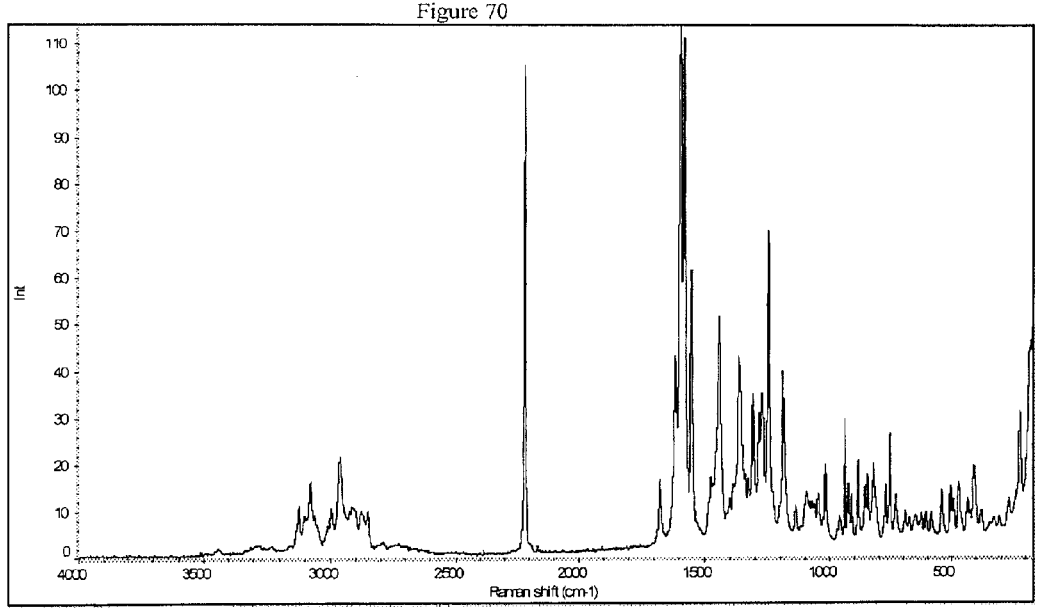
FIG. 70 provides a Raman spectrum of Form Lambda of Vilazodone HCl.

Alternatively, Form Lambda can be characterized by a powder XRD pattern having peaks at 12.3, 14.8, 15.6, 16.6 and 24.6 degrees 2θ±0.2 degrees 2θ; or a content of less than 50% w/w of amorphous Vilazodone HCl; or a powder XRD pattern as shown in FIG. 41; or a Raman spectrum having peaks at 3124.1, 3078.3, 2995.9, 2878.0, 2851.0, 2217.6, 1676.4, 1615.7, 1593.1, 1578.4, 1549.6, 1439.4, 1364.0, 1243.4, 1136.9, 938.9, 822.0, 771.5, 752.9, 408.1±4 cm$^{-1}$; or a Raman spectrum as shown in FIG. 70; or any combinations thereof.

Form Lambda can be characterized by any combination of the above data. For example, Form Lambda may be characterized by a powder XRD pattern having peaks at 12.3, 14.8, 15.6, 16.6 and 24.6 degrees 2θ±0.2 degrees 2θ; and a content of less than 50% w/w of amorphous Vilazodone HCl.

Alternatively, Form Lambda can be characterized by a powder XRD pattern having peaks at 12.3, 14.8, 15.6, 16.6 and 24.6 degrees 2θ±0.2 degrees 2θ, and also having any one, two, three, four or five peaks selected from 7.8, 8.6, 10.5, 21.6 and 33.6 degrees 2θ±0.2 degrees 2θ; and a content of less than 50% w/w of Vilazodone HCl.

Form Lambda can be further characterized by a DSC endothermic peak at about 282.8° C.±1° C., and preferably by an additional endothermic peak at about 118.8° C.±1° C. Alternatively, Form Lambda may be characterized by a DSC thermogram as shown in FIG. 42.

Form Lambda may be a hydrate. According to some embodiments, it may contain from about 3.0 to about 10.0% w/w of water, or from about 4.0% to about 9.5% w/w of water, or from about 4.8% to about 9.2% w/w of water, as measured by KF.

In a particular embodiment, Form Lambda may contain less than 40%, or less than 30%, or less than 20%, or less than 10% w/w of amorphous Vilazodone HCl.

Form Lambda can be characterized by any combination of the above data. For example, Form Lambda may be characterized by a powder XRD pattern having peaks at 12.3, 14.8, 15.6, 16.6 and 24.6 degrees 2θ±0.2 degrees 2θ; and a content of less than 50% w/w of amorphous Vilazodone.

A skilled person can measure the amorphous content in Form Lambda using known methods such as, but not limited to: NIR, Raman, solid-state NMR, and FTIR.

Form Lambda can be prepared, for example, by a process comprising suspending Vilazodone Form B in water, and adding HCl.

It was found that Form Lambda has overall excellent physico-chemical. Form Lambda exhibits advantageous properties selected from at least one of the following: chemical purity, flowability, solubility, morphology or crystal habit, specific surface and pycnometric density, bulk/tap density, stability—such as storage stability, stability to dehydration, stability to polymorphic conversion, low hygroscopicity, and low content of residual solvents. These powder characteristics can greatly affect the efficiency, productivity and quality of formulation processes.

In particular, it was observed that Form Lambda possesses a favorable Hausner ratio (ratio between tapped density and poured (bulk) density) enabling high powder flow rate, high powder settled bulk density and the ability to achieve high production rate. These properties enable improve tablet density uniformity, weight variation, homogeneity, die fill characteristics, dimensional control and ejection characteristics.

Form Lambda doesn't convert to another polymorph when exposed to humidity. For example, when exposed to 100% relative humidity for at least a few moths it remains unchanged.

The present invention also provides a crystalline Vilazodone hydrochloride, designated Form Mu. Form Mu can be characterized by data selected from: a powder XRD pattern having peaks at 5.1, 10.8, 13.9, 20.1 and 25.9 degrees 2θ±0.2 degrees 2θ; a powder XRD pattern as shown in FIG. 43; a Raman spectrum having peaks at 3065.2, 2958.5, 2906.9, 2849.3, 2214.2, 1664.1, 1615.2, 1595.5, 1554.1, 1444.4, 1361.8, 1267.1, 1183.9, 1070.4, 936.7, 753.4, 540.1, 407.6±4 cm$^{-1}$; a Raman spectrum as shown in FIG. 69; and any combinations thereof.

Figure 69:
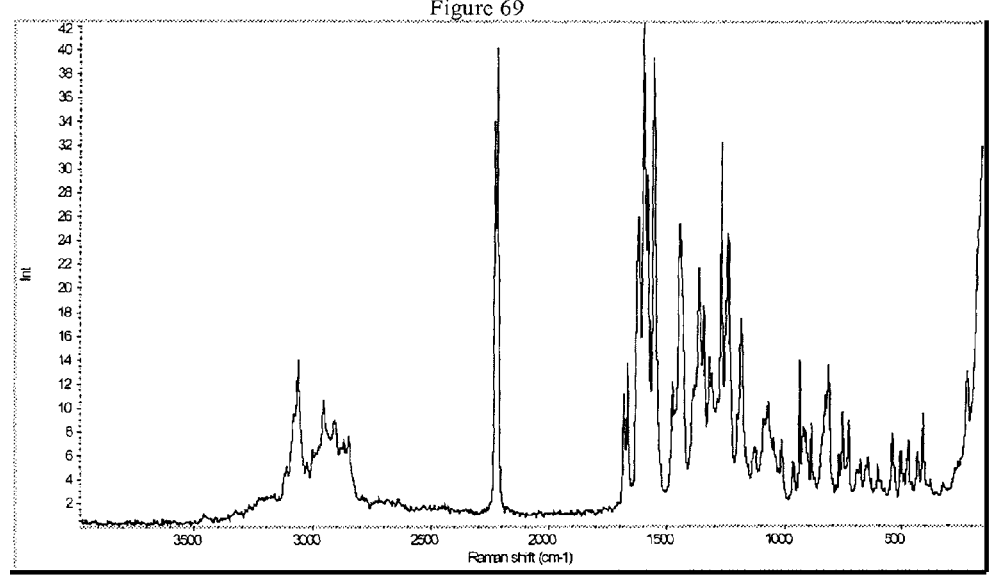
FIG. 69 provides a Raman spectrum of Form Mu of Vilazodone HCl

Alternatively, Form Mu can be characterized by a powder XRD pattern having peaks at 5.1, 10.8, 13.9, 20.1 and 25.9 degrees 2θ±0.2 degrees 2θ; or a powder XRD pattern as shown in FIG. 43; or a Raman spectrum having peaks at 3065.2, 2958.5, 2906.9, 2849.3, 2214.2, 1664.1, 1615.2, 1595.5, 1554.1, 1444.4, 1361.8, 1267.1, 1183.9, 1070.4, 936.7, 753.4, 540.1, 407.6±4 cm$^{-1}$; or a Raman spectrum as shown in FIG. 69; or any combinations thereof.

Alternatively, Form Mu can be characterized by a powder XRD pattern having peaks at 5.1, 10.8, 13.9, 20.1 and 25.9 degrees 2θ±0.2 degrees 2θ, and also having any one, two, three, four, five, six, seven or eight peaks selected from 15.4, 16.4, 17.9, 18.7, 20.8, 21.6, 22.5 and 24.0 degrees 2θ±0.2 degrees 2θ.

Form Mu may be an anhydrous form.

Form Mu can be characterized by any combination of the above data.

Form Mu can be prepared, for example, by a process comprising heating Vilazodone HCl Form Lambda.

It was found that Form Mu has overall excellent physico-chemical. Form Mu exhibits advantageous properties selected from at least one of the following: chemical purity, flowability, solubility, morphology or crystal habit, specific surface and pycnometric density, bulk/tap density, stability—such as storage stability, stability to dehydration, stability to polymorphic conversion, low hygroscopicity, and low content of residual solvents. These powder characteristics can greatly affect the efficiency, productivity and quality of formulation processes.

Form Mu exhibits high chemical and polymorphic stability when put under pressure or heating. when pressing the samples of Vilazodone HCl Form Mu with 1 ton for 60 minutes, the resulting palettes showed high structural order and shape without visible lamination on the surface or breaking of the palettes.

The present invention also provides a crystalline Vilazodone hydrochloride, designated Form Nu. Form Nu can be characterized by data selected from: a powder XRD pattern having peaks at 5.6, 11.3, 12.4, 13.4, 15.6 and 21.5 degrees 2θ±0.2 degrees 2θ; a powder XRD pattern as shown in FIG. 44; and any combinations thereof.

Alternatively, Form Nu can be characterized by a powder XRD pattern having peaks at 5.6, 11.3, 12.4, 13.4, 15.6 and 21.5 degrees 2θ±0.2 degrees 2θ; or a powder XRD pattern as shown in FIG. 44; or any combinations thereof.

Alternatively, Form Nu can be characterized by a powder XRD pattern having peaks at 5.6, 11.3, 12.4, 13.4, 15.6 and 21.5 degrees 2θ±0.2 degrees 2θ, and also having any one, two, three, four, five, six, or seven peaks selected from 9.1, 14.3, 17.5, 19.0, 19.3, 22.2 and 23.7 degrees 2θ±0.2 degrees 2θ.

Form Nu may be an anhydrous form.

Form Nu can be characterized by any combination of the above data.

Form Nu can be prepared, for example, according to a process comprising heating Vilazodone HCl Form Alpha.

Form Nu has overall excellent physico-chemical properties. Form Nu has advantageous properties selected from at least one of the following: chemical purity, flowability, solubility, morphology or crystal habit, specific surface and pycnometric density, bulk/tap density, stability—such as storage stability, stability to dehydration, stability to polymorphic conversion, low hygroscopicity, and low content of residual solvents. These powder characteristics can greatly affect the efficiency, productivity and quality of formulation processes.

The present invention also provides a crystalline Vilazodone hydrochloride, designated Form Zeta. Form Zeta can be characterized by data selected from: a powder XRD pattern having peaks at 5.6, 9.7, 10.7, 11.1 and 16.1 degrees 2θ±0.2 degrees 2θ; a powder XRD pattern as shown in FIG. 51; and any combinations thereof.

Form Zeta may be an ethyl acetate solvate. According to some embodiments, Form Zeta may contain from about 7.0% to about 9.0% w/w of ethyl acetate, for example about 8.5% w/w of ethyl acetate, as measured by GC.

Alternatively, Form Zeta can be characterized by a powder XRD pattern having peaks at 5.6, 9.7, 10.7, 11.1 and 16.1 degrees 2θ±0.2 degrees 2θ, and also having any one or more peaks selected from 13.5, 13.7, 21.3, 24.9 and 26.0 degrees 2θ±0.2 degrees 2θ.

Form Zeta can be further characterized by a DSC thermogram as shown in FIG. 52.

Form Zeta can be characterized by any combination of the above data.

The present invention also provides a crystalline Vilazodone hydrochloride, designated Form Xi. Form Xi can be characterized by data selected from: a powder XRD pattern having peaks at 17.4, 18.8, 22.9, 25.5 and 27.9 degrees 2θ±0.2 degrees 2θ; a powder XRD pattern as shown in FIG. 53; and any combinations thereof.

Form Xi may be a pentanone solvate. For example, Form Xi may contain about 6.0% to about 7.0%, for example about 6.5% w/w of 3-pentaonone, as measured by GC.

Alternatively, Form Xi can be characterized by a powder XRD pattern having peaks at 17.4, 18.8, 22.9, 25.5 and 27.9 degrees 2θ±0.2 degrees 2θ, and also having any one or more peaks selected from 5.5, 9.6, 10.7, 13.9 and 30.1 degrees 2θ±0.2 degrees 2θ.

Form Xi can be further characterized by a DSC thermogram as shown in FIG. 54.

Form Xi can be characterized by any combination of the above data.

The present invention also provides a crystalline Vilazodone hydrochloride, designated Form Omicron. Form Omicron can be characterized by data selected from: a powder XRD pattern having peaks at 5.4, 9.6, 13.6, 15.8 and 22.6 degrees 2θ±0.2 degrees 2θ; a powder XRD pattern as shown in FIG. 55; and any combinations thereof.

Form Omicron may be an ethanol solvate.

Alternatively, Form Omicron can be characterized by a powder XRD pattern having peaks at 5.4, 9.6, 13.6, 15.8 and 22.6 degrees 2θ±0.2 degrees 2θ, and also having any one or more peaks selected from 10.2, 11.3, 17.6, 19.3 and 26.5 degrees 2θ±0.2 degrees 2θ.

Form Omicron can be further characterized by a DSC thermogram as shown in FIG. 56.

Form Omicron can be characterized by any combination of the above data.

The present invention also provides a crystalline Vilazodone hydrochloride, designated Form Pi. Form Pi can be characterized by data selected from: a powder XRD pattern having peaks at 5.3, 11.7, 14.3, 16.9 and 26.0 degrees 2θ±0.2 degrees 2θ; a powder XRD pattern as shown in FIG. 57; and any combinations thereof.

Form Pi may be a dimethylformamide solvate. According to some embodiments, Form Pi may contain from about 4.0% to about 6.0% w/w of DMF, for example, about 5.3% w/w of DMF, as measured by GC.

Alternatively, Form Pi can be characterized by a powder XRD pattern having peaks at 5.3, 11.7, 14.3, 16.9 and 26.0 degrees 2θ±0.2 degrees 2θ, and also having any one or more peaks selected from 10.6, 13.1, 17.6, 18.5 and 20.5 degrees 2θ±0.2 degrees 2θ.

Form Pi can be further characterized by a DSC thermogram as shown in FIG. 58.

Form Pi can be characterized by any combination of the above data.

The present invention also provides a crystalline Vilazodone hydrochloride, designated Form Rho. Form Rho can be characterized by data selected from: a powder XRD pattern having peaks at 5.6, 10.8, 13.4, 22.1 and 25.3 degrees 2θ±0.2 degrees 2θ; a powder XRD pattern as shown in FIG. 59; and any combinations thereof.

Form Rho may be a methyl acetate solvate. According to some embodiments, Form Rho may contain from about 4.0% to about 6.0% w/w of methyl acetate, for example about 4.2% w/w of methyl acetate, as measured by GC.

Alternatively, Form Rho can be characterized by a powder XRD pattern having peaks at 5.6, 10.8, 13.4, 22.1 and 25.3 degrees 2θ±0.2 degrees 2θ, and also having any one or more peaks selected from 9.8, 14.5, 15.3, 22.9 and 28.6 degrees 2θ±0.2 degrees 2θ.

Form Rho can be further characterized by a DSC thermogram as shown in FIG. 60.

Form Rho can be characterized by any combination of the above data.

The present invention also provides a crystalline Vilazodone hydrochloride, designated Form Sigma. Form sigma can be characterized by data selected from: a powder XRD pattern having peaks at 9.1, 19.6, 20.4, 21.8, and 25.7 degrees 2θ±0.2 degrees 2θ; a powder XRD pattern as shown in FIG. 61; and any combinations thereof.

Alternatively, Form Sigma can be characterized by a powder XRD pattern having peaks at 9.1, 19.6, 20.4, 21.8, and 25.7 degrees 2θ±0.2 degrees 2θ, and also having any one or more peaks selected from 8.5, 10.6, 14.4, 16.7, and 22.6 degrees 2θ±0.2 degrees 2θ.

Form Sigma can be characterized by any combination of the above data.

Figure 71:
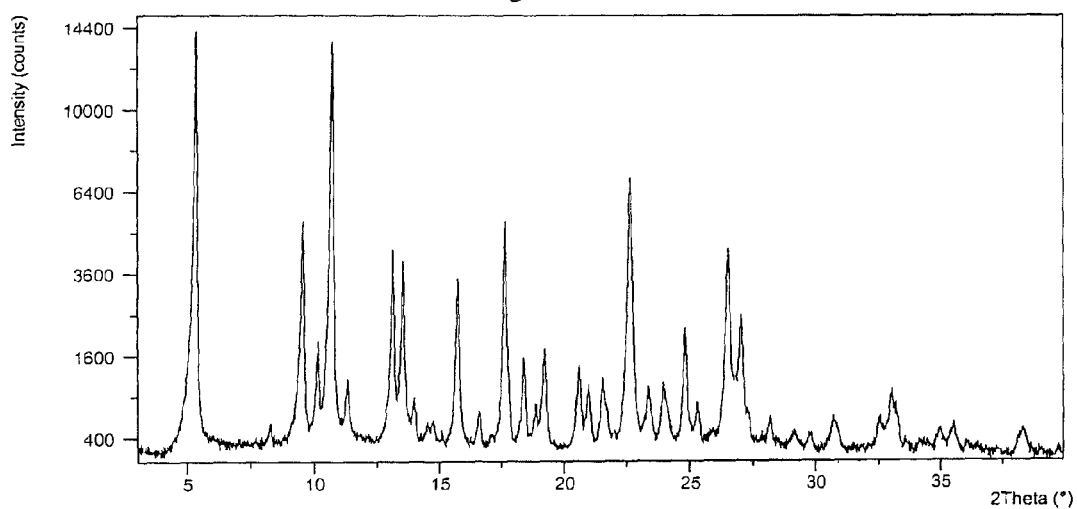
FIG. 71 provides a powder XRD pattern of Form Tau of Vilazodone HCl.
Figure 72:
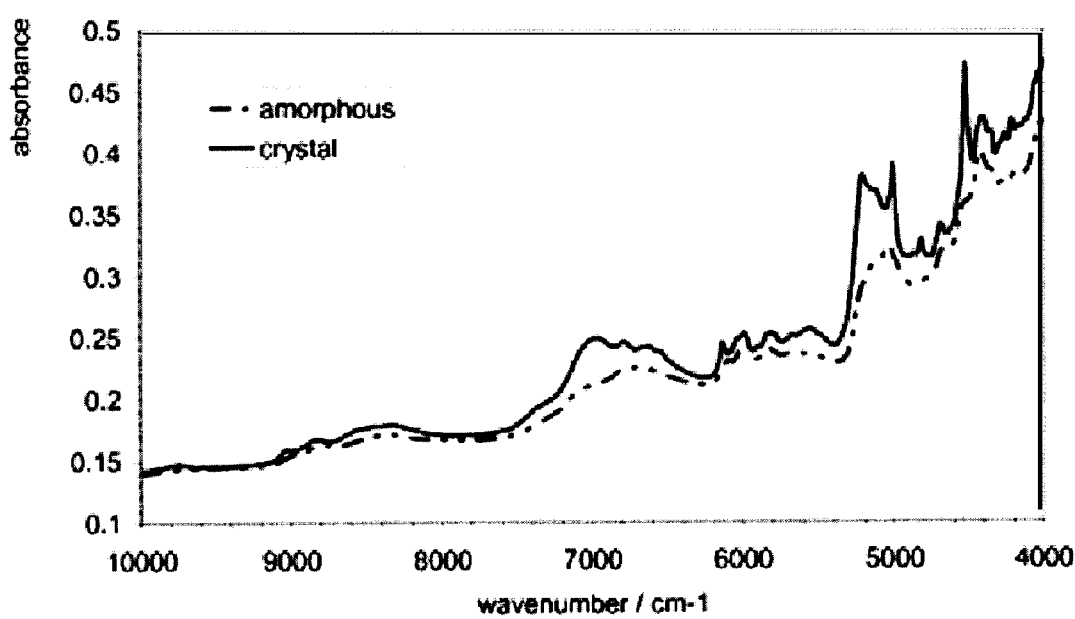
FIG. 72 provides NIR spectra of amorphous and crystalline vilazodone HCl (form Lambda) indicating significant differences.

The present invention also provides a crystalline Vilazodone hydrochloride, designated Form Tau. Form Tau can be characterized by data selected from: a powder XRD pattern having peaks at 5.4, 9.6, 10.7, 13.1, 13.5, 15.7, 17.7, 18.4. 19.2, 22.7, 24.8, 26.5, 27.0 and 33.0° degrees 2θ±0.2 degrees 2θ; a powder XRD pattern as shown in FIG. 71; and any combinations thereof.

Form Tau may be a propanol solvate.

Form Tau can be characterized by any combination of the above data.

The present invention also describes amorphous Vilazodone hydrochloride. The amorphous Vilazodone Hydrochloride can be characterized by a powder XRD pattern as shown in any one of FIGS. 45-46; or by a DSC thermogram as shown in any one of FIGS. 47-48.

The above solid state forms of Vilazodone hydrochloride can be used to prepare Vilazodone, as well as other salts of Vilazodone; and/or solid state forms thereof.

The above solid state forms of Vilazodone and Vilazodone hydrochloride can be also used to prepare pharmaceutical formulations.

The present invention further describes solid dispersions of Vilazodone Hydrochloride.

A solid dispersion of Vilazodone hydrochloride and polyvinylpyrrolidone (PVP) can be characterized by a powder XRD pattern as shown in FIG. 49.

A solid dispersion of Vilazodone hydrochloride and hydroxypropyl methylcellulose (HPMC) can be characterized by a powder XRD pattern as shown in FIG. 50.

The above solid state forms of Vilazodone base or Vilazodone HCl can be used to prepare a different salt of Vilazodone, for example by reacting the above mentioned forms of Vilazodone base with an acid; or by reacting the above mentioned forms of Vilazodone HCl with a suitable base, thereby producing Vilazodone free base, and then reacting the Vilazodone free base product with a different acid, providing a new salt of Vilazodone. Suitable bases include organic bases such as, for example, pyridine, triethylamine, and diisopropylethyl amine, and inorganic bases, e.g., carbonate bases such as, for example, sodium carbonate, potassium carbonate and cesium carbonate; and hydroxide bases, such as, for example potassium hydroxide or sodium hydroxide. Suitable acids include, sulfonate acids, such as, for example, methanesulfonic acid, ethane sulfonic acid, benzene sulfonic acid and toluene sulfonic acid; and mineral acids, such as, for example HCl, HBr, HI, $H_2SO_4$.

In particular, the above mentioned forms are formed by the processes described in the present invention.

The above solid state forms of Vilazodone base or Vilazodone HCl can be used to prepare a pharmaceutical composition comprising any one or more of the above mentioned forms Vilazodone base or Vilazodone HCl, and at least one pharmaceutical acceptable excipient. Preferably, in the pharmaceutical compositions, the solid state forms contain 20% or less, for example 10% or less, or 5% or less, or 2% or less, or 1% or less of any other crystalline form of the respective Vilazodone or Vilazodone HCl.

The present invention further encompasses a pharmaceutical composition comprising any one or combination of solid state Forms of Vilazodone base or Vilazodone HCl, as described above, and at least one pharmaceutically acceptable excipient.

The invention also encompasses a process for preparing a pharmaceutical composition comprising combining any one or more of the above mentioned forms of Vilazodone base or Vilazodone HCl, and at least one pharmaceutical acceptable excipient. In this regard, the resulting pharmaceutical composition may contain the same solid state form as used for preparing said composition, or another solid state form after processing of the composition.

The present invention also provides solid state forms of Vilazodone base or Vilazodone HCl as described above for use as a medicament, preferably for use in treating major depressive disorders.

Having described the invention with reference to certain preferred embodiments, other embodiments will become apparent to one skilled in the art from consideration of the present specification. The invention is further defined by reference to the following examples describing in detail the preparation of the solid state forms and the compositions, as well as the methods of use of the invention. It will be apparent to those skilled in the art that many modifications, both to materials and methods, may be practiced without departing from the scope of the invention.

X-Ray Power Diffraction:

Samples after being powdered in a mortar and pestle were applied directly on silicon plate holder. The X-ray powder diffraction pattern was measured with Philips X'Pert PRO X-ray powder diffractometer, equipped with a $CuK_\alpha$, irradiation source ($\lambda$=1.54184 Å) (Angström), and a X'Celerator (2.022° 2Θ) detector. Scanning parameters: angle range: 3-40 deg., step size 0.0167, time per step 37 s, continuous scan. The described peak positions for several polymorphs were determined by using a silicon powder as an internal standard in mixtures with the sample measured (except for form H, A1 and E1). The position of the silicon (Si) peak was corrected to silicone theoretical peak: 28.45 degrees two theta, and the positions of the measured peaks were corrected respectively.

NIR Instrument:

Bruker MPA FT-NIR spectrometer equipped with quartz beamsplitter, NIR source, PbS detector and Integrating sphere DRIFT accessory, through the bottom of the glass vials containing samples.

Suggested Experimental Parameters:

Resolution: 8 $cm^{-1}$, 64 scans in the range of 10000-4000 $cm^{-1}$.

For the calibration, physical mixtures of amorphous and crystalline vilazodone HCl can be prepared in the concentration range 1-90%. Quantitative method can be developed in the OPUS software (Quant 2, PLS calibration performed after MinMax normalization pretreatment, followed by test set validation).

DSC:

DSC analysis was performed on Q 1000 MDSC TA instruments with heating rate of 10° C./min, under nitrogen flow of 50 ml/min. Standard aluminum, closed pan (with hole) was used, sample mass was about 1-5 mg.

Solid Dispersions:

Silicon was used in the analysis of solid dispersion of Vilazodone hydrochloride and HPMC.

Raman Spectra:

Powder samples to be analyzed were filled into 5 mm NMR tube and Raman spectra were recorded on Nicolet 6700 FT-IR spectrometer with NXR FT-Raman module, equipped with 1064 nm Nd:YVO$_4$ excitation laser, CaF$_2$ beamsplitter and Ge detector.

Instrument Parameters:

Spectral range: 4000-155 cm$^{-1}$
Resolution: 4.0 cm$^{-1}$
Number of scans: 128
Sample gain: auto
Optical velocity: 0.4747
Aperture: 58.84
Laser power: 0.8 W Residual Solvents:

The residual solvent were measured using Capillary gas Chhromatography instrument equipped with autosampler, split/splitless imnjector and flame—ionization detector.
Capillary column: DB-624; 30 m×0.530 mm, 3.00 μm, or demonstrated equivalent.
Analytical balance 0.01 mg
All reagents and standards are chromatograhic grade.
Dimethylsulfoxide (DMSO)
Terahydrofuran, purity grade ≥95%
Acetonitrile, purity grade ≥95%

Chromatographic Conditions:

| | | | |
|---|---|---|---|
| Detector temperature | 250° C. | | |
| Detector | FID | | |
| Carrier | Nitrogen; average linear velocity about 30 cm/s | | |
| Nominal initial flow rate | about 4.0 ml/min at constant pressure of about 19 kPa | | |
| Injector temperature | 140° C. | | |
| Split | 5:1 | | |
| | Ramp/° C./min | Temperature/° C. | Hold time/min |
| Temperature program | 0 | 40 | 5 |
| | 5 | 70 | 0 |
| | 15 | 200 | 10 |
| GC cycle time | 35 min | | |

Preparation of Solution:
BLANK SOLUTION—BLANK
Pipette 5.0 mL of DMSO into 20 mL HS vial.
STANDARD SOLUTION—STDrs
Dissolve an accurately weighed quantity of THF (e.g. THF, purity grade ≥95%), Acetonitrile (e.g. Acetonitrile, purity grade ≥95%) to obtain a solution having known concentration of about 0.028 mg/mL of THF and 0.016 mg/mL of Acetonitrile (e.g. weigh accurately about 70.0 mg of THF and 40.0 mg of Acetonitrile and dissolve in 50.0 mL of DMSO; dilute 1.0 mL of this solution to 50.0 mL with DMSO. Pipette 5.0 mL of obtained solution into 20 mL HS vial.
TEST SOLUTION—Trs
Weigh accurately on 0.01 mg balance about 200.0 mg of sample in 20 mL HS vial. Dissolve in 5.0 mL of DMSO. Prepare in duplicate.

Karl Fischer:

suitable Karl Fischer automatic instrument for coulometric titration with generator electrode without diaphragm; analytical balance, precision: 0.01 mg.
Add about 100 ml of Karl Fischer reagent for coulometric water determination in the titration vessel and perform coulometric titration to the electrometric endpoint to neutralize water content. Transfer accurately about 30 mg of the sample in the titration vessel, stir until it dissolves and perform coulometric titration to the electrometric endpoint. Read the water content of the sample from instrument's display and if it is not calculated by instrument, calculate the percentage that is present in the sample.

EXAMPLES (A) General Procedure for Preparation of Vilazodone Base

Ethyl 5-(piperazine-1-yl)benzofuran-2-carboxylate (10.0 g; 36.5 mmol) was suspended in acetonitrile (84 ml) and water (1 ml). Potassium carbonate (2.52 g; 18.2 mmol), 3-(4-chlorobutyl)-1H-indole-5-carbonitrile (8.5 g; 36.5 mmol), potassium iodide (24.21 g; 145.8 mmol) and tetrabutylammonium bromide (1.18 g; 3.65 mmol) were added sequentially at ambient temperature. The reaction mixture was stirred at reflux temperature (80-82° C.) for 24 hours and then cooled down to room temperature. Acetonitrile (310 ml) and aqueous ammonia (25%; 400 ml) were added. The resulting suspension was stirred for 72 hours and then it was cooled down to about 0° C.-5° C. and stirred for 2 h. The suspension was then filtered and the collected product was washed with water and dried at 60° C. under vacuum to obtain 11.2 g (69.4%) of 5-(4-(4-(5-cyano-1H-indol-3-yl)butyl)piperazin-1-yl)benzofuran-2-carboxamide.

(B) General Procedure for Preparation of Vilazodone Base

Ethyl 5-(piperazine-1-yl)benzofuran-2-carboxylate (10.0 g; 36.5 mmol) was suspended in acetonitrile (84 ml) and water (1 ml). Potassium carbonate (2.52 g; 18.2 mmol), 3-(4-chlorobutyl)-1H-indole-5-carbonitrile (8.5 g; 36.5 mmol), potassium iodide (24.21 g; 145.8 mmol) and tetrabutylammonium iodide (1.33 g; 3.65 mmol) were added sequentially at ambient temperature. The reaction mixture was stirred at reflux temperature (80-82° C.) for 24 hours and then cooled down to room temperature. Acetonitrile (250 ml) was added to the reaction mixture and the resulting mixture was stirred for 30 minutes at room temperature. The resulting suspension was filtered and the collected crude product was washed with acetonitrile (60 ml). Aqueous ammonia (25%; 400 ml) was added to the filtrate and the resulting suspension was stirred for 72 hours. Additional aqueous ammonia (25%; 40 ml) was added and the suspension was stirred for 24 h and then it was cool down to about 0° C.-5° C. and stirred for 2 h. This suspension was then filtered and the collected product was washed with water and dried at 60° C. under vacuum to obtain 13.8 g (85.6%) of 5-(4-(4-(5-cyano-1H-indol-3-yl)butyl)piperazin-1-yl)benzofuran-2-carboxamide.

(C) General Procedure for Preparation of Vilazodone Base

Ethyl 5-(4-(4-(5-cyano-1H-indol-3-yl)butyl)piperazin-1-yl)benzofuran-2-carboxylate (PBCIE; 15 g) was suspended in 7N NH$_3$/MeOH (350 ml) at room temperature and then stirred in autoclave at 50±5° C. for 22 hours. After cooling to 20° C., precipitated off-white solid was filtered off, washed with methanol (20 ml) and dried in vacuum dryer (18 h, 40° C., 10 mbar) to obtain 11.45 g (83%) of 5-(4-(4-(5-cyano-1H-indol-3-yl)butyl)piperazin-1-yl)benzofuran-2-carboxamide (Vilazodone base). Purity (HPLC): 96 Area %.

(D) General Procedure for Preparation of Vilazodone Base

Ethyl 5-(4-(4-(5-cyano-1H-indol-3-yl)butyl)piperazin-1-yl)benzofuran-2-carboxylate hydrochloride (PBCIExHCl; 15 g) was suspended in 7N $NH_3$/MeOH (350 ml) at room temperature and then stirred in autoclave at 50±5° C. for 22 hours. After cooling to 20° C., precipitated off-white solid was filtered off, washed with methanol (20 ml) and dried in vacuum dryer (10 h, 40° C., 10 mbar) to obtain 13.01 g (93%) of 5-(4-(4-(5-cyano-1H-indol-3-yl)butyl)piperazin-1-yl)benzofuran-2- carboxamide (Vilazodone base). Purity (HPLC): 97 Area %.

(E) General Procedure for Preparation of Vilazodone Base

To the solution of ethyl 5-(4-(4-(5-cyano-1H-indol-3-yl)butyl)piperazin-1-yl)benzofuran-2-carboxylate (PBCIE; 3 g; 6.4 mmol; 1 eq) in dry THF (30 ml), at room temperature, formamide (2.32 ml, 58 mmol, 9.1 eq) was added under nitrogen. Resulting solution was heated to 35° C. and NaOMe was added (30% solution in MeOH; 3.16 ml, 16.6 mmol, 2.6 eq). The reaction mixture was heated at 35° C. over 20 h and than cooled down. Water (40 ml) was added and THF was removed in vacuo (white precipitate formed). Ethanol (40 ml) was added and the resulting suspension was heated at 70° C. over 30 min and than cooled to room temperature. Precipitated off-white solid was filtered off, washed with 20 ml $H_2O$/EtOH (4/1) and dried in vacuum dryer (16 h, 50° C., 15 mbar) to obtain 2.38 g (85%) of 5-(4-(4-(5-cyano-1H-indol-3-yl)butyl)piperazin-1-yl)benzofuran-2-carboxamide (Vilazodone base). Purity (HPLC): 98.5 Area %.

(F) General Procedure for Preparation of Vilazodone Base

To the solution of ethyl 5-(4-(4-(5-cyano-1H-indol-3-yl)butyl)piperazin-1-yl)benzofuran-2-carboxylate (PBCIE; 2 g; 4.25 mmol; 1 eq) in dry THF (10 ml), at room temperature, formamide (1.57 ml, 40 mmol, 9.4 eq) and NaOEt (21% in EtOH, 4.42 ml; 11.9 mmol; 2.8 eq) was added under nitrogen. Nitrogen inlet was replaced with $CaCl_2$ tube and the resulting mixture was stirred at room temperature over 1 h. After 1 h water (20 ml) was added dropwise and the mixture was stirred at room temperature over 30 min. Precipitated off-white solid was filtered off, washed with 20 ml $H_2O$/THF (9/1) and dried in vacuum dryer (10 h, 40° C., 10 mbar) to obtain 1.62 g (86%) of 5-(4-(4-(5-cyano-1H-indol-3-yl)butyl)piperazin-1-yl)benzofuran-2-carboxamide (Vilazodone base). Purity (HPLC): 100 Area %.

(G) General Procedure for Preparation of Vilazodone Base

To the solution of ethyl 5-(4-(4-(5-cyano-1H-indol-3-yl)butyl)piperazin-1-yl)benzofuran-2-carboxylate, hydrochloride salt (PBCIExHCl; 5 g; 9.86 mmol; 1 eq) in dry THF (25 ml), at room temperature, formamide (3.9 ml; 98.6 mmol; 10 eq) and NaOEt (21% in EtOH, 11.0 ml; 29.6 mmol; 3 eq) was added under nitrogen. Nitrogen inlet was replaced with $CaCl_2$ tube and the resulting mixture was stirred at room temperature over 1 h. After 1 h water (50 ml) was added dropwise and the mixture was stirred at room temperature over 30 min. Precipitated off-white solid was filtered off, washed with 50 ml $H_2O$/THF (9/1) and dried in vacuum dryer (10 h, 50° C., 10 mbar) to obtain 4.04 g (93%) of 5-(4-(4-(5-cyano-1H-indol-3-yl)butyl)piperazin-1-yl)benzofuran-2- carboxamide (Vilazodone base). Purity (HPLC): 99.3 Area %.

The starting material for Examples 1, 3, 4, 5, and 6 was prepared according to the general procedure (A).

Example 1

Preparation of Vilazodone Form A

Vilazodone base (30 mg) (form B) was suspended in 4.8 ml of methanol by heating at reflux temperature. The suspension was filtered and the filtrate solution was left at room conditions to evaporate. The obtained crystals were characterized by XRPD and DSC.

Example 2

Preparation of Vilazodone Form B

Vilazodone base (103 mg) obtained according to the general procedure B for Vilazodone base synthesis was suspended in 5 ml of methyl isobutyl ketone for 20 hours at room temperature. The suspension was filtered. The obtained crystals were characterized by XRPD and DSC.

Example 3

Preparation of Vilazodone Form C

Vilazodone base (353 mg) was dissolved in 4 ml of ethylene glycol by heating at reflux temperature. The solution was cooled down to room temperature. Crystals formed and were characterized by XRPD and DSC.

Example 4

Preparation of Vilazodone Form D

Vilazodone base (100 mg) was dissolved in 0.8 ml of 1-propanol by heating at reflux temperature. The solution was left at room conditions to evaporate. The thus-obtained crystals were characterized by XRPD and DSC.

Example 5

Preparation of Vilazodone Form E

Vilazodone base (100 mg) was dissolved in 1.4 ml of ethanol by heating at reflux temperature. The solution was left at room conditions to evaporate. The thus-obtained crystals were characterized by XRPD and DSC.

Example 6

Preparation of Vilazodone Form F

Vilazodone base (100 mg) was dissolved in 0.8 ml of 1-buthanol by heating at reflux temperature. The solution was left at room conditions to evaporate. The obtained crystals were characterized by XRPD and DSC.

Example 7

Preparation of Vilazodone Form G

About 5 mg of Vilazodone base Form B was heated in an aluminum closed pan (with hole) with a heating rate of 10° C./min in DSC Q 1000 MDSC TA instruments up to 100° C. The sample was kept isothermally at 100° C. for 5 minutes and then cooled down to room temperature and the thus-obtained powder was characterized by XRPD.

Example 8

Preparation of Vilazodone Form H

About 5 mg of Vilazodone base form A was heated in an aluminum closed pan (with hole) with a heating rate of 10° C./min in DSC Q 1000 MDSC TA instruments up to 159° C. The sample was cooled down to room temperature and the thus-obtained powder was characterized by XRPD.

Example 9

Preparation of Amorphous Vilazodone

About 1.5 g of Vilazodone base Form B was ground in solid state in the Pulverisettte 7 ball planetary mill. The samples were ground in 50 ml SiN jars with 7 SiN balls (10 mm diameter) with 600 rpm in time duration of 50 minutes. The obtained solid was analyzed by XRPD and DSC and the resulting diffraction pattern and DSC thermogram are shown in the FIG. 15 and FIG. 16.

Example 10

Preparation of Vilazodone Form I

About 5 mg of amorphous Vilazodone base obtained by grinding was heated in an aluminum closed pan (with hole) with a heating rate of 10° C./min in DSC Q 1000 MDSC TA instruments up to 140° C. The sample was cooled down to room temperature (RT) and the thus-obtained powder was characterized by XRPD.

Example 11

Preparation of Vilazodone base Form E1

Amorphous Vilazodone base (100 mg) prepared by solid state grinding was suspended in 1 ml of ethanol and stirred at RT for 4 days. The suspension was filtered and the collected powder was analyzed by XRPD and DSC.

Example 12

Preparation of Vilazodone base Form A1

Amorphous Vilazodone base (100 mg), prepared by solid state grinding, was suspended in 1 ml of methanol and stirred at RT for 4 days. The suspension was filtered and the collected powder was analyzed by XRPD and DSC.

Example 13

Preparation of Vilazodone base Form A1

Ethyl 5-(4-(4-(5-cyano-1H-indol-3-yl)butyl)piperazin-1-yl)benzofuran-2-carboxylate hydrochloride (100 mg) was suspended in methanol (5 ml) at room temperature. Ammonia water solution (25%, 5 ml) was added to the suspension. The obtained mixture was stirred overnight at room temperature. The resulting crystals were filtered off, washed with a methanol/water mixture and then with water; and dried at 45° C. in vacuum. 71 mg of vilazodone base was isolated and characterized by XRPD and DSC.

Example 14

Amorphous Form of Vilazodone Base Prepared by Spray Drying

Vilazodone base (1.0 g) was dissolved in 150 ml of methanol at 65° C. The solution was filtered and the filtrate was spray dried under the following conditions: $T_{in1}=85°$ C., Aspirator=100% and Pump=20%. The resulting powder was analyzed by XRPD and DSC.

Example 15

Amorphous Form of Vilazodone HCl Prepared by Spray Drying

Vilazodone HCl (0.7 g) was dissolved in 200 ml of methanol at 65° C. The solution was filtered and the filtrate was spray dried under the following conditions: $T_{in1}=85°$ C., Aspirator=100% and Pump=20%. The resulting powder was analyzed by XRPD and DSC.

Example 16

Amorphous Form of Vilazodone HCl Prepared by Grinding

Vilazodone base (2.0 g) was ground in solid state in the Pulverisette 7 ball planetary mill. The sample was ground in 50 ml SiN jars with 10 SiN balls (10 mm in diameter) with 500 rpm in time duration of 180 minutes. The resulting powder was analyzed by XRPD and DSC.

Example 17

Preparation of Crystalline Form Alpha of Vilazodone HCl

Vilazodone base Form B (1 g), was suspended in methanol (10 ml) at room temperature. HCl solution in methanol was added dropwise slowly until the pH reached 1-2. The obtained suspension was stirred for 30 minutes. Crystals formed and were filtered off and washed with methanol. The resulting powder was analyzed by XRPD and DSC.

Example 18

Preparation of Crystalline Form Beta of Vilazodone HCl

Vilazodone base (10 g) was dissolved in dimethylformamide (100 ml) at room temperature. The solution was filtered and then cooled to 10-15° C. HCl solution in diethylether (2.0 M) was added dropwise until the pH reached 2.3. The obtained solution was cooled to 0-5° C. and stirred overnight. Crystals formed and were filtered off, washed with 3×10 ml of diethylether and dried at 50° C. in vacuum. Vilazodone hydrochloride (5.2 g) was obtained and this product was analyzed by XRPD and DSC.

Example 19

Preparation of Crystalline Form Gamma of Vilazodone HCl

Vilazodone HCl (200 mg) was dissolved in 2 ml of N-methylpyrrolidone at about 100° C., and was then cooled down to about 70° C. The solution was added dropwise into hot ethyl acetate (previously heated at 60° C.). The resulting suspension was cooled down to RT and was filtered. The collected powder was analyzed by XRPD and DSC.

Example 20

Preparation of Crystalline Form Delta of Vilazodone HCl

Vilazodone HCl (200 mg) was dissolved in 2 ml of N-methylpyrrolidone at about 100° C., and then cooled down to about 70° C. and this cooled solution was added dropwise into hot acetone (previously heated at 56° C.). The obtained suspension was cooled down to RT and was filtered. The collected powder was analyzed by XRPD and DSC.

Example 21

Preparation of Crystalline Form Epsilon of Vilazodone HCl

Vilazodone base Form B (1 g) was suspended in ethyl acetate (20 ml) at room temperature. An HCl solution in ethyl-acetate (1.0 M) was added in portions slowly until the pH reached 1.2 and remained constant for 15 minutes. The resulting crystals were filtered off and washed with ethyl acetate. The obtained Vilazodone hydrochloride powder was analyzed by XRPD and DSC.

Example 22

Preparation of Crystalline Form Eta of Vilazodone HCl

Amorphous vilazodone HCl (100 mg) was suspended in 1 ml of methyl ethyl ketone and stirred at RT for 2 days. The suspension was filtered off and the collected powder was analyzed by XRPD and DSC.

Example 23

Preparation of Crystalline Form Theta of Vilazodone HCl

Amorphous vilazodone HCl (100 mg) was suspended in 1 ml of n-butyl acetate and stirred at RT for 2 days. The suspension was filtered and the collected powder was analyzed by XRPD and DSC.

Example 24

Preparation of Crystalline Form Iota of Vilazodone HCl

Vilazodone HCl (300 mg) was dissolved in 10 ml of ethylene glycol at 120° C. The solution was cooled down at RT and stirred for 3 days. The thus-obtained suspension was filtered off and the collected powder was analyzed by XRPD and DSC.

Example 25

Preparation of Crystalline Form Kappa of Vilazodone HCl

Vilazodone HCl (30 mg) was suspended in 5 ml of 1-propanol. The suspension was heated at 97° C. and was then filtered. The resulting filtrate was left open at room conditions to evaporate. The obtained product was analyzed by XRPD.

Example 26

Preparation of Crystalline Form Lambda of Vilazodone HCl

Vilazodone HCl (200 mg) was dissolved in 2 ml of dimethylformamide at about 140° C., and the solution was then cooled down to about 70° C. and was added dropwise into water (previously heated to 60° C.). The resulting solution was stirred at 60° C. for 30 minutes and was then cooled to RT and stirred to form a suspension. The obtained suspension was filtered and the collected product was dried at 60° C. for 48 hours, under vacuum. The dried product was analyzed by XRPD and DSC.

Example 27

Preparation of Crystalline Form Lambda of Vilazodone HCl

Vilazodone HCl (200 mg) was dissolved in 2 ml of dimethylsulfoxide at about 90° C., and the solution was then cooled down to about 70° C. and was added dropwise into water (6 ml) (previously heated to 60° C.). The resulting solution was stirred at 60° C. for 30 minutes and was then cooled to RT and stirred to form a suspension. The suspension was filtered and the collected product was dried at 60° C. for 48 hours under vacuum. The resulting powder was analyzed by XRPD and DSC.

Example 28

Preparation of Crystalline Form Lambda of Vilazodone HCl

Vilazodone HCl (200 mg) was dissolved in 2 ml of N-methylpyrrolidone at about 100° C., and the solution was then cooled to about 70° C. and was added dropwise into water (6 ml) (previously heated to 60° C.). The resulting solution was stirred at 60° C. for 30 minutes and then cooled to RT and stirred. The thus obtained suspension was filtered and the collected product was dried at 60° C. for 48 hours, under vacuum. The resulting powder was analyzed by XRPD and DSC.

Example 29

Preparation of Crystalline Form Lambda of Vilazodone HCl

Vilazodone HCl (200 mg) was dissolved in 2 ml of dimethylformamide at about 140° C., and the solution was cooled to about 70° C. Into the prepared solution water (6 ml, previously heated at 60° C.) was added dropwise. The resulting solution was stirred at 60° C. for 30 minutes and was then cooled to RT and stirred. The obtained suspension was filtered and the collected product was dried at 60° C. for 48 hours under vacuum. The resulting powder was analyzed by XRPD and DSC.

Example 30

Preparation of Crystalline Form Lambda of Vilazodone HCl

Vilazodone HCl (200 mg) was dissolved in 2 ml of dimethylsulfoxide at about 90° C., and the solution was cooled to about 70° C. Into the prepared solution, water (6 ml, previously heated at 60° C.) was added dropwise. The resulting solution was stirred at 60° C. for 30 minutes and was then cooled to RT and stirred. The obtained suspension was filtered and the collected product was dried at 60° C. for 48 hours under vacuum. The resulting powder was analyzed by XRPD and DSC.

Example 31

Preparation of Crystalline Form Mu of Vilazodone HCl

About 5 mg of Vilazodone HCl, Form Lambda, was heated in an aluminum closed pan (with hole) with a heating rate of 10° C./min in DSC Q 1000 MDSC TA instruments up to 139° C. The sample was cooled down to room temperature and the thus-obtained powder was characterized by XRPD.

Example 32

Preparation of Crystalline Form Nu of Vilazodone HCl

About 5 mg of Vilazodone HCl, Form Alpha, was heated in an aluminum closed pan (with hole) with a heating rate of 10° C./min in DSC Q 1000 MDSC TA instruments up to 134° C. The sample was cooled down to room temperature and the thus-obtained powder was characterized by XRPD.

Example 33

Amorphous Solid Dispersion of Vilazodone HCl and PVP

Polyvinylpyrrolidone (PVP) (0.7 g) was dissolved in 200 ml of methanol. The methanol solution of PVP was added into a solution 0.7 g of vilazodone HCl. The resulting mixture was heated to 65° C. and dissolution occurred. The obtained solution was filtered and the filtrate was spray dried under the following conditions: $T_{in1}$=85° C., Aspirator=100% and Pump=20%. The resulting powder was analyzed by XRPD.

Example 34

Amorphous Solid Dispersion of Vilazodone HCl and HPMC

Hydroxypropyl methylcellulose (HPMC) (0.7 g) was dissolved in 200 ml of methanol. The methanol solution of HPMC was added into a solution 0.7 g of vilazodone HCl. The obtained mixture was heated to 65° C. and dissolution occurred. The resulting solution was filtered and the filtrate was spray dried under the following conditions: $T_{in1}$=85° C., Aspirator=100% and Pump=20%. The resulting powder was analyzed by XRPD.

Example 35

Preparation of Crystalline Form Zeta of Vilazodone HCl

Vilazodone HCl (30 mg, amorphous form) was suspended in 0.2 ml of ethyl acetate and stirred at room conditions for 2 days. Suspension was filtrated off and analyzed by XRPD.

Example 36

Preparation of Crystalline Form Xi of Vilazodone HCl

About 0.5 g of amorphous Vilazodone HCl, obtained by solid state dry grinding, was placed in a desiccator. The powder sample was exposed to the volatile ethyl acetate solvent and kept at room temperature. Crystalline traces were detected by XRPD after 30 days. The sample was kept in ethyl acetate atmosphere for additional 30 days and characterized by XRPD and DSC.

Example 37

Preparation of Crystalline Form Omicron of Vilazodone HCl

About 0.5 g of amorphous Vilazodone HCl, obtained by solid state dry grinding, was placed in a desiccator. The powder sample was exposed to the volatile ethanol (tech.) solvent and kept at room temperature. Crystalline traces were detected by XRPD after 30 days. Sample was kept in ethanol (tech.) atmosphere for additional 30 days and characterized by XRPD and DSC.

Example 38

Preparation of Crystalline Form Pi of Vilazodone HCl

About 0.5 g of amorphous Vilazodone HCl, obtained by solid state dry grinding, was placed in a desiccator. The powder sample was exposed to the volatile dimethylformamide (DMF) solvent and kept at room temperature. Crystalline traces were detected by XRPD after 30 days. Sample was kept in DMF atmosphere for additional 30 days and characterized by XRPD and DSC.

Example 39

Preparation of Crystalline Form Rho of Vilazodone HCl

About 0.5 g of amorphous Vilazodone HCl, obtained by solid state dry grinding, was placed in a desiccator. The powder sample was exposed to the volatile methyl acetate solvent and kept at room temperature. Crystalline traces were detected by XRPD after 30 days. Sample was kept in a methyl acetate atmosphere for an additional 30 days and then characterized by XRPD and DSC.

Example 40

Preparation of Amorphous Vilazodone HCl

Vilazodone HCl (1 g) was suspended in 15 ml of tetrahydrofuran and stirred at room temperature. Water was added in portions (0.5 ml) until the volume 6 ml was reached, and substance was dissolved. The solution was filtrated and then it was spray dried at following conditions: Aspiration=100%, Pump 20%, Tin1=110° C., Tout=65° C.

Example 41

Preparation of Amorphous Vilazodone HCl

Vilazodone HCl (1 g) was suspended in 30 ml of acetonitrile and stirred at room temperature. Water was added in portions (0.5 ml) until the volume 15 ml was reached, and substance was dissolved. Solution was filtrated and then it was spray dried at following conditions: Aspiration=100%, Pump 20%, $T_{in1}$=110° C., $T_{out}$=65° C.

Example 42

Preparation of Crystalline Form Alpha of Vilazodone HCl

Vilazodone base (20 g, Form B-hydrate) was suspended in 200 ml of methanol. 100 ml of 0.5M HCl (in methanol) was added into suspension, dropwise. The suspension was stirred for 1 hour at room temperature, filtrated off and washed with 20 ml of methanol.

Example 43

Preparation of Crystalline Form Alpha of Vilazodone HCl

Vilazodone base (30 g Form A-methanol solvate) was suspended in 300 ml of methanol. 200 ml of 0.5M HCl (in methanol) was added into the suspension, dropwise, stirred for 1 hour and filtrated off, washed with 30 ml of methanol. The product was suspended in 300 ml methanol and 10 ml of 3M HCl was added dropwise. The suspension was stirred for 20 hours at room temperature, filtrated off and dried at room conditions.

Example 44

Preparation of Crystalline Form Nu of Vilazodone HCl

Vilazodone HCl (26 g, form Alpha) was dried at 50° C., for 20 hours, under vacuum.

Example 45

Preparation of Crystalline from Lambda of Vilazodone HCl

Vilazodone HCl (24 g, form Nu) was suspended in 240 ml of water. The suspension was stirred for 3 h at room temperature. The product was filtered off and dried at 40° C. for 2 h, under vacuum.

Example 46

Preparation of Crystalline Form Lambda of Vilazodone HCl

Vilazodone base (300 mg, Form A-methanol solvate) was suspended in 10 ml of water. HCl (5 ml of 0.25M) was added into suspension, dropwise. The suspension was stirred for 1 hour, filtered off and washed with 2 ml of methanol.

Example 47

Preparation of Crystalline Form Lambda of Vilazodone HCl

Vilazodone base (13.9 g, Form B-hydrate) was suspended in 140 ml of water. HCl (130 ml of 0.25M) was added into suspension, dropwise. The resulting suspension was stirred for 1 hour at room temperature, filtered off and washed with 40 ml of water. The product was dried at 40° C. for 210 minutes, under vacuum.

Example 48

Preparation of Crystalline Form Sigma of Vilazodone HCl

A sample of Vilazodone HCl, Form Alpha was subjected to a DVS (Dynamic Vapor Sorption) experiment utilizing SMS DVS instrument. One sorption-de sorption cycle in humidity range 0%-90%-0% RH was performed, with increments of 10% RH. The sample mass was 23.7 mg. The experiment was performed at 25° C. After the DVS experiment, the sample was analyzed by XRD, thereby determining that new crystalline compound of Vilazodone HCl, was obtained.

Example 49

Preparation of Form K of Vilazodone Base 5-(4-(4-(5-cyano-1H-indol-3-yl)butyl)piperazin-1-yl) benzofuran-2-carboxamide (Vilazodone base) (1000 mg) was suspended in tetrahydrofuran (7 ml) at room temperature. The suspension was heated to 60° C. and water (0.4 ml) was added to dissolve. The solution was cooled down to room temperature and water (6 ml) was added dropwise. At the end of water addition crystallization started. The suspension was stirred for another hour at room temperature. The resulting crystals were filtered off, washed with a tetrahydrofuran:water mixture 1:1 (2 ml) and dried in open plate at room conditions. 790 mg of vilazodone base form K was isolated and characterized by XRPD and DSC.

Example 50

Preparation of Form L of Vilazodone Base 5-(4-(4-(5-cyano-1H-indol-3-yl)butyl)piperazin-1-yl) benzofuran-2-carboxamide hydrochloride (400 mg) was suspended in tetrahydrofuran:water 1:1 mixture (8 ml) at room temperature. The suspension was heated to 55° C. and tetrahydrofuran:water mixture 1:1 was added in portions until dissolved (5 ml added). Ammonia water solution (25%, 1.6 ml) was added to the solution. Crystallization started during ammonia addition. The obtained mixture was cooled down to room temperature and stirred for another hour. The resulting crystals were filtered off, washed with tetrahydrofuran:water mixture 1:1 (2 ml) and dried in open plate at room conditions. 320 mg of vilazodone base form L was isolated and characterized by XRPD and DSC.

Example 51

Preparation of Form L of Vilazodone Base 5-(4-(4-(5-cyano-1H-indol-3-yl)butyl)piperazin-1-yl)benzofuran-2-carboxamide (Vilazodone base) (1000 mg) was suspended in tetrahydrofuran (10 ml) at room temperature. Water (7 ml) was added dropwise. At the beginning of water addition dissolving is occurred and by further addition crystallization started. The suspension was stirred at room temperature for another hour. The resulting crystals were filtered off, washed with tetrahydrofuran:water mixture 1:1 (2 ml) and dried in open plate at room conditions. 860 mg of vilazodone base form L was isolated and characterized by XRPD and DSC. KF=7.8%. GC (THF)=7556 ppm.

Example 52

Preparation of Form Lambda of Vilazodone HCl 5-(4-(4-(5-Cyano-1H-indol-3-yl)butyl)piperazin-1-yl)benzofuran-2-carboxamide (Vilazodone base) (45 g; 0.102 mol) was suspended in water (450 mL) and THF (112.5 mL) at room temperature. The reaction mixture was stirred for 5 minutes. The 0.25 M hydrochloric acid (483 mL) was added dropwise over twenty five minutes to adjust pH to 2 and reaction mixture was stirred for additionally 1 hour at room temperature. Crystals were filtrated off, washed with 112.5 mL of water and dried (18 h, 45° C., 10 mbar). Yield: 47.5 g; (97.5%) of Vilazodone hydrochloride form lambda as determined by XRPD.

Example 53

Preparation of Form Alpha of Vilazodone HCl

Vilazodone HCl form lambda (1.0 g) was suspended in methanol (20 ml). The suspension was stirred at room temperature overnight. Crystals were filtered off, washed with methanol (5 ml) and dried in open plate at room conditions. Form Alpha was obtained as determined by XRPD.

Example 54

Preparation of Form Alpha of Vilazodone HCl

Semicrystalline form Lambda (0.5 g) was placed in desiccator in the atmosphere of methanol at 25° C. In this experiment vapours of volatile organic solvent (methanol) interacts with the powder surface of form lambda. One month later the sample was checked by XRPD and conversion to form Alpha was obtained, based on XRPD measurement.

Example 55

Preparation of Form M of Vilazodone

To a suspension of ethyl 5-(4-(4-(5-cyano-1H-indol-3-yl)butyl)piperazin-1-yl)benzofuran-2-carboxylate, hydrochloride salt (PBCIE×HCl; 30 g; 59.2 mmol; 1 eq) in dry THF (150 ml), at room temperature, absolute ethanol (60 ml) and formamide (117.5 ml, 2958 mmol, 50 eq) were added. Solid NaOEt (95%; 12.7 g; 177 mmol; 3 eq) were added. The reaction mixture was stirred at room temperature for 1 h and at 70° C. for 15 min. Water (300 ml) was added dropwise at 70° C. over 25 min. The reaction mixture was cooled down to room temperature over 1 h, and the resulting solid was filtered off, washed with 300 ml THF/H$_2$O (1/9) and dried (10 h, 50° C., 10 mbar). Yield: 24.11 g (92%) of 5-(4-(4-(5-cyano-1H-indol-3-yl)butyl)piperazin-1- yl)benzofuran-2-carboxamide. purity (HPLC): 99.4 Area %.

Example 56

Preparation of Form M of Vilazodone

To a suspension of ethyl 5-(4-(4-(5-cyano-1H-indol-3-yl)butyl)piperazin-1-yl)benzofuran-2-carboxylate, hydrochloride salt (PBCIE×HCl; 40 g; 78.9 mmol; 1 eq) in dry THF (200 ml), at room temperature, formamide (156.8 ml, 3944 mmol, 50 eq) and solid NaOEt (95%; 16.1 g; 236 mmol; 3 eq) were added. The reaction mixture was stirred at room temperature for 1 h and at 65° C. for 15 min. Water (400 ml) was added dropwise at 65° C. over 35 min. The reaction mixture was cooled down to room temperature over 1 h. The resulting suspension was mixed 1 h and the resulting solid was filtered off, washed with 2×200 ml THF/H$_2$O (1/9) and dried (15 h, 45° C., 10 mbar). Yield: 31.03 g (89%) of 5-(4-(4-(5-cyano-1H-indol-3-yl)butyl)piperazin-1- yl)benzofuran-2-carboxamide. Purity (HPLC): 99.55 Area %.

Example 57

Preparation of Form Lambda of Vilazodone HCl 5-(4-(4-(5-Cyano-1H-indol-3-yl)butyl)piperazin-1-yl)benzofuran-2-carboxamide (Vilazodone base) (90 g; 0.204 mol) was suspended in THF (225 mL) at room temperature. Water (900 mL) was added dropwise during 10 minutes. Hydrochloric acid (975 mL, 0.25 M) was added dropwise over 15 minutes, pH was adjusted to 1.85 and the reaction mixture was stirred additionally 2.5 hours at room temperature. Crystals formed and were filtered off, washed with water (2×150 mL) and dried (14 h, 40° C., 10 mbar). Yield: 88.3 g; (90.6%) of Vilazodone hydrochloride form lambda was characterized by XRPD.

Example 58

Preparation of Form Alpha of Vilazodone HCl 5 g of Vilazodone HCl form lambda was dispersed in methanol solution (100 ml) and vortexed about 3 h. Suspension was vacuumed filtered off and washed out with 10 ml of water. The isolated crude material was measured by XRPD and DSC and form Alpha with the amorphous presence was found.

Example 59

Preparation of Anhydrous Form Mu of Vilazodone HCl

About 39 g of vilazodone hydrochloride, form Lambda, was dried in vacuum drier at about 100° C. in duration of about 2.5 hours. Semicrystalline form of Vilazodone HCl, Form Mu, was determined by XRPD and DSC.

Example 60

Preparation of Anhydrous Form Mu of Vilazodone HCl

About 5 g of vilazodone hydrochloride, Form Lambda, was dried in vacuum drier at about 80° C. in duration of about 5 hours. The material was analyzed by XRPD while process of drying. Amorphous content is detected while polymorphic transformation from vilazodone hydrochloride form lambda to anhydrous form Mu.

Example 61

Preparation of Form Tau of Vilazodone HCl

Vilazodone hydrochloride form lambda (2.0 g) was suspended in 1-propanol (40 ml) at room temperature overnight (about 17 h). Crystals were filtered off and analysed by XRPD.

The invention claimed is:

1. A crystalline Form alpha of Vilazodone HCl, characterized by a powder X-ray diffraction (XRD) pattern having peaks at 7.1, 7.9, 12.7, 17.4, 21.7 and 25.9 degrees 2θ±0.2 degrees 2θ.

2. The crystalline Form alpha of Vilazodone HCl according to claim 1, further characterized by any one, two, three, four, five, six or seven peaks selected from the group consisting of 8.7, 10.5, 12.1, 15.0, 16.3, 19.7, and 22.5 degrees 2θ±0.2 degrees 2θ.

3. The crystalline Form alpha of Vilazodone HCl according to claim 1, further characterized by a differential scanning calorimetry (DSC) thermogram as shown in FIG. 25.

4. A process for preparing the crystalline Form alpha of Vilazodone HCl of claim 1, comprising combining Vilazodone base with methanol.

5. A pharmaceutical composition comprising the crystalline Form alpha of Vilazodone HCl according to claim 1 and at least one pharmaceutically acceptable excipient.

6. A method of treating a major depressive disorder in a patient, comprising administering to the patient a therapeutically effective dose of the crystalline Form alpha of Vilazodone HCl according to claim 1.

7. A process for preparing a pharmaceutical composition comprising combining the crystalline Form alpha of Vilazodone HCl according to claim 1 and at least one pharmaceutically acceptable excipient.

8. The crystalline Form alpha of Vilazodone HCl according to claim 1, further characterized by a Raman spectrum having peaks at 3112.1, 2968.6, 2915.2, 2850.1, 2220.1, 1613.8, 1579.4, 1547.1, 1437.9, 1269.3, 1124.4, 824.3, 500.3, 408.4±4 cm$^{-1}$.

9. The crystalline Form alpha of Vilazodone HCl according to claim 1, further characterized by a powder XRD pattern as shown in FIG. 24.

10. The crystalline form alpha of Vilazodone HCl according to claim 1, further characterized by a Raman spectrum as shown in FIG. 68.

11. The crystalline form alpha of Vilazodone HCl according to claim 1, which contains about 3.0 to about 10.0 w/w of water as measured by Karl Fischer (KF) titration.

12. The crystalline form alpha of Vilazodone HCl according to claim 9, which contains about 5.0 to about 7.0% w/w of water as measured by KF.

13. A process for preparing the crystalline Form alpha of Vilazodone HCl of claim 1, comprising combining another Vilazodone HCl Form with methanol.

14. The process of claim 13, wherein the other Vilazodone HCl Form is Vilazodone HCl form lambda, characterized by data selected from the group consisting of:

a powder XRD pattern having peaks at 12.3, 14.8, 15.6, 16.6 and 24.6 degrees 2θ±0.2 degrees 2θ;
a powder XRD pattern as shown in FIG. 41;
a Raman spectrum having peaks at 3124.1, 3078.3, 2995.9, 2878.0, 2851.0, 2217.6, 1676.4, 1615.7, 1593.1, 1578.4, 1549.6, 1439.4, 1364.0, 1243.4, 1136.9, 938.9, 822.0, 771.5, 752.9, 408.1±4 cm$^{-1}$;
a Raman spectrum as shown in FIG. 70;
and any combination thereof.

* * * * *